US012576047B2

(12) United States Patent
Priel

(10) Patent No.: US 12,576,047 B2
(45) Date of Patent: Mar. 17, 2026

(54) TELOMERASE ACTIVATING COMPOUNDS FOR USE IN FERTILITY AND RELATED APPLICATIONS

(71) Applicant: Neuromagen Pharma Ltd, Beersheva (IL)

(72) Inventor: Esther Priel, Beersheva (IL)

(73) Assignee: Neuromagen Pharma Ltd, Beersheva (IL)

( * ) Notice: Subject to any disclaimer, the term of this patent is extended or adjusted under 35 U.S.C. 154(b) by 41 days.

(21) Appl. No.: 18/456,178

(22) Filed: Aug. 25, 2023

(65) Prior Publication Data

US 2024/0180851 A1 Jun. 6, 2024

Related U.S. Application Data

(63) Continuation of application No. 16/485,416, filed as application No. PCT/IL2018/050161 on Feb. 12, 2018, now Pat. No. 11,857,516.

(60) Provisional application No. 62/458,028, filed on Feb. 13, 2017.

(30) Foreign Application Priority Data

Feb. 12, 2017 (IL) .......................................... 250567
Feb. 11, 2018 (IL) .......................................... 257470

(51) Int. Cl.

| | |
|---|---|
| ***A61K 31/09*** | (2006.01) |
| ***A61K 31/05*** | (2006.01) |
| ***A61K 31/137*** | (2006.01) |
| ***A61K 31/4025*** | (2006.01) |
| ***A61K 31/4545*** | (2006.01) |
| ***A61K 31/5377*** | (2006.01) |
| ***A61K 31/66*** | (2006.01) |
| ***A61P 15/08*** | (2006.01) |

(52) U.S. Cl.

CPC .............. *A61K 31/09* (2013.01); *A61K 31/05* (2013.01); *A61K 31/137* (2013.01); *A61K 31/4025* (2013.01); *A61K 31/4545* (2013.01); *A61K 31/5377* (2013.01); *A61K 31/66* (2013.01); *A61P 15/08* (2018.01)

(58) Field of Classification Search

CPC ...... A61K 31/05; A61K 31/055; A61K 31/09; A61K 31/137; A61K 31/4025; A61K 31/4545; A61K 31/496; A61K 31/5377; A61K 31/66; A61P 15/00; A61P 15/08; A61P 35/00; A61P 43/00

See application file for complete search history.

(56) References Cited

U.S. PATENT DOCUMENTS

| | | | |
|---|---|---|---|
| 8,604,245 B2 | 12/2013 | Priel et al. |
| 8,609,736 B2 | 12/2013 | Gazit et al. |
| 9,663,448 B2 | 5/2017 | Priel et al. |
| 9,670,138 B2 | 6/2017 | Priel et al. |
| 9,670,139 B2 | 6/2017 | Gazit et al. |
| 10,214,481 B2 | 2/2019 | Priel |
| 11,857,516 B2 | 1/2024 | Priel |

FOREIGN PATENT DOCUMENTS

| | | |
|---|---|---|
| WO | WO 2008/149345 A2 | 12/2008 |
| WO | WO 2008/149353 A2 | 12/2008 |
| WO | WO 2015/068156 A1 | 5/2015 |
| WO | WO 2018/146689 A1 | 8/2018 |

OTHER PUBLICATIONS

Butts et al., "Correlation of Telomere Length and Telomerase Activity with Occult Ovarian Insufficiency," J Clin Endocrinol Metab, 94:4835-4843, (Oct. 2009).
Eitan, et al., "Novel telomerase-increasing compound in mouse brain delays the onset of amyotrophic lateral sclerosis," EMBO Mol. Med, 4, 313-329, (2012).
Mark-Kappeler et al., "Xenobiotic Effects on Ovarian Preantral Follicles," Biology of Reproduction, 85, 871-883, (Jun. 2011).
PCT/IL2018/050161 International Search Report mailed May 28, 2018.
PCT/IL2018/050161 Written Opinion of the International Searching Authority mailed May 28, 2018.
PCT/IL2018/050161 International Preliminary Report on Patentability mailed Aug. 13, 2019.
U.S. Appl. No. 16/485,416 Restriction Requirement mailed Sep. 21, 2021.
U.S. Appl. No. 16/485,416 Non-Final Office Action mailed Mar. 7, 2022.

*Primary Examiner* — Sarah Pihonak
(74) *Attorney, Agent, or Firm* — Alston & Bird LLP

(57) ABSTRACT

The present invention is directed to methods and uses of a series of compounds and compositions comprising the same for treating diseases, disorders and/or conditions related to fertility and preserving same and conditions related to same. In some aspects, the compounds and or compositions as herein described promote, improve, recover or restore fertility in a subject in need thereof, including in male and/or female subjects. Such methods/uses include promoting, enhancing or improving fertility-associated cell or tissue yield as part of an in vitro fertilization protocol.

13 Claims, 24 Drawing Sheets

Specification includes a Sequence Listing.

SEQUENCE LISTING

```
Sequence total quantity: 8
SEQ ID NO: 1            moltype = DNA  length = 18
FEATURE                 Location/Qualifiers
misc_feature            1..18
                        note = Synthetic Primer Sequence
source                  1..18
                        mol_type = other DNA
                        organism = synthetic construct
SEQUENCE: 1
aatccgtcga gcagagtt                                                18

SEQ ID NO: 2            moltype = DNA  length = 30
FEATURE                 Location/Qualifiers
misc_feature            1..30
                        note = Synthetic Primer Sequence
source                  1..30
```

-continued

```
                       mol_type = other DNA
                       organism = synthetic construct
SEQUENCE: 2
gcgcggctta cccttaccct taccctaacc                                       30

SEQ ID NO: 3           moltype = DNA  length = 36
FEATURE                Location/Qualifiers
misc_feature           1..36
                       note = Synthetic Primer Sequence
source                 1..36
                       mol_type = other DNA
                       organism = synthetic construct
SEQUENCE: 3
aatccgtcga gcagagttaa aaggccgaga agcgat                                36

SEQ ID NO: 4           moltype = DNA  length = 18
FEATURE                Location/Qualifiers
misc_feature           1..18
                       note = Synthetic Primer Sequence
source                 1..18
                       mol_type = other DNA
                       organism = synthetic construct
SEQUENCE: 4
atcgcttctc ggcctttt                                                    18

SEQ ID NO: 5           moltype = DNA  length = 23
FEATURE                Location/Qualifiers
misc_feature           1..23
                       note = Synthetic Primer Sequence
source                 1..23
                       mol_type = other DNA
                       organism = synthetic construct
SEQUENCE: 5
gaaagtagag gattgccact ggc                                              23

SEQ ID NO: 6           moltype = DNA  length = 23
FEATURE                Location/Qualifiers
misc_feature           1..23
                       note = Synthetic Primer Sequence
source                 1..23
                       mol_type = other DNA
                       organism = synthetic construct
SEQUENCE: 6
cgtatgtgtc catcagccag aac                                              23

SEQ ID NO: 7           moltype = DNA  length = 19
FEATURE                Location/Qualifiers
misc_feature           1..19
                       note = Synthetic Primer Sequence
source                 1..19
                       mol_type = other DNA
                       organism = synthetic construct
SEQUENCE: 7
gatgtatgaa ggctttggt                                                   19

SEQ ID NO: 8           moltype = DNA  length = 20
FEATURE                Location/Qualifiers
misc_feature           1..20
                       note = Synthetic Primer Sequence
source                 1..20
                       mol_type = other DNA
                       organism = synthetic construct
SEQUENCE: 8
tgtgcacttt tattggtgtg                                                  20
```

TELOMERASE ACTIVATING COMPOUNDS FOR USE IN FERTILITY AND RELATED APPLICATIONS

CROSS-REFERENCE TO RELATED APPLICATIONS

The present application is a continuation of U.S. patent application Ser. No. 16/485,416, filed Feb. 27, 2020, which is a national stage entry of International Patent Application Number PCT/IL2018/050161, filed Feb. 12, 2018, which claims the benefit of Israel Patent Application Number 250567, filed Feb. 12, 2017, and U.S. Provisional Application No. 62/458,028 filed Feb. 13, 2017 and Israel Patent Application Number 257470, Filed Feb. 11, 2018, all of which are incorporated by reference in their entirety.

REFERENCE TO A SEQUENCE LISTING

The present application includes an electronic sequence listing in a file named "599571_SEQListing.xml," created Aug. 25, 2023, and containing 11,275 bytes, which is incorporated by reference.

FIELD OF THE INVENTION

The present invention is directed to use of a series of compounds and compositions comprising the same for treating diseases, disorders and/or conditions related to fertility and preserving same and conditions related to same.

BACKGROUND OF THE INVENTION

Telomerase is a ribonucleoprotein responsible for the elongation of repetitive DNA structure in the chromosome ends of eukaryotes—the Telomeres, which shorten every cell division due to the "end replication problem". Telomerase is composed of two major subunits, the catalytic subunit telomerase reverse transcriptase (TERT) and an RNA component (TR) which serves as a template for telomere elongation. Telomerase expression is essential for proliferative cells. One of the major genetic mechanisms determining cell proliferative capacity is the maintenance of telomeres by the enzyme telomerase.

Telomerase activity has been detected in human germ cells, such as in the ovary and expressed in intensively dividing cells and tissues which have the capacity of regeneration. Decrease in fertility among TERT deficient animal models and TR deficient female mice have shown uterine atrophy, which indicates dysfunction of granulosa cells. During the development of oocytes, folliculogenesis is accompanied by significant proliferation of granulosa cells.

Most somatic cells contain low or undedicated expression of telomerase but during the spermatogenesis process telomerase is active and its catalytic subunit TERT is expressed, as well.

Beyond the above, little is known about the role of telomerase and its subunits in developing gonads, for example, in oocytes and granulosa cells or in spermatogenesis. Still less is understood in terms of the differential impact of telomerase activating compounds and treatment or recovery of fertility.

SUMMARY OF THE INVENTION

In one embodiment, this invention provides a method of promoting, improving, recovering or restoring fertility in a subject in need thereof, comprising contacting a gonadal or fertility-associated cell or tissue with a compound represented by the structure of formula I:

I

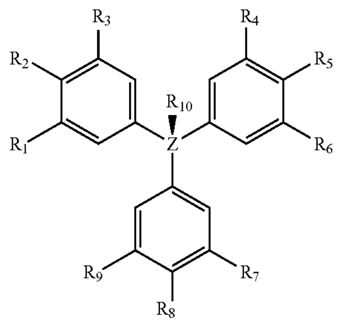

wherein

Z is carbon, nitrogen, phosphor, arsenic, silicon or germanium;

$R_1$ to $R_9$ are the same or different, H, D, OH, halogen, nitro, CN, nitrileamido, amidosulfide, amino, aldehyde, substituted ketone, —COOH, ester, trifluoromethyl, amide, substituted or unsubstituted alkyl, alkenyl, alkynyl, aryl, arylalkyl, alkylaryl, arylsulfonyl, arylalkylenesulfonyl, alkoxy, alkylalkoxy, haloalkyl, alkylhaloalkyl, haloaryl, aryloxy, amino, monoalkylamino, dialkylamino, alkylamido, arylamino, arylamido, alkylthio, arylthio, heterocycloalkyl, alkylheterocycloalkyl, heterocycloalkylalkyl, heteroaryl, hetroarylalkyl, alkylheteroaryl; or $R_3$, $R_4$, or $R_7$, forms a fused cycloalkyl, heterocycloalkyl, aromatic or heteroaromatic ring with the main aromatic ring; and $R_{10}$ is nothing, H, D, OH, halogen, oxo, nitro, CN, nitrileamido, amidosulfide, amino, aldehyde, substituted ketone, —COOH, ester, trifluoromethyl, amide, substituted or unsubstituted alkyl, alkenyl, alkynyl, aryl, arylalkyl, alkylaryl, arylsulfonyl, arylalkylenesulfonyl, alkoxy, haloalkyl, haloaryl, cycloalkyl, alkylcycloalkyl, aryloxy, monoalkylamino, dialkylamino, alkylamido, arylamino, arylamido, alkylthio, arylthio, heterocycloalkyl, alkylheterocycloalkyl, heterocycloalkylalkyl, heteroaryl, hetroarylalkyl, alkylheteroaryl; or its isomer, pharmaceutically acceptable salt, pharmaceutical product, hydrate, N-oxide, crystal or any combination thereof.

In some embodiments, this invention provides for the use of a compound represented by the structure of formula I:

I

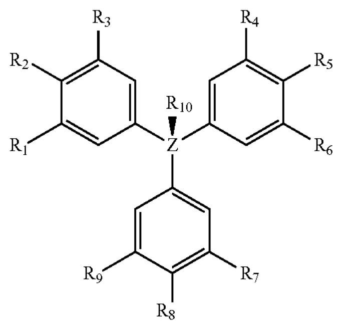

wherein

Z is carbon, nitrogen, phosphor, arsenic, silicon or germanium;

$R_1$ to $R_9$ are the same or different, H, D, OH, halogen, nitro, CN, nitrileamido, amidosulfide, amino, aldehyde, substituted ketone, —COOH, ester, trifluoromethyl, amide, substituted or unsubstituted alkyl, alkenyl, alkynyl, aryl, arylalkyl, alkylaryl, arylsulfonyl, arylalkylenesulfonyl, alkoxy, alkylalkoxy, haloalkyl, alkylhaloalkyl, haloaryl, aryloxy, amino, monoalkylamino, dialkylamino, alkylamido, arylamino, arylamido, alkylthio, arylthio, heterocycloalkyl, alkylheterocycloalkyl, heterocycloalkylalkyl, heteroaryl, hetroarylalkyl, alkylheteroaryl; or $R_3$, $R_4$, or $R_7$, forms a fused cycloalkyl, heterocycloalkyl, aromatic or heteroaromatic ring with the main aromatic ring; and $R_{10}$ is nothing, H, D, OH, halogen, oxo, nitro, CN, nitrileamido, amidosulfide, amino, aldehyde, substituted ketone, —COOH, ester, trifluoromethyl, amide, substituted or unsubstituted alkyl, alkenyl, alkynyl, aryl, arylalkyl, alkylaryl, arylsulfonyl, arylalkylenesulfonyl, alkoxy, haloalkyl, haloaryl, cycloalkyl, alkylcycloalkyl, aryloxy, monoalkylamino, dialkylamino, alkylamido, arylamino, arylamido, alkylthio, arylthio, heterocycloalkyl, alkylheterocycloalkyl, heterocycloalkylalkyl, heteroaryl, hetroarylalkyl, alkylheteroaryl; or its isomer, pharmaceutically acceptable salt, pharmaceutical product, hydrate, N-oxide, crystal or any combination thereof for promoting, improving, recovering or restoring fertility in a subject in need thereof.

According to these aspects and in some embodiments, such method and/or use promoting, improving, recovering or restoring fertility in a subject beneficially modulates gonadotropin expression or steroid hormone expression in terms of timing or quantity or a combination thereof, or in some embodiments, improves follicle maturation in terms of timing or quantity or a combination thereof, or in some embodiments, improves sperm quantity, quality, motility or a combination thereof, or any combination of same.

In other embodiments, this invention provides a method of promoting, improving, recovering or restoring function to gonadal cells or tissues in a subject in need thereof, comprising contacting a gonadal or fertility-associated cell or tissue with a compound represented by the structure of formula I:

I

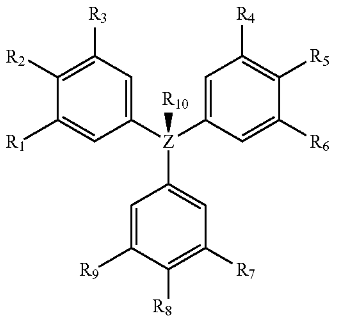

wherein

Z is carbon, nitrogen, phosphor, arsenic, silicon or germanium;

$R_1$ to $R_9$ are the same or different, H, D, OH, halogen, nitro, CN, nitrileamido, amidosulfide, amino, aldehyde, substituted ketone, —COOH, ester, trifluoromethyl, amide, substituted or unsubstituted alkyl, alkenyl, alkynyl, aryl, arylalkyl, alkylaryl, arylsulfonyl, arylalkylenesulfonyl, alkoxy, alkylalkoxy, haloalkyl, alkylhaloalkyl, haloaryl, aryloxy, amino, monoalkylamino, dialkylamino, alkylamido, arylamino, arylamido, alkylthio, arylthio, heterocycloalkyl, alkylheterocycloalkyl, heterocycloalkylalkyl, heteroaryl, hetroarylalkyl, alkylheteroaryl; or $R_3$, $R_4$, or $R_7$, forms a fused cycloalkyl, heterocycloalkyl, aromatic or heteroaromatic ring with the main aromatic ring; and $R_{10}$ is nothing, H, D, OH, halogen, oxo, nitro, CN, nitrileamido, amidosulfide, amino, aldehyde, substituted ketone, —COOH, ester, trifluoromethyl, amide, substituted or unsubstituted alkyl, alkenyl, alkynyl, aryl, arylalkyl, alkylaryl, arylsulfonyl, arylalkylenesulfonyl, alkoxy, haloalkyl, haloaryl, cycloalkyl, alkylcycloalkyl, aryloxy, monoalkylamino, dialkylamino, alkylamido, arylamino, arylamido, alkylthio, arylthio, heterocycloalkyl, alkylheterocycloalkyl, heterocycloalkylalkyl, heteroaryl, hetroarylalkyl, alkylheteroaryl; or its isomer, pharmaceutically acceptable salt, pharmaceutical product, hydrate, N-oxide, crystal or any combination thereof.

In other embodiments, this invention provides for the use of a compound represented by the structure of formula I:

I

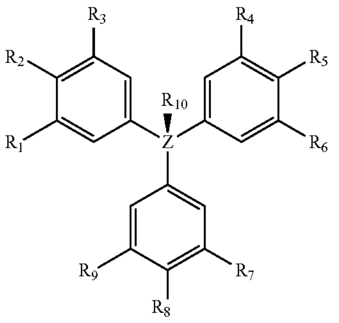

wherein

Z is carbon, nitrogen, phosphor, arsenic, silicon or germanium;

$R_1$ to $R_9$ are the same or different, H, D, OH, halogen, nitro, CN, nitrileamido, amidosulfide, amino, aldehyde, substituted ketone, —COOH, ester, trifluoromethyl, amide, substituted or unsubstituted alkyl, alkenyl, alkynyl, aryl, arylalkyl, alkylaryl, arylsulfonyl, arylalkylenesulfonyl, alkoxy, alkylalkoxy, haloalkyl, alkylhaloalkyl, haloaryl, aryloxy, amino, monoalkylamino, dialkylamino, alkylamido, arylamino, arylamido, alkylthio, arylthio, heterocycloalkyl, alkylheterocycloalkyl, heterocycloalkylalkyl, heteroaryl, hetroarylalkyl, alkylheteroaryl; or $R_3$, $R_4$, or $R_7$, forms a fused cycloalkyl, heterocycloalkyl, aromatic or heteroaromatic ring with the main aromatic ring; and $R_{10}$ is nothing, H, D, OH, halogen, oxo, nitro, CN, nitrileamido, amidosulfide, amino, aldehyde, substituted ketone, —COOH, ester, trifluoromethyl, amide, substituted or unsubstituted alkyl, alkenyl, alkynyl, aryl, arylalkyl, alkylaryl, arylsulfonyl, arylalkylenesulfonyl, alkoxy, haloalkyl, haloaryl, cycloalkyl, alkylcycloalkyl, aryloxy, monoalkylamino, dialkylamino, alkylamido, arylamino, arylamido, alkylthio, arylthio, heterocycloalkyl, alkylheterocycloalkyl, heterocycloalkylalkyl, heteroaryl, hetroarylalkyl, alkylheteroaryl; or its isomer, pharmaceutically acceptable salt, pharmaceutical product, hydrate, N-oxide, crystal or any combination thereof for promoting, improving, recovering or restoring function to gonadal cells or tissues in a subject in need thereof.

In some embodiments, this invention provides for a method of promoting, enhancing or improving fertility-associated cell or tissue yield as part of an in vitro fertilization protocol, comprising contacting said fertility-associated cell or tissue with a compound represented by the structure of formula 1:

I

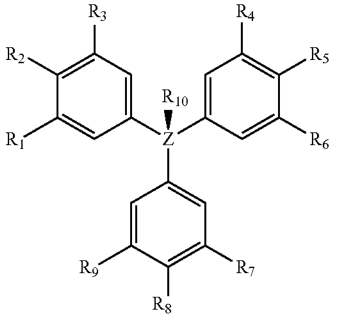

wherein

Z is carbon, nitrogen, phosphor, arsenic, silicon or germanium;

$R_1$ to $R_9$ are the same or different, H, D, OH, halogen, nitro, CN, nitrileamido, amidosulfide, amino, aldehyde, substituted ketone, —COOH, ester, trifluoromethyl, amide, substituted or unsubstituted alkyl, alkenyl, alkynyl, aryl, arylalkyl, alkylaryl, arylsulfonyl, arylalkylenesulfonyl, alkoxy, alkylalkoxy, haloalkyl, alkylhaloalkyl, haloaryl, aryloxy, amino, monoalkylamino, dialkylamino, alkylamido, arylamino, arylamido, alkylthio, arylthio, heterocycloalkyl, alkylheterocycloalkyl, heterocycloalkylalkyl, heteroaryl, hetroarylalkyl, alkylheteroaryl; or $R_3$, $R_4$, or $R_7$, forms a fused cycloalkyl, heterocycloalkyl, aromatic or heteroaromatic ring with the main aromatic ring; and $R_{10}$ is nothing, H, D, OH, halogen, oxo, nitro, CN, nitrileamido, amidosulfide, amino, aldehyde, substituted ketone, —COOH, ester, trifluoromethyl, amide, substituted or unsubstituted alkyl, alkenyl, alkynyl, aryl, arylalkyl, alkylaryl, arylsulfonyl, arylalkylenesulfonyl, alkoxy, haloalkyl, haloaryl, cycloalkyl, alkylcycloalkyl, aryloxy, monoalkylamino, dialkylamino, alkylamido, arylamino, arylamido, alkylthio, arylthio, heterocycloalkyl, alkylheterocycloalkyl, heterocycloalkylalkyl, heteroaryl, hetroarylalkyl, alkylheteroaryl; or its isomer, pharmaceutically acceptable salt, pharmaceutical product, hydrate, N-oxide, crystal or any combination thereof.

In still other embodiments, this invention provides for the use of a compound represented by the structure of formula I:

I

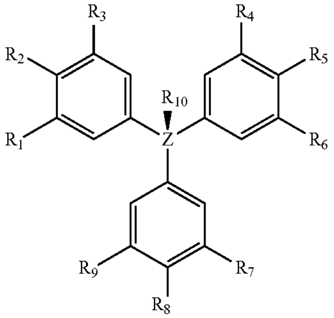

wherein

Z is carbon, nitrogen, phosphor, arsenic, silicon or germanium;

$R_1$ to $R_9$ are the same or different, H, D, OH, halogen, nitro, CN, nitrileamido, amidosulfide, amino, aldehyde, substituted ketone, —COOH, ester, trifluoromethyl, amide, substituted or unsubstituted alkyl, alkenyl, alkynyl, aryl, arylalkyl, alkylaryl, arylsulfonyl, arylalkylenesulfonyl, alkoxy, alkylalkoxy, haloalkyl, alkylhaloalkyl, haloaryl, aryloxy, amino, monoalkylamino, dialkylamino, alkylamido, arylamino, arylamido, alkylthio, arylthio, heterocycloalkyl, alkylheterocycloalkyl, heterocycloalkylalkyl, heteroaryl, hetroarylalkyl, alkylheteroaryl; or $R_3$, $R_4$, or $R_7$, forms a fused cycloalkyl, heterocycloalkyl, aromatic or heteroaromatic ring with the main aromatic ring; and $R_{10}$ is nothing, H, D, OH, halogen, oxo, nitro, CN, nitrileamido, amidosulfide, amino, aldehyde, substituted ketone, —COOH, ester, trifluoromethyl, amide, substituted or unsubstituted alkyl, alkenyl, alkynyl, aryl, arylalkyl, alkylaryl, arylsulfonyl, arylalkylenesulfonyl, alkoxy, haloalkyl, haloaryl, cycloalkyl, alkylcycloalkyl, aryloxy, monoalkylamino, dialkylamino, alkylamido, arylamino, arylamido, alkylthio, arylthio, heterocycloalkyl, alkylheterocycloalkyl, heterocycloalkylalkyl, heteroaryl, hetroarylalkyl, alkylheteroaryl; or its isomer, pharmaceutically acceptable salt, pharmaceutical product, hydrate, N-oxide, crystal or any combination thereof for promoting, enhancing or improving fertility-associated cell or tissue yield as part of an in vitro fertilization protocol.

In one embodiment the structure of formula I is represented by the structure of formula IV:

IV

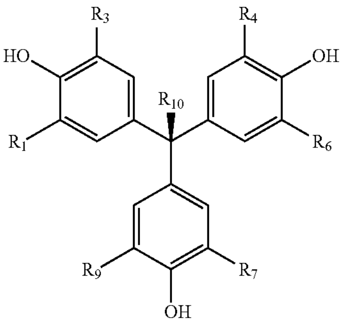

wherein $R_1$, $R_3$, $R_4$, $R_6$, $R_7$, $R_9$ and $R_{10}$ are as described above.

In another embodiment the structure of formula I is represented by the structure of formula VI:

VI

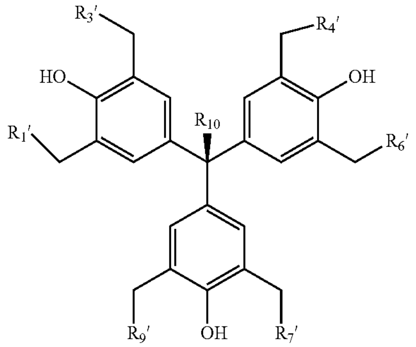

wherein $R_1'$, $R_3'$, Ra', $R_6'$, $R_7'$, and $R_9'$ are the same or different comprising halogen, aryl, alkyl, cycloalkyl, heterocycloalkyl, alkoxy, monoalkylamino, dialkylamino or arylamino; and $R_{10}$ is as described above.

In another embodiment the structure of formula I is represented by the structure of formula VII:

VII

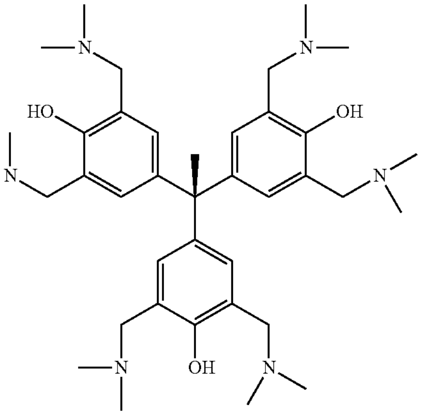

In another embodiment the structure of formula I is represented by the structure of formula VIII:

VIII

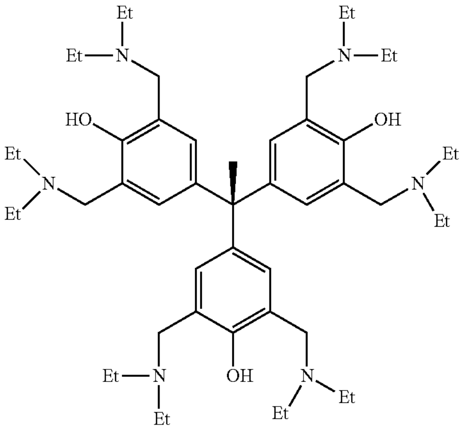

In another embodiment the structure of formula I is represented by the structure of formula IX:

IX

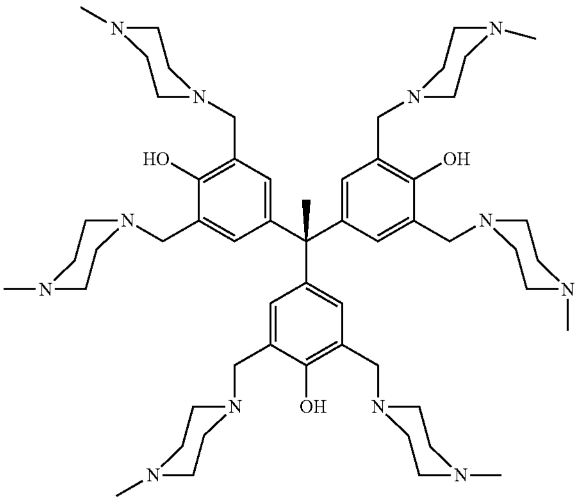

In another embodiment the structure of formula I is represented by the structure of formula X:

X

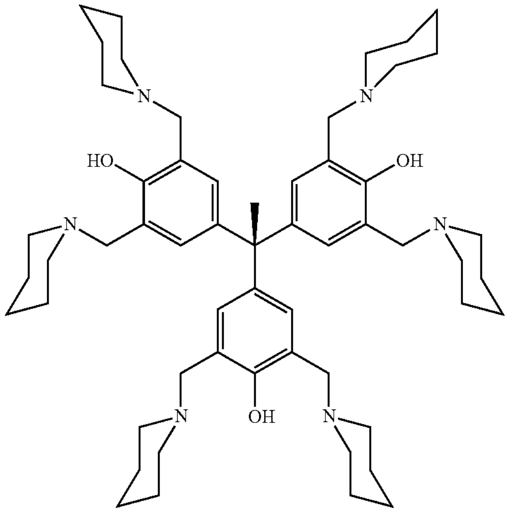

In another embodiment the structure of formula I is represented by the structure of formula XI:

XI

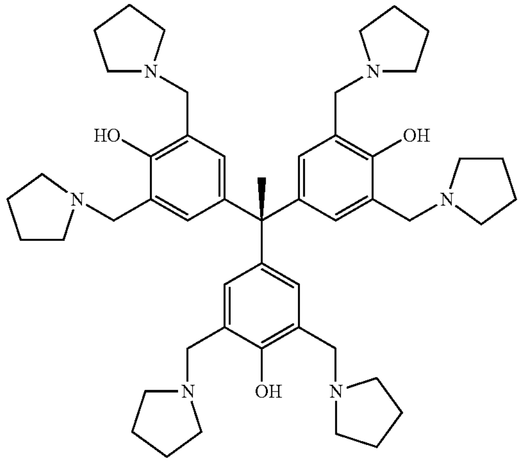

In another embodiment the structure of formula I is represented by the structure of formula XII:

XII

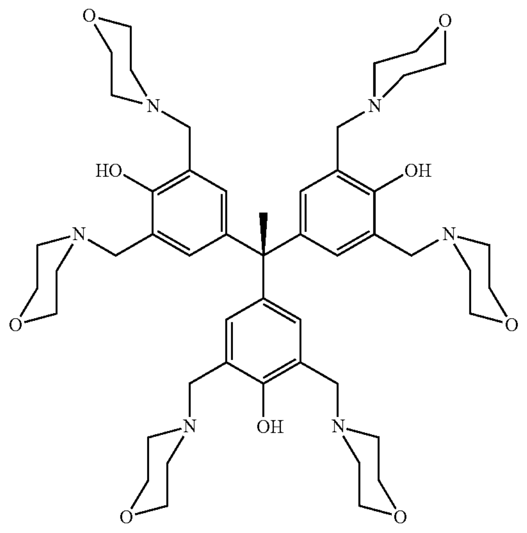

In another embodiment the structure of formula I is represented by the structure of formula XIII:

XIII

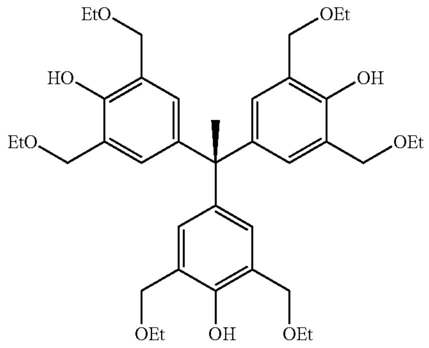

In another embodiment the structure of formula I is represented by the structure of formula XIV:

XIV

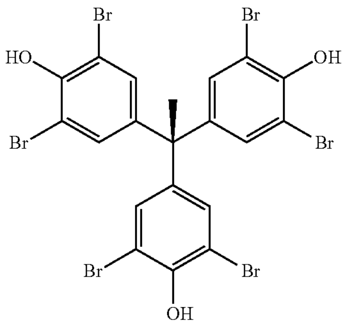

In another embodiment the structure of formula I is represented by the structure of formula XV:

XV

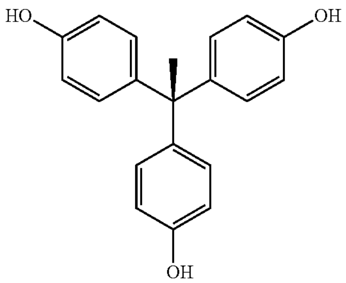

In another embodiment the structure of formula I is represented by the structure of formula XVI:

XVI

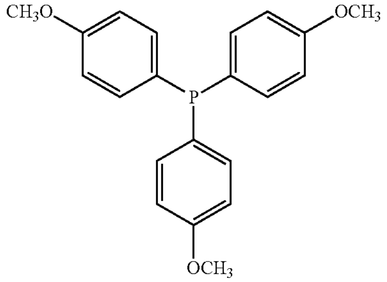

In another embodiment, the invention makes use of pharmaceutical compositions comprising compounds as described herein for any method as described herein.

In some embodiments, this invention particularly contemplates methods or uses including use of the following compounds:

Compound 68

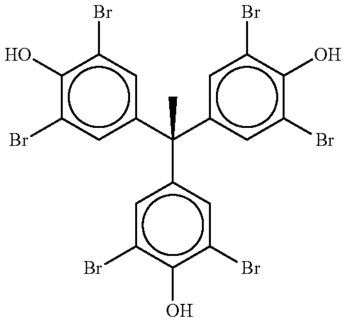

1,1,1-tris (4-hydroxy-3,5-dibromo-phenyl)-ethane

-continued

Compound 70

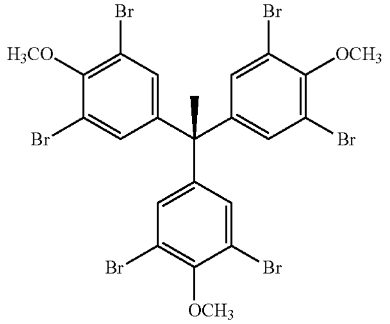

$C_{23}H_{18}Br_6O_3$
Mol. Wt.: 821.81

Compound 79

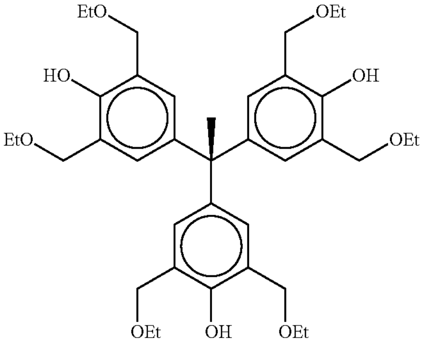

1,1,1-tris (4-hydroxy-3,5-methylene ethoxy-phenyl)-ethane or any combination of such compounds, and methods/uses employing any of such compounds is to be considered an embodiment of this invention.

In some aspects, the compounds as herein described are suitable for administration to a female subject, to specifically promote and/or enhance ovulation. In some aspects, such use may, inter alia, include use of Compound 79 and Compound 68 and Compound 70. According to this aspect and in some embodiments, such treatment may increase the number and/or quality of ovum that ultimately can be fertilized in situ.

In some aspects, the compounds as herein described are suitable for administration to a female subject, to specifically enhance the quality and/or number of ovum appropriate for retrieval for an in vitro fertilization or harvest procedure. In some aspects, such use may, inter alia, include use of Compound 79 and Compound 68 and Compound 70.

In some aspects, Compound 79 particularly and unexpectedly outperforms other compounds in terms of promoting/enhancing ovulation promoting events.

In some aspects, the compounds as herein described are suitable for administration to a female subject, to specifically protect or promote recovered ovum quality and/or quantity following exposure of such subject to irradiation.

In some aspects, the compounds as herein described promote or enhance fertilization events in situ or in vitro.

In some aspects, the compounds as herein described are suitable for administration to a male subject, to specifically enhance the quality and/or number of sperm for applications in fertilization in situ or in vitro. In some aspects the compounds as herein described may promote enhanced sperm capacitance, maturity, number, quality, motility or a combination of same.

In some aspects, the compounds as herein described are suitable for administration to a male subject, to specifically protect or promote recovered sperm fertilization capacity following exposure of such subject to irradiation or as a result of aging or premature aging in a subject.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

(FIG. 12A) Female mice at the various estrous stages were injected s.c. with DMSO, Compound 79 or 68. After 12 hours the mice were sacrificed and the ovaries were removed and weighted. The results are means±SE, n>6 ovaries per group.

(FIG. 13A). Before treatment proestrus stages (FIG. 13A), estrus stages (FIG. 13C). After 12 hours of treatment the vaginal smears were taken again, proestrus stages (FIG. 13B), estrus stages (FIG. 13D). The vaginal smears were stained by crystal violet.

(FIG. 16A) P+12h, (FIG. 16B) E+12h, (FIG. 16C) M+12h, (FIG. 16D) D+12h.

FIG. 19(A) (WC: p=0.01, DB: p=0.42) n=9 for high, n=12 for low, average enzyme activities of telo (in WC and DB extracts) were calculated for high and low estrogen levels. High estrogen level was determined as ≤1500 ng/ml.

FIG. 20A-topoisomerase average activity (p=0.159).

FIG. 21A-Telomerase expression was calculated as % of the total protein expression with correlation to blood estrogen levels.

FIG. 26B provides a light micrograph showing healthy and defective sperm head morphology observed. The arrows labeled 1 and 2 point to defective sperm head morphology, and the arrows labeled 3 and 4 point to healthy sperm head morphology

DETAILED DESCRIPTION OF THE PRESENT INVENTION

Figure 1:
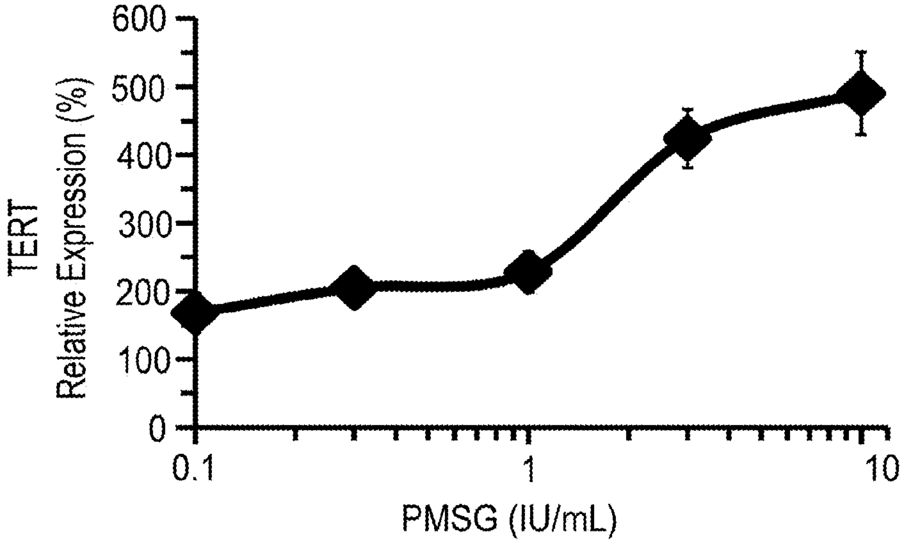
FIG. 1: plots granulosa cells treated with different concentrations of PMSG for 6 hours. RNA extract served for TERT relative mRNA levels measurement by qRT-PCR with specific primers for TERT and β-actin as a reference gene. Results represents average+SE(n=3).

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

The present invention relates, in some embodiments, to the use of a novel class of tri-phenyl compounds and compositions comprising the same for the treatment of, inter alia, fertility-related or infertility-related diseases or conditions capable of being affected by enhanced telomerase expression and/or telomerase activation.

In some aspects, the invention makes use of such compounds which stimulate and/or increase telomerase expression and/or activity in the gonadal or fertility related cells and tissues of a subject, where the activity is decreased, missing, altered or normal. Such disorders include, inter alia, a) fertility-related impairment, including impairment of tissue turnover, which occur with cancer or cancer therapy, b) luteal phase defect; c) premature ovarian failure (primary ovarian insufficiency or hypergonadotropic hypogonadism); and/or d) increasing telomerase expression and/or activity in gonadal or fertility-associated healthy tissue, thus promoting or restoring fertility in the subject. In some aspects, the subject has been exposed to radiation.

In some aspects, the compounds as herein described are suitable for administration to a female subject, to specifically promote and/or enhance ovulation. In some aspects, such use may include use of any compound as herein described. According to this aspect and in some embodiments, such treatment may increase the number and/or quality of ovum that ultimately can be fertilized in situ.

In some aspects, the compounds as herein described are suitable for administration to a female subject, to specifically enhance the quality and/or number of ovum appropriate for retrieval for an in vitro fertilization or harvest procedure. In some aspects, such use may, inter alia, include use of any compound as herein described.

In some aspects, certain compounds as herein described particularly and unexpectedly outperform other compounds in terms of promoting/enhancing ovulation promoting events.

In some aspects, the compounds as herein described are suitable for administration to a female subject, to specifically protect or promote recovered ovum quality and/or quantity following exposure of such subject to irradiation.

In some aspects, the compounds as herein described promote or enhance fertilization events in situ or in vitro.

In some aspects, the compounds as herein described are suitable for administration to a male subject, to specifically enhance the quality and/or number of sperm for applications in fertilization in situ or in vitro. In some aspects the compounds as herein described may promote enhanced sperm capacitance, maturity, number, quality, motility or a combination of same.

Compounds of the Invention:

In one embodiment, the methods of this invention comprise the use of tri-phenyl compounds represented by the structure of formula I:

I

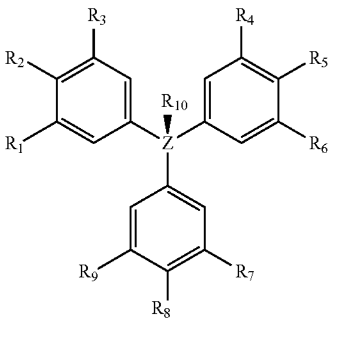

wherein

Z is carbon, nitrogen, phosphor, arsenic, silicon or germanium;

$R_1$ to $R_9$ are the same or different, H, D, OH, halogen, nitro, CN, nitrileamido, amidosulfide, amino, aldehyde, substituted ketone, —COOH, ester, trifluoromethyl, amide, substituted or unsubstituted alkyl, alkenyl, alkynyl, aryl, arylalkyl, alkylaryl, arylsulfonyl, arylalkylenesulfonyl, alkoxy, alkylalkoxy, haloalkyl, alkylhaloalkyl, haloaryl, aryloxy, amino, monoalkylamino, dialkylamino, alkylamido, arylamino, arylamido, alkylthio, arylthio, heterocycloalkyl, alkylheterocycloalkyl, heterocycloalkylalkyl, heteroaryl, hetroarylalkyl, alkylheteroaryl; or $R_3$, $R_4$, or $R_7$, forms a fused cycloalkyl, heterocycloalkyl, aromatic or heteroaromatic ring with the main aromatic ring; and $R_{10}$ is nothing, H, D, OH, halogen, oxo, nitro, CN, nitrileamido, amidosulfide, amino, aldehyde, substituted ketone, —COOH, ester, trifluoromethyl, amide, substituted or unsubstituted alkyl, alkenyl, alkynyl, aryl, arylalkyl, alkylaryl, arylsulfonyl, arylalkylenesulfonyl, alkoxy, haloalkyl, haloaryl, cycloalkyl, alkylcycloalkyl, aryloxy, monoalkylamino, dialkylamino, alkylamido, arylamino, arylamido, alkylthio, arylthio, heterocycloalkyl, alkylheterocycloalkyl, heterocycloalkylalkyl, heteroaryl, hetroarylalkyl, alkylheteroaryl; or its isomer, pharmaceutically acceptable salt, pharmaceutical product, hydrate, N-oxide, crystal or any combination thereof, and compositions comprising the same.

In one embodiment, the methods of this invention comprise the use of tri-phenyl compounds represented by the structure of formula II:

II

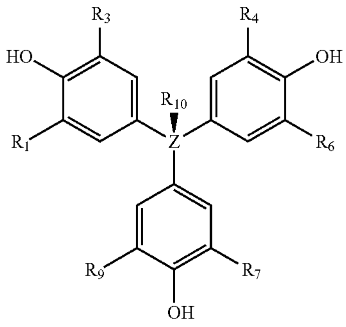

wherein

Z is carbon, nitrogen, phosphor, arsenic, silicon or germanium;

$R_1$, $R_3$, $R_4$, $R_6$, Rz and Ry are the same or different, H, D, OH, halogen, nitro, CN, nitrileamido, amidosulfide, amino, aldehyde, substituted ketone, —COOH, ester, trifluoromethyl, amide, substituted or unsubstituted alkyl, alkenyl, alkynyl, aryl, arylalkyl, alkylaryl, arylsulfonyl, arylalkylenesulfonyl, alkoxy, alkylalkoxy, haloalkyl, alkylhaloalkyl, haloaryl, aryloxy, amino, monoalkylamino, dialkylamino, alkylamido, arylamino, arylamido, alkylthio, arylthio, heterocycloalkyl, alkylheterocycloalkyl, heterocycloalkylalkyl, heteroaryl, hetroarylalkyl, alkylheteroaryl; or $R_3$, $R_4$, or $R_7$, forms a fused cycloalkyl, heterocycloalkyl, aromatic or heteroaromatic ring with the main aromatic ring; and $R_{10}$ is nothing, H, D, OH, halogen, oxo, nitro, CN, nitrileamido, amidosulfide, amino, aldehyde, substituted ketone, —COOH, ester, trifluoromethyl, amide, substituted or unsubstituted alkyl, alkenyl, alkynyl, aryl, arylalkyl, alkylaryl, arylsulfonyl, arylalkylenesulfonyl, alkoxy, haloalkyl, haloaryl, cycloalkyl, alkylcycloalkyl, aryloxy, monoalkylamino, dialkylamino, alkylamido, arylamino, arylamido, alkylthio, arylthio, heterocycloalkyl, alkylheterocycloalkyl, heterocycloalkylalkyl, heteroaryl, hetroarylalkyl, alkylheteroaryl; or its isomer, pharmaceutically acceptable salt, pharmaceutical product, hydrate, N-oxide, crystal or any combination thereof, and compositions comprising the same.

In one embodiment Z is carbon. In another embodiment $R_{10}$ is a methyl group. In another embodiment $R_1$, $R_3$, $R_4$, $R_6$, $R_7$, and $R_9$ are $-(CH_2)_n$-heterocycloalkyl group, wherein n is between 1-6. In another embodiment $R_1$, $R_3$, $R_4$, $R_6$, $R_7$, and $R_9$ are $-(CH_2)$-aminoalkyl group, wherein n is between 1-6. In another embodiment $R_1$, $R_3$, $R_4$, $R_6$, $R_7$, and $R_9$ are $-(CH_2)_n$-dialkylamino group, wherein n is between 1-6 In another embodiment $R_1$, $R_3$, $R_4$, $R_6$, $R_7$, and $R_9$ are $-(CH_2)_n-N(CH_3)_2$ group, wherein n is between 1-6. In another embodiment $R_1$, $R_3$, $R_4$, $R_6$, $R_7$, and $R_9$ are $-(CH_2)_n-N(Et)_2$ group, wherein n is between 1-6. In another embodiment $R_1$, $R_3$, $R_4$, $R_6$, $R_7$, and $R_9$ are $-(CH_2)_n$-aryl group, wherein n is between 1-6. In another embodiment $R_1$, $R_3$, $R_4$, $R_6$, $R_7$, and $R_9$ are $-(CH_2)_n$-heteroaryl group, wherein n is between 1-6. In another embodiment $R_1$, $R_3$, $R_4$, $R_6$, $R_7$, and $R_9$ are $-(CH_2)_n$-haloalkyl group, wherein n is between 1-6. In another embodiment $R_1$, $R_3$, $R_4$, $R_6$, $R_7$, and Ry are $-(CH_2)_n$-alkoxy group, wherein n is between 1-6. In another embodiment $R_1$, $R_3$, $R_4$, $R_6$, $R_7$, and $R_9$ are $-(CH_2)_n$-ethoxy group, wherein n is between 1-6. In another embodiment $R_1$, $R_3$, $R_4$, $R_6$, $R_7$, and $R_9$ are $-(CH_2)_n$-cycloalkyl group, wherein n is between 1-6.

In one embodiment, the methods of this invention comprise the use of tri-phenyl compounds represented by the structure of formula III:

III

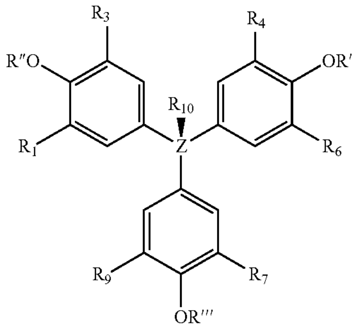

wherein

Z is carbon, nitrogen, phosphor, arsenic, silicon or germanium;

R', R" and R'" are independently the same or different comprising hydrogen, alkyl, haloalkyl, alkylamino, phenyl, benzyl, alkanyloyl, acetyl or benzoyl;

$R_1$, $R_3$, $R_4$, $R_6$, $R_7$ and $R_9$ are the same or different, H, D, OH, halogen, nitro, CN, nitrileamido, amidosulfide, amino, aldehyde, substituted ketone, —COOH, ester, trifluoromethyl, amide, substituted or unsubstituted alkyl, alkenyl, alkynyl, aryl, arylalkyl, alkylaryl, arylsulfonyl, arylalkylenesulfonyl, alkoxy, alkylalkoxy, haloalkyl, alkylhaloalkyl, haloaryl, aryloxy, amino, monoalkylamino, diaikylamino, alkylamido, arylamino, arylamido, alkylthio, arylthio, heterocycloalkyl, alkylheterocycloalkyl, heterocycloalkylalkyl, heteroaryl, hetroarylalkyl, alkylheteroaryl; or $R_3$, $R_4$, or $R_7$, forms a fused cycloalkyl, heterocycloalkyl, aromatic or heteroaromatic ring with the main aromatic ring; and $R_{10}$ is nothing, H, D, OH, halogen, oxo, nitro, CN, nitrileamido, amidosulfide, amino, aldehyde, substituted ketone, —COOH, ester, trifluoromethyl, amide, substituted or unsubstituted alkyl, alkenyl, alkynyl, aryl, arylalkyl, alkylaryl, arylsulfonyl, arylalkylenesulfonyl, alkoxy, haloalkyl, haloaryl, cycloalkyl, alkylcycloalkyl, aryloxy, monoalkylamino, dialkylamino, alkylamido, arylamino, arylamido, alkylthio, arylthio, heterocycloalkyl, alkylheterocycloalkyl, heterocycloalkylalkyl, heteroaryl, hetroarylalkyl, alkylheteroaryl; or its isomer, pharmaceutically acceptable salt, pharmaceutical product, hydrate, N-oxide, crystal or any combination thereof, and compositions comprising the same.

In one embodiment, the methods of this invention comprise the use of tri-phenyl compounds represented by the structure of formula IV:

IV

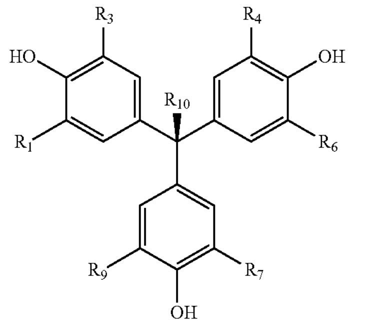

wherein $R_1$, $R_3$, $R_4$, $R_6$, $R_7$, $R_9$ and $R_{10}$ are as defined above; or its isomer, pharmaceutically acceptable salt, pharmaceutical product, hydrate, N-oxide, crystal or any combination thereof, and compositions comprising the same.

In one embodiment, the methods of this invention comprise the use of tri-phenyl compounds represented by the structure of formula V:

V

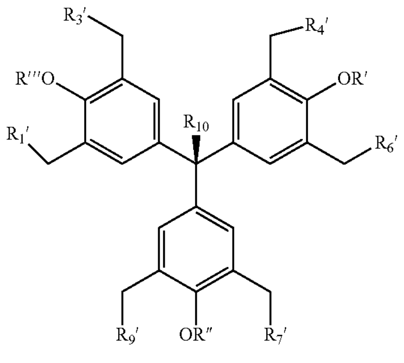

wherein

R', R", R'" are independently the same or different comprising hydrogen, alkyl, haloalkyl, phenyl, benzyl, alkanyloyl, acetyl or benzoyl;

$R_1$', $R_3$', $R_4$', $R_6$' $R_7$', and $R_9$' are the same or different comprising halogen, aryl, alkyl, cycloalkyl, heterocycloalkyl, alkoxy, amino, monoalkylamino, dialkylamino or arylamino group; and Rz is as described above; or its isomer, pharmaceutically acceptable salt, pharmaceutical product, hydrate, N-oxide, crystal or any combination thereof, and compositions comprising the same.

In one embodiment, $R_1$', $R_3$', $R_4$', $R_6$' $R_7$', and $R_9$' are dialkylamino group. In another embodiment, $R_1$', $R_3$', $R_4$', $R_6$' $R_7$', and $R_8$' are dimethylamino group. In another embodiment, $R_1$', $R_3$', $R_4$', $R_6$' $R_7$', and $R_9$' are diethylamino group. In another embodiment, $R_1$', $R_3$', $R_4$', $R_6$' $R_7$', and Ry' are N-piperidine group. In another embodiment, $R_1$', $R_3$', $R_4$', $R_6$' $R_7$', and $R_9$' are N-pyrolidine group. In another embodiment, $R_1$', $R_3$', $R_4$', $R_6$' $R_7$', and $R_9$' are N-piperazine group. In another embodiment, $R_1$', $R_3$', $R_4$', $R_6$' $R_7$', and $R_9$' are N-piperazine-4-methyl group. In another embodiment, $R_1$', $R_3$', $R_4$', $R_6$' $R_7$', and $R_9$' are N-morpholine group. In another embodiment, $R_1$', $R_3$', $R_4$', $R_9$' Ry', and $R_9$' are ethoxy group.

In one embodiment, the methods of this invention comprise the use of tri-phenyl compounds represented by the structure of formula VI:

VI

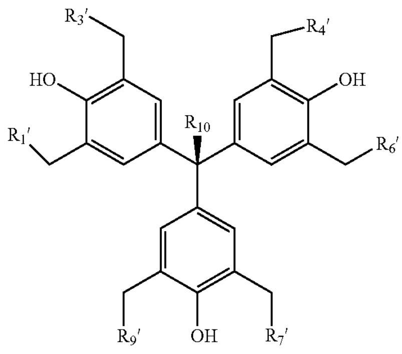

wherein $R_1$', $R_3$', $R_4$', $R_6$' $R_7$', and $R_9$' are the same or different comprising halogen, aryl, alkyl, cycloalkyl, heterocycloalkyl, alkoxy, amino, monoalkylamino, dialkylamino or arylamino group; and Rio is as described above; or its isomer, pharmaceutically acceptable salt, pharmaceutical product, hydrate, N-oxide, crystal or any combination thereof, and compositions comprising the same.

In one embodiment, the methods of this invention comprise the use of tri-phenyl compounds represented by the structure of formula VII:

VII

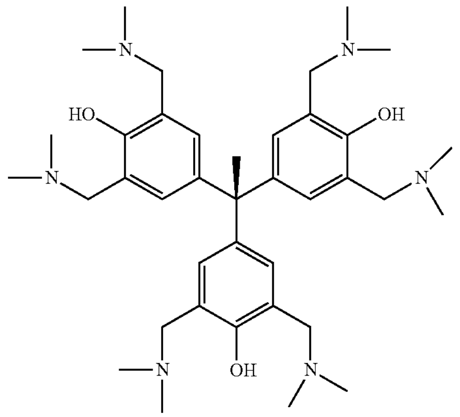

or its isomer, pharmaceutically acceptable salt, pharmaceutical product, hydrate, N-oxide, crystal or any combination thereof, and compositions comprising the same.

In one embodiment, the methods of this invention comprise the use of tri-phenyl compounds represented by the structure of formula VIII:

VIII

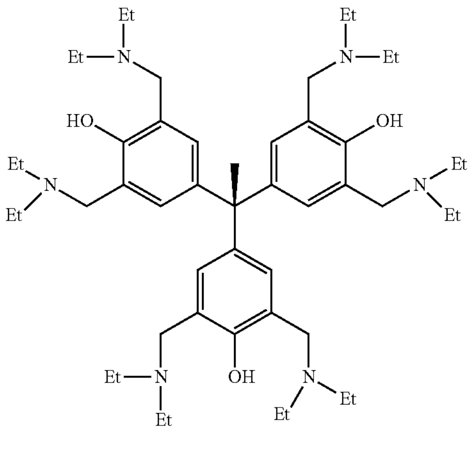

or its isomer, pharmaceutically acceptable salt, pharmaceutical product, hydrate, N-oxide, crystal or any combination thereof, and compositions comprising the same.

In one embodiment, the methods of this invention comprise the use of tri-phenyl compounds represented by the structure of formula IX:

IX

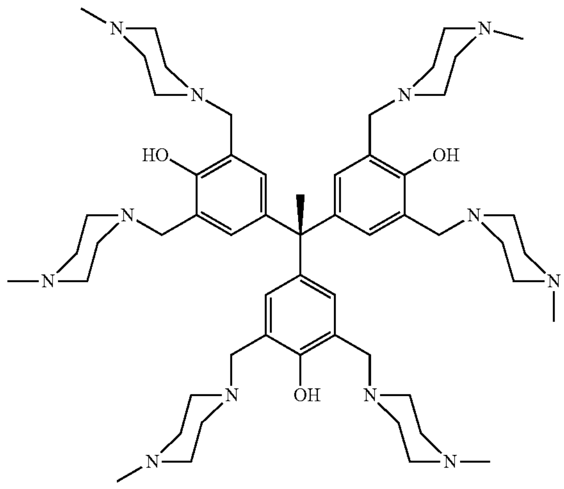

or its isomer, pharmaceutically acceptable salt, pharmaceutical product, hydrate, N-oxide, crystal or any combination thereof, and compositions comprising the same.

In one embodiment, the methods of this invention comprise the use of tri-phenyl compounds represented by the structure of formula X:

X

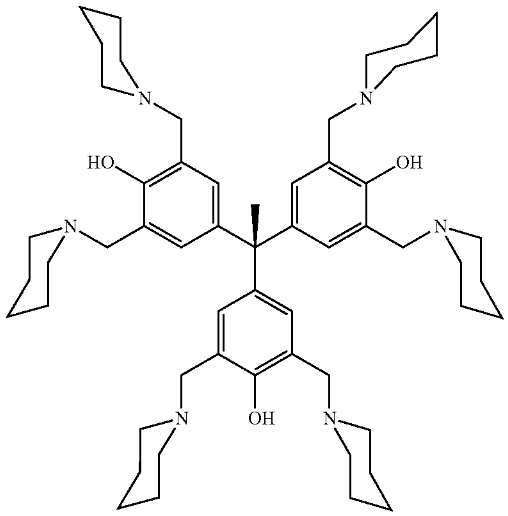

or its isomer, pharmaceutically acceptable salt, pharmaceutical product, hydrate, N-oxide, crystal or any combination thereof, and compositions comprising the same.

In one embodiment, the methods of this invention comprise the use of tri-phenyl compounds represented by the structure of formula XI:

XI

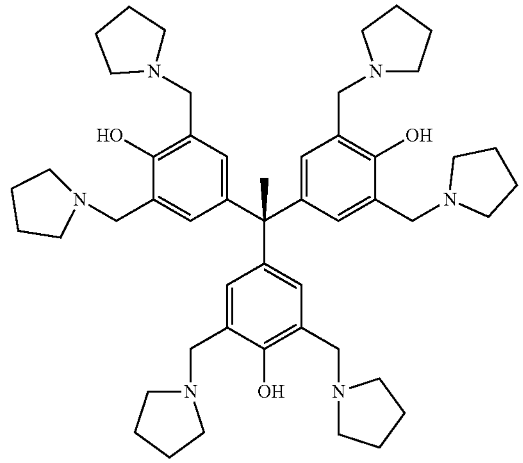

or its isomer, pharmaceutically acceptable salt, pharmaceutical product, hydrate, N-oxide, crystal or any combination thereof, and compositions comprising the same.

In one embodiment, the methods of this invention comprise the use of tri-phenyl compounds represented by the structure of formula XII:

XII

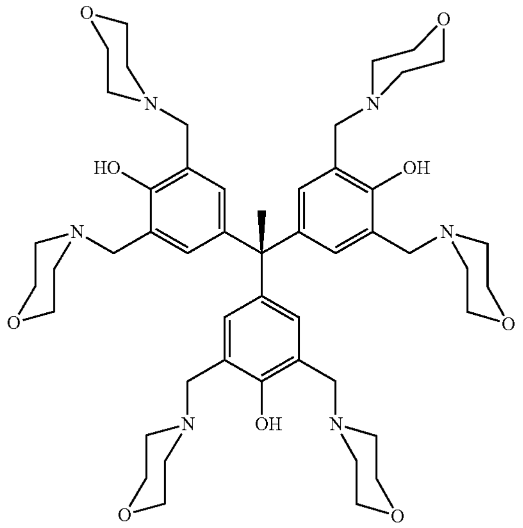

or its isomer, pharmaceutically acceptable salt, pharmaceutical product, hydrate, N-oxide, crystal or any combination thereof, and compositions comprising the same.

In one embodiment, the methods of this invention comprise the use of tri-phenyl compounds represented by the structure of formula XIII:

XIII

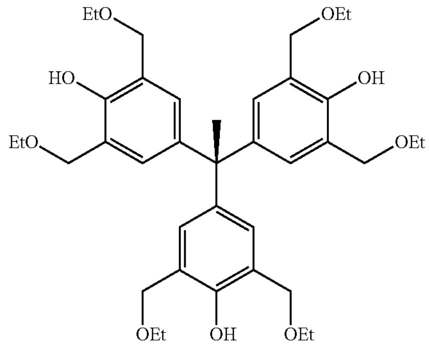

or its isomer, pharmaceutically acceptable salt, pharmaceutical product, hydrate, N-oxide, crystal or any combination thereof, and compositions comprising the same.

In another embodiment the structure of formula I is represented by the structure of formula XIV:

XIV

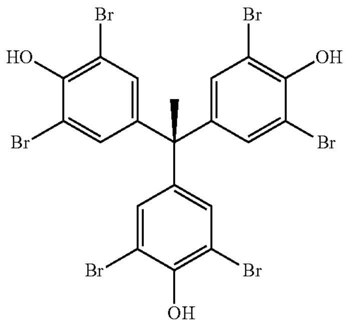

or its isomer, pharmaceutically acceptable salt, pharmaceutical product, hydrate, N-oxide, crystal or any combination thereof, and compositions comprising the same.

In another embodiment the structure of formula I is represented by the structure of formula XV:

XV

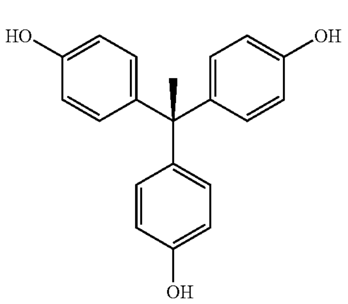

or its isomer, pharmaceutically acceptable salt, pharmaceutical product, hydrate, N-oxide, crystal or any combination thereof, and compositions comprising the same.

In another embodiment the structure of formula I is represented by the structure of formula XVI:

XVI

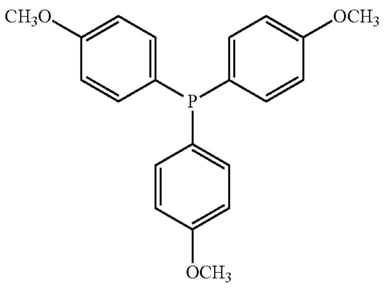

or its isomer, pharmaceutically acceptable salt, pharmaceutical product, hydrate, N-oxide, crystal or any combination thereof, and compositions comprising the same.

The term "alkyl" refers, in one embodiment, to a saturated aliphatic hydrocarbon, including straight-chain, branched-chain and cyclic alkyl groups. In one embodiment, the alkyl group has 1-12 carbons. In another embodiment, the alkyl group has 1-7 carbons. In another embodiment, the alkyl group has 1-6 carbons. In another embodiment, the alkyl group has 1-7 carbons. In another embodiment, the alkyl group has 2-6 carbons. In another embodiment, the alkyl group has 1-7 carbons. In another embodiment, the alkyl group has 2-8 carbons. In another embodiment, the alkyl group has 3-6 carbons. In another embodiment, the alkyl group has 3-7 carbons. In another embodiment, the alkyl group has 1~4 carbons. In another embodiment, the branched alkyl is an alkyl substituted by alkyl side chains of 1 to 5 carbons. In another embodiment, the branched alkyl is an alkyl substituted by haloalkyl side chains of 1 to 5 carbons. The alkyl group may be unsubstituted or substituted by a halogen, haloalkyl, hydroxyl, alkoxy, carbonyl, amido, alkylamido, dialkylamido, nitro, cyano, amino, monoalkylamino, diaikylamino, carboxyl, thio and/or thioalkyl.

An "alkenyl" group refers, in one embodiment, to an unsaturated hydrocarbon, including straight chain, branched chain and cyclic groups having one or more double bonds. The alkenyl group may have one double bond, two double bonds, three double bonds, etc. In another embodiment, the alkenyl group has 2-12 carbons. In another embodiment, the alkenyl group has 2-6 carbons. In another embodiment, the alkenyl group has 2-4 carbons. In another embodiment the alkenyl group is ethenyl ($CH—CH_2$). Examples of alkenyl groups are ethenyl, propenyl, butenyl, cyclohexenyl, etc. The alkenyl group may be unsubstituted or substituted by a halogen, hydroxy, alkoxy, carbonyl, amido, alkylamido, dialkylamido, nitro, cyano, amino, monoalkylamino, dialkylamino, carboxyl, thio and/or thioalkyl.

An "alkynyl" group refers, in one embodiment, to an unsaturated hydrocarbon, including straight chain, branched chain and cyclic groups having one or more triple bonds. The alkynyl group may have one triple bond, two triple bonds, triple double bonds, etc. In another embodiment, the alkynyl group has 2-12 carbons. In another embodiment, the alkynyl group has 2-6 carbons. In another embodiment, the alkenyl group has 2-4 carbons. In another embodiment the alkynyl group is ethynyl ($—CH═CH_2$). Examples of alkynyl groups are ethynyl, propynyl, butynyl, cyclohexynyl, etc. The alkynyl group may be unsubstituted or substituted by a halogen, hydroxy, alkoxy, carbonyl, amido, alkylamido, dialkylamido, nitro, cyano, amino, monoalkylamino, dialkylamino, carboxyl, thio and/or thioalkyl.

An "alkoxy" group refers, in another embodiment to an alkyl group as defined above, which is linked to oxygen. Examples of alkoxy groups are ethoxy, propoxy, tert-butoxy etc.

A "haloalkyl" group refers, in one embodiment, to an alkyl group as defined above, which is substituted by one or more halogen atoms, e.g. by F, Cl, Br or I.

An "aryl" group refers, in another embodiment, to an aromatic group having at least one carbocyclic aromatic group or heterocyclic aromatic group, which may be unsubstituted or substituted by one or more groups selected from halogen, haloalkyl, hydroxy, alkoxy, carbonyl, amido, alkylamido, dialkylamido, nitro, cyano, amino, monoalkylamino, dialkylamino, carboxy or thio or thioalkyl. In another embodiment, the aryl group is between 4-12—membered ring(s). In another embodiment, the aryl group is between 6-18-membered ring(s). In another embodiment, the aryl group is between 4-8-membered ring(s). In another embodiment, the aryl group is a 6-membered ring. In another embodiment, the aryl group is a fused ring system comprising of between 2-3 rings. Nonlimiting examples of aryl rings are phenyl, naphthyl, pyranyl, pyrrolyl, pyrazinyl, pyrimidinyl, pyrazolyl, pyridinyl, furanyl, thiophenyl, thiazolyl, imidazolyl, isoxazolyl, and the like.

A "heteroaryl" group refers, in another embodiment, to an aromatic group having at least one heterocyclic aromatic group, which may be unsubstituted or substituted by one or more groups selected from halogen, haloalkyl, hydroxy, alkoxy, carbonyl, amido, alkylamido, dialkylamido, nitro, cyano, amino, monoalkylamino, dialkylamino, carboxy or thio or thioalkyl. In another embodiment, the heteroaryl group is between 4-12-membered ring(s). In another embodiment, the heteroaryl group is between 6-18-membered ring(s). In another embodiment, the heteroaryl group is between 4-8-membered ring(s). In another embodiment, the heteroaryl group is a 6-membered ring. In another embodiment, the heteroaryl group is a fused ring system comprising of between 2-3 rings. Nonlimiting examples of heteroaryl rings are pyrrolyl, thienyl, thiazolyl, benzothienyl, naphthothienyl, purinyl, isothiazolyl, furyl, furazanyl, isobenznzofuranyl, pyranyl, chromenyl, xanthenyl, phenoxyxanthiinyl, indolyl, isoindolyl, indolizinyl, isoindolyzinyl, benzothienyl, oxazolyl, isoxazolyl, pyrazolyl, pyridyl, pyrazinyl, pyrimidinyl, pyridazinyl, and the like.

A "hydroxyl" group refers, in one embodiment, to an OH group. In some embodiments, when $R_1$, $R_2$ or $R_3$ of the compounds of the present invention is OR, then R is not OH.

In one embodiment, the term "halo" refers to a halogen, such as F, Cl, Br or I.

In another embodiment, the phrase "phenol" refers to an alcohol (OH) derivative of benzene.

An "amino" group refers to, in one embodiment, to a nitrogen atom attached by single bonds to hydrogen atoms, alkyl groups, alkenyl groups or aryl groups as described above, as described above, or a combination thereof. Nonlimiting examples of amino groups are $NH_2$, $N(Me)_2$, $N(Et)_2$, $N(Ph)_2$ and the like.

A "cycloalkyl" group refers, in one embodiment, to a non-aromatic, monocyclic or polycyclic ring comprising carbon and hydrogen atoms. A cycloalkyl group can have one or more carbon-carbon double bonds in the ring so long as the ring is not rendered aromatic by their presence. Examples of cycloalkyl groups include, but are not limited to, ($C_3$-$C_7$)cycloalkyl groups, such as cyclopropyl, cyclobutyl, cyclopentyl, cyclohexyl, and cycloheptyl, and saturated cyclic and bicyclic terpenes and ($C_3$-$C_7$)cycloalkenyl groups, such as cyclopropenyl, cyclobutenyl, cyclopentenyl, cyclohexenyl, and cycloheptenyl, and unsaturated cyclic and bicyclic terpenes. Preferably, the cycloalkyl group is a monocyclic ring or bicyclic to a ring structure comprising in addition to carbon atoms, sulfur, oxygen, nitrogen or any combination thereof, as part of the ring. In another embodiment the cycloalkyl is a 3-12-membered ring. In another embodiment the cycloalkyl is a 6-membered ring. In another embodiment the cycloalkyl is a 5-7-membered ring. In another embodiment the cycloalkyl is a 4-8-membered ring. In another embodiment, the cycloalkyl group may be unsubstituted or substituted by a halogen, haloalkyl, hydroxyl, alkoxy, carbonyl, amido, alkylamido, dialkylamido, cyano, nitro, $CO_2H$, amino, monoalkylamino, dialkylamino, carboxyl, thio and/or thioalkyl.

A "heterocycloalkyl" group refers, in one embodiment, to a non-aromatic, monocyclic or polycyclic ring comprising carbon and in addition to carbon, sulfur, phosphor, oxygen or nitrogen, as part of the ring. A heterocycloalkyl group can have one or more double bonds in the ring so long as the ring is not rendered aromatic by their presence. Examples of heterocycloalkyl groups include, but are not limited to, piperidine, piperazine, pyrane, morpholine. Preferably, the heterocycloalkyl group is a monocyclic ring or bicyclic to a ring structure comprising in addition to carbon atoms, sulfur, oxygen, nitrogen or any combination thereof, as part of the ring. In another embodiment the heterocycloalkyl is a 3-12-membered ring. In another embodiment the heterocycloalkyl is a 6-membered ring. In another embodiment the heterocycloalkyl is a 5-7-membered ring. In another embodiment the heterocycloalkyl is a 4-8-membered ring. In another embodiment, the heterocycloalkyl group may be unsubstituted or substituted by a halogen, haloalkyl, hydroxyl, alkoxy, carbonyl, amido, alkylamido, dialkylamido, cyano, nitro, $CO_2H$, amino, monoalkylamino, dialkylamino, carboxyl, thio and/or thioalkyl. In another embodiment the heterocycloalkyl is a cyclic urea, imidazolinyl, imidazolidinyl, pyrrolinyl, pyrrolidinyl, oxazolinyl, isoxazolinyl, oxazolidinyl, oxazolidonyl, isoxazolidonyl, pyrazolinyl, pyrazolidinyl, piperidyl, piperazine, morpholinyl.

The terms "alkylalkoxy", "alkylhaloalkyl", "alkylaryl", "alkylcycloalkyl", "alkylheterocycloalkyl", "alkylheteroaryl" and "alkylamino" refer, in one embodiment, to an alkyl group, as defined above, linked to alkoxy, haloalkyl, aryl, cycloalkyl, heterocycloalkyl, heteroaryl or amino group, respectively. The alkoxy, haloalkyl, aryl, cycloalkyl, heterocycloalkyl, heteroaryl or amino groups are as defined hereinabove. Examples include, but are not limited to, $CH_2$-OEt, $CH_2$—N-piperidine, $CH_2$—N-piperazine, $CH_2$—$N(Me)_2$, etc.

In another embodiment, the fused heterocycloalkyl of formula I-IV with the main aromatic ring forms a phenylpyrrolidone group. In another embodiment, the fused aryl of formula I-IV, with the main aromatic ring forms a naphthalene group. In another embodiment, the fused heteroaryl of formula I-IV, with the main aromatic ring forms a quinoline or isoquinoline group.

In one embodiment, this invention provides for the use of a compound as herein described and/or, its analog, derivative, isomer, metabolite, pharmaceutically acceptable salt, pharmaceutical product, hydrate, N-oxide, prodrug, polymorph, impurity or crystal or combinations thereof.

In one embodiment, the term "isomer" includes, but is not limited to, optical isomers and analogs, structural isomers and analogs, conformational isomers and analogs, and the like.

In one embodiment, the term "isomer" is meant to encompass optical isomers of the tri-phenyl compound. It is to be understood that the present invention encompasses any racemic, optically-active, polymorphic, or stereoisomeric form, or mixtures thereof, which form possesses properties useful in the treatment of telomerase expression and/or activity conditions described herein. In one embodiment, the tri-phenyl compounds are the pure (R)-isomers. In another embodiment, the tri-phenyl compounds are the pure(S)-isomers. In another embodiment, the tri-phenyl compounds are a mixture of the (R) and the(S) isomers. In another embodiment, the tri-phenyl compounds are a racemic mixture comprising an equal amount of the (R) and the(S) isomers. It is well known in the art how to prepare optically-active forms (for example, by resolution of the racemic form by recrystallization techniques, by synthesis from optically-active starting materials, by chiral synthesis, or by chromatographic separation using a chiral stationary phase).

The invention includes "pharmaceutically acceptable salts" of the compounds of this invention, which may be produced, in one embodiment, to form alkali metal salts and to form addition salts of free acids or free bases. Suitable pharmaceutically-acceptable acid addition salts of compounds of this invention may be prepared from an inorganic acid or from an organic acid. In one embodiment, examples of inorganic acids are hydrochloric, hydrobromic, hydroiodic, nitric, carbonic, sulfuric and phosphoric acid. In one embodiment, organic acids may be selected from aliphatic, cycloaliphatic, aromatic, araliphatic, heterocyclic, carboxylic and sulfonic classes of organic acids, examples of which are formic, acetic, propionic, succinic, glycolic, gluconic, lactic, malic, tartaric, citric, ascorbic, glucoronic, maleic, fumaric, pyruvic, aspartic, glutamic, benzoic, anthranilic, oxalic, p-toluenesulphonic, mesylic, salicylic, p-hydroxybenzoic, phenylacetic, mandelic, embonic (pamoic), methanesulfonic, ethylsulfonic, benzenesulfonic, sulfanilic, stearic, cyclohexylaminosulfonic, algenic, galacturonic acid. In one embodiment, suitable pharmaceutically-acceptable base addition salts of compounds of this invention include metallic salts made from aluminum, calcium, lithium, magnesium, potassium, sodium and zinc or organic salts made from N,N'-dibenzylethyleneldiamine, choline, chloroprocaine, diethanolamine, ethylenediamine, meglumine (N-methylglucamine) and procain. All of these salts may be prepared by conventional means from the corresponding compounds.

Pharmaceutically acceptable salts can be prepared, from the phenolic compounds, in other embodiments, by treatment with inorganic bases, for example, sodium hydroxide. In another embodiment, esters of the phenolic compounds can be made with aliphatic and aromatic carboxylic acids, for example, acetic acid and benzoic acid esters.

The invention also includes use of N-oxides of the amino substituents of the compounds described herein.

This invention provides for the use of derivatives of the compounds as herein described. In one embodiment, "derivatives" includes but is not limited to ether derivatives, acid derivatives, amide derivatives, ester derivatives and the like. In another embodiment, this invention further includes use of hydrates of the compounds as described herein. In one embodiment, "hydrate" includes but is not limited to hemihydrate, monohydrate, dihydrate, trihydrate and the like.

This invention provides, in other embodiments, use of metabolites of the compounds as herein described. In one embodiment, "metabolite" means any substance produced from another substance by metabolism or a metabolic process.

This invention provides, in other embodiments, use of pharmaceutical products of the compounds as herein described. The term "pharmaceutical product" refers, in other embodiments, to a composition suitable for pharmaceutical use (pharmaceutical composition), for example, as described herein.

In some embodiments, the invention provides methods and uses of the compounds and/or compositions comprising the compound of this invention, for promoting, improving, recovering or restoring fertility in a subject in need thereof, comprising contacting a gonadal or fertility-associated cell or tissue with a compound. In some embodiments, the invention provides a method of promoting, improving, recovering or restoring function to gonadal cells or tissues in a subject in need thereof, comprising contacting a gonadal or fertility-associated cell or tissue with a compound as herein descried and/or a composition comprising same, the invention provides methods and uses of the compounds and/or compositions comprising the compound of this invention, for promoting, enhancing or improving fertility-associated cell or tissue yield as part of an in vitro fertilization protocol.

In some embodiments, the invention provides compositions comprising the compound of this invention and/or treating female infertility-related conditions including luteal phase defect or premature ovarian failure (primary ovarian insufficiency or hypergonadotropic hypogonadism); and/or diminished granulosa cell telomerase activity; and/or treating male infertility-related conditions including impaired sperm production or impaired sperm delivery; and/or as an adjunct to in vitro fertilization (IVF) techniques; and/or to enhance sperm quality and/or egg quality. For example, and in some embodiments, the compounds of this invention prolong blastocyst viability in ex vivo culture, which in turn enhances implantation efficiency. In some embodiments, the treatment of the population with the compounds as herein described renders them more receptive to other IVF therapeutics, or in some embodiments, allows for the evaluation of combination therapies, or new compounds.

In some embodiments, the invention provides any compound as herein described or combinations of same or any composition comprising the compound or combinations of compounds of this invention in restoring, enhancing, rescuing or promoting any aspect of fertility in a subject exposed to radiation.

In one embodiment, this invention provides methods of treatment using a compound of this invention, or composition comprising the same, as herein described. In some embodiments, the invention provides methods of use of a compound of this invention for the treatment of the indicated diseases, disorders or conditions, and includes use of compositions comprising the same.

It will be appreciated that it is contemplated herein to use any combination of any compounds as herein described and/or compositions containing such combinations of compounds as herein described, for use in any method or assay, etc, as herein described.

In one embodiment, the terms "treating" or "treatment" includes preventive as well as disorder remittive treatment. The terms "reducing", "suppressing" and "inhibiting" have their commonly understood meaning of lessening or decreasing, in another embodiment, or delaying, in another embodiment, or reducing, in another embodiment the incidence, severity or pathogenesis of a disease, disorder or condition. In embodiment, the term treatment refers to delayed progression of, prolonged remission of, reduced incidence of, or amelioration of symptoms associated with the disease, disorder or condition. In one embodiment, the terms "treating" "reducing", "suppressing" or "inhibiting" refer to a reduction in morbidity, mortality, or a combination thereof, in association with the indicated disease, disorder or condition. In one embodiment, the term "progression" refers to an increasing in scope or severity, advancing, growing or becoming worse. The term "recurrence" means, in another embodiment, the return of a disease after a remission. In one embodiment, the methods of treatment of the invention reduce the severity of the disease, or in another embodiment, symptoms associated with the disease, or in another embodiment, reduces the number of biomarkers expressed during disease.

In one embodiment, the term "treating" and its included aspects, refers to the administration to a subject with the indicated disease, disorder or condition, or in some embodiments, to a subject predisposed to the indicated disease, disorder or condition. The term "predisposed to" is to be considered to refer, inter alia, to a genetic profile or familial relationship which is associated with a trend or statistical increase in incidence, severity, etc. of the indicated disease. In some embodiments, the term "predisposed to" is to be considered to refer, inter alia, to a lifestyle which is associated with increased risk of the indicated disease. In some embodiments, the term "predisposed to" is to be considered to refer, inter alia, to the presence of biomarkers which are associated with the indicated disease, for example, in cancer, the term "predisposed to" the cancer may comprise the presence of precancerous precursors for the indicated cancer.

The term "administering", in another embodiment, refers to bringing a subject in contact with a compound of the present invention. Administration can be accomplished in vitro, i.e. in a test tube, or in vivo, i.e. in cells or tissues of living organisms, for example humans. In one embodiment, the present invention encompasses administering the compounds of the present invention to a subject.

In one embodiment, the methods of this invention make use of the described compound of this invention contacting or binding a telomerase enzyme in an amount effective to increase telomerase activity and/or expression and thereby mediating the described effects. In some embodiments, the methods of this invention may include the preliminary step of identifying a cell or tissue in which an increase telomerase activity and/or expression is desired. The cell may be in culture, i.e. in vitro or ex vivo, or within a subject or patient in vivo. In one embodiment, an increase in telomerase expression and/or activity in a cell or tissue includes, for example, enhancement of the replicative capacity and/or lifespan of the contacted cells.

In some embodiments, for any method/kit or application as herein described, the invention specifically contemplates use of compounds 68, 70 and 79, respectively:

Compound 68

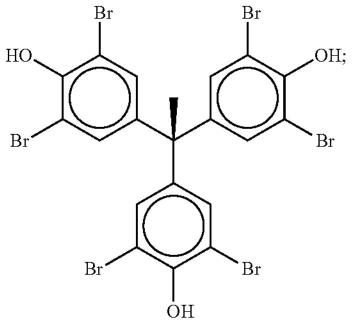

-continued

Conpound 70

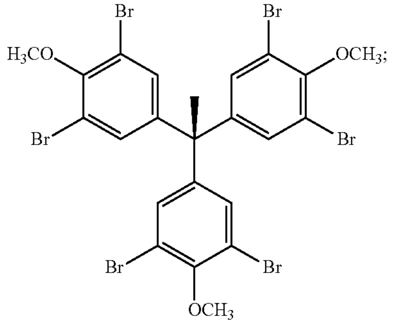

Compound 79

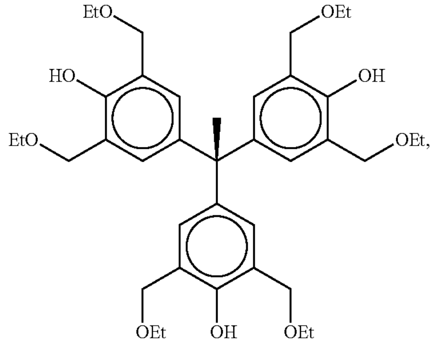

In some aspects, such cells may specifically be protected, enhanced, stimulated, etc. following exposure to radiation.

Pharmaceutical Compositions

In some embodiments, this invention provides methods of use which comprise administering a composition comprising the described compounds. As used herein, "pharmaceutical composition" means a "therapeutically effective amount" of the active ingredient, i.e. the compounds of this invention, together with a pharmaceutically acceptable carrier or diluent. A "therapeutically effective amount" as used herein refers to that amount which provides a therapeutic effect for a given condition and administration regimen.

In some embodiments, this invention provides compositions which may comprise at least one compound of this invention, in any form or embodiment as described herein. In some embodiments, the term "a" is to be understood to encompass a single or multiple of the indicated material. In some embodiments, the term "a" or "an" refers to at least one.

In some embodiments, any of the compositions of this invention will consist of a compound of this invention, in any form or embodiment as described herein. In some embodiments, of the compositions of this invention will consist essentially of a compound of this invention, in any form or embodiment as described herein.

In some embodiments, the term "comprise" refers to the inclusion of the indicated active agent, such as the compounds of this invention, as well as inclusion of other active agents, and pharmaceutically acceptable carriers, excipients, emollients, stabilizers, etc., as are known in the pharmaceutical industry. In some embodiments, any of the compositions of this invention will comprise a compound of formula I-XVI in any form or embodiment as described herein. In some embodiments, any of the compositions of this invention will consist of a compound of formula I-XVI, in any form or embodiment as described herein. In some embodiments, of the compositions of this invention will consist essentially of a compound of this invention, in any form or embodiment as described herein. In some embodiments, the term "comprise" refers to the inclusion of the indicated active agent, such as the compound of this invention, as well as inclusion of other active agents, and pharmaceutically acceptable carriers, excipients, emollients, stabilizers, etc., as are known in the pharmaceutical industry. In some embodiments, the term "consisting essentially of refers to a composition, whose only active ingredient is the indicated active ingredient, however, other compounds may be included which are for stabilizing, preserving, etc. the formulation, but are not involved directly in the therapeutic effect of the indicated active ingredient. In some embodiments, the term "consisting essentially of refers to a composition, whose only active ingredient with a comparable mode of action, or comparable molecular target is the indicated active ingredient, however, other active ingredients may be incorporated, with such secondary active ingredients acting on different targets, or in a palliative capacity. In some embodiments, the term "consisting essentially of may refer to components which facilitate the release of the active ingredient. In some embodiments, the term "consisting" refers to a composition, which contains a compound as herein described as the only active ingredient and a pharmaceutically acceptable carrier or excipient.

In another embodiment, the invention provides a composition comprising a compound of this invention, as herein described, or its prodrug, analog, isomer, metabolite, derivative, pharmaceutically acceptable salt, pharmaceutical product, polymorph, crystal, impurity, N-oxide, ester, hydrate or any combination thereof and a suitable carrier or diluent.

An active component can be formulated into the composition as neutralized pharmaceutically acceptable salt forms. Pharmaceutically acceptable salts include the acid addition salts, which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The pharmaceutical compositions containing the compound of this invention can be administered to a subject by any method known to a person skilled in the art, such as orally, parenterally, intravascularly, paracancerally, transmucosally, transdermally, intramuscularly, intranasally, intravenously, intradermally, subcutaneously, sublingually, intraperitoneally, intraventricularly, intracranially, intravaginally, by inhalation, rectally, intratumorally, or by any means in which the recombinant virus/composition can be delivered to tissue (e.g., needle or catheter). Alternatively, topical administration may be desired for application to mucosal cells, for skin or ocular application. Another method of administration is via aspiration or aerosol formulation.

The compositions of the present invention are formulated in one embodiment for oral delivery, wherein the active compounds may be incorporated with excipients and used in the form of ingestible tablets, buccal tables, troches, capsules, elixirs, suspensions, syrups, wafers, and the like. The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. Syrup of elixir may contain the active compound, sucrose as a sweetening agent methyl, and propylparabens as preservatives, a dye and flavoring, such as cherry or orange flavor. In addition, the active compounds may be incorporated into sustained-release, pulsed release, controlled release or postponed release preparations and formulations.

In another embodiment, the compositions of this invention comprise one or more, pharmaceutically acceptable carrier materials.

In one embodiment, the carriers for use within such compositions are biocompatible, and in another embodiment, biodegradable. In other embodiments, the formulation may provide a relatively constant level of release of one active component. In other embodiments, however, a more rapid rate of release immediately upon administration may be desired. In other embodiments, release of active compounds may be event-triggered. The events triggering the release of the active compounds may be the same in one embodiment, or different in another embodiment. Events triggering the release of the active components may be exposure to moisture in one embodiment, lower pH in another embodiment, or temperature threshold in another embodiment. The formulation of such compositions is well within the level of ordinary skill in the art using known techniques. Illustrative carriers useful in this regard include microparticles of poly (lactide-co-glycolide), polyacrylate, latex, starch, cellulose, dextran and the like. Other illustrative postponed-release carriers include supramolecular biovectors, which comprise a non-liquid hydrophilic core (e.g., a cross-linked polysaccharide or oligosaccharide) and, optionally, an external layer comprising an amphiphilic compound, such as phospholipids. The amount of active compound contained in one embodiment, within a sustained release formulation depends upon the site of administration, the rate and expected duration of release and the nature of the condition to be treated suppressed or inhibited.

In one embodiment it will be desirable to deliver the compositions disclosed herein parenterally, intravenously, intramuscularly, or even intraperitoneally. Such approaches are well known to the skilled artisan, some of which are further described, for example, in U.S. Pat. Nos. 5,543,158; 5,641,515 and 5,399,363, all of which are fully incorporated by reference. In certain embodiments, solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. It must be stable under the conditions of manufacture and storage and must be preserved against the contaminating action of microorganisms, such as bacteria and fungi.

In another embodiment, it will be preferable to include isotonic agents, for example, sugars or sodium chloride. In other embodiments, prolonged absorption of the injectable compositions will be desirable. Prolonged absorption of the injectable compositions can be brought about by the use of agents delaying absorption, for example, aluminum monostearate and gelatin, in the compositions.

Parenteral vehicles include in certain embodiments sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, collating agents, inert gases and the like In some embodiments, the compounds of this invention may be administered at various dosages to a subject, which in one embodiment, is a human subject. In one embodiment, the compounds of this invention are administered at a dosage of 0.1-200 mg per day. In one embodiment, the compound of this invention is administered at a dose of 0.1-10 mg, or in another embodiment, 0.1-25 mg, or in another embodiment, 0.1-50 mg, or in another embodiment, 0.3-15 mg, or in another embodiment, 0.3-30 mg, or in another embodiment, 0.5 25 mg, or in another embodiment, 0.5-50 mg, or in another embodiment, 0.75-15 mg, or in another embodiment, 0.75-60 mg, or in another embodiment, 1-5 mg, or in another embodiment, 1-20 mg, or in another embodiment, 3-15 mg, or in another embodiment, 1-30 mg, or in another embodiment, 30-50 mg, or in another embodiment, 30-75 mg, or in another embodiment, 100-2000 mg. In some embodiments, the compounds of this invention may be administered at different dosages, as a function of time, or disease/symptom/condition severity, or age, or other factors, as will be appreciated by one skilled in the art.

The compounds of this invention may be administered at various dosages. In one embodiment, the compounds of this invention are administered at a dosage of 1 mg. In another embodiment the compounds of this invention are administered at a dosage of 5 mg, or in another embodiment, 3 mg, or in another embodiment 10 mg, or in another embodiment 15 mg, or in another embodiment 20 mg, or in another embodiment 25 mg, or in another embodiment 30 mg, or in another embodiment 35 mg, or in another embodiment 40 mg, or in another embodiment 45 mg, or in another embodiment 50 mg, or in another embodiment 55 mg, or in another embodiment 60 mg, or in another embodiment 65 mg, or in another embodiment 70 mg, or in another embodiment 75 mg, or in another embodiment 80 mg, or in another embodiment 85 mg, or in another embodiment 90 mg, or in another embodiment 95 mg or in another embodiment 100 mg.

While the compounds of the invention can be administered as the sole active pharmaceutical agent, they can also be used in combination with one or more other compound, and/or in combination with other agents used in the treatment and/or prevention of the diseases, disorders and/or conditions, as will be understood by one skilled in the art. In another embodiment, the compounds of the present invention can be administered sequentially with one or more such agents to provide sustained therapeutic and prophylactic effects. In another embodiment, the compounds may be administered via different routes, at different times, or a combination thereof.

In addition, the compounds of the present invention can be used, either singly or in combination, in combination with other modalities for preventing or treating conditions, diseases or disorders. In some embodiments, such other treatment modalities may include without limitation, surgery, radiation, hormone supplementation, diet regulation, wound debridement, etc., as will be appropriate for the condition being treated. These can be performed sequentially (e.g., treatment with a compound of the invention following surgery or radiation) or in combination (e.g., in addition to a diet regimen).

The additional active agents may generally be employed in therapeutic amounts as indicated in the PHYSICIANS'

DESK REFERENCE (PDR) 53rd Edition (1999), or such therapeutically useful amounts as would be known to one of ordinary skill in the art. The compounds of the invention and the other therapeutically active agents can be administered at the recommended maximum clinical dosage or at lower doses. Dosage levels of the active compounds in the compositions of the invention may be varied to obtain a desired therapeutic response depending on the route of administration, severity of the disease and the response of the patient. The combination can be administered as separate compositions or as a single dosage form containing both agents. When administered as a combination, the therapeutic agents can be formulated as separate compositions that are given at the same time or different times, or the therapeutic agents can be given as a single composition.

The pharmaceutical composition can comprise the compounds of this invention alone or can further include a pharmaceutically acceptable carrier and can be in solid or liquid form such as tablets, powders, capsules, pellets, solutions, suspensions, elixirs, emulsions, gels, creams, or suppositories, including rectal and urethral suppositories. Pharmaceutically acceptable carriers include gums, starches, sugars, cellulose materials, and mixtures thereof. The pharmaceutical preparation containing the compounds of this invention can be administered to a subject by, for example, subcutaneous implantation of a pellet; in a further embodiment, the pellet provides for controlled release of the compounds of this invention over a period of time. The preparation can also be administered by intravenous, intraarterial, or intramuscular injection of a liquid preparation, oral administration of a liquid or solid preparation, or by topical application. Administration can also be accomplished by use of a rectal suppository or a urethral suppository. The pharmaceutical composition can also be a parenteral formulation; in one embodiment, the formulation comprises a liposome that includes a complex of a compound of this invention.

The pharmaceutical composition of the invention can be prepared by known dissolving, mixing, granulating, or tablet-forming processes. For oral administration, the compounds of this invention or their physiologically tolerated derivatives such as salts, esters, N-oxides, and the like are mixed with additives customary for this purpose, such as vehicles, stabilizers, or inert diluents, and converted by customary methods into a suitable form for administration, such as tablets, coated tablets, hard or soft gelatin capsules, aqueous, alcoholic or oily solutions. Examples of suitable inert vehicles are conventional tablet bases such as lactose, sucrose, or cornstarch in combination with binders like acacia, cornstarch, gelatin, or with disintegrating agents such as cornstarch, potato starch, alginic acid, or with a lubricant such as stearic acid or magnesium stearate. Examples of suitable oily vehicles or solvents are vegetable or animal oils such as sunflower oil or fish-liver oil. Preparations can be effected both as dry and as wet granules. For parenteral administration (subcutaneous, intravenous, intraarterial, or intramuscular injection), the compounds of this invention or their physiologically tolerated derivatives such as salts, esters, N-oxides, and the like are converted into a solution, suspension, or emulsion, if desired with the substances customary and suitable for this purpose, for example, solubilizers or other auxiliaries. Examples are: sterile liquids such as water and oils, with or without the addition of a surfactant and other pharmaceutically acceptable adjuvants. Illustrative oils are those of petroleum, animal, vegetable, or synthetic origin, for example, peanut oil, soybean oil, or mineral oil. In general, water, saline, aqueous dextrose and related sugar solutions, and glycols such as propylene glycols or polyethylene glycol are preferred liquid carriers, particularly for injectable solutions.

The preparation of pharmaceutical compositions which contain an active component is well understood in the art. Typically, such compositions are prepared as an aerosol of the polypeptide delivered to the nasopharynx or as injectables, either as liquid solutions or suspensions, however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, or pH buffering agents which enhance the effectiveness of the active ingredient.

For topical administration to body surfaces using, for example, creams, gels, drops, and the like, the compounds of this invention or their physiologically tolerated derivatives such as salts, esters, N-oxides, and the like are prepared and applied as solutions, suspensions, or emulsions in a physiologically acceptable diluent with or without a pharmaceutical carrier.

In another embodiment, the active compound can be delivered in a vesicle, in particular a liposome (see Langer, Science 249:1527-1533 (1990); Treat et al., in *Liposomes in the Therapy of Infectious Disease and Cancer*, Lopez-Berestein and Fidler (eds.), Liss, New York, pp. 353-365 (1989); Lopez-Berestein, ibid., pp. 317-327; see generally ibid).

In one embodiment, the present invention provides combined preparations. In one embodiment, the term "a combined preparation" defines especially a "kit of parts" in the sense that the combination partners as defined above can be dosed independently or by use of different fixed combinations with distinguished amounts of the combination partners i.e., simultaneously, concurrently, separately or sequentially. In some embodiments, the parts of the kit of parts can then, e.g., be administered simultaneously or chronologically staggered, that is at different time points and with equal or different time intervals for any part of the kit of parts. The ratio of the total amounts of the combination partners, in some embodiments, can be administered in the combined preparation. In one embodiment, the combined preparation can be varied, e.g., in order to cope with the needs of a patient subpopulation to be treated or the needs of the single patient which different needs can be due to a particular disease, severity of a disease, age, sex, or body weight as can be readily made by a person skilled in the art.

It is to be understood that this invention is directed to compositions and combined therapies as described herein, for any disease, disorder or condition, as appropriate, as will be appreciated by one skilled in the art. Certain applications of such compositions and combined therapies have been described hereinabove, for specific diseases, disorders and conditions, representing embodiments of this invention, and methods of treating such diseases, disorders and conditions in a subject by administering a compound as herein described, alone or as part of the combined therapy or using the compositions of this invention represent additional embodiments of this invention.

Treatment of Conditions or Diseases

In some embodiments, this invention provides compounds, and pharmaceutical compositions comprising the same for the treatment of conditions and/or diseases specifically involving gonadal cells or tissue, or cells or tissue associated with fertility in a subject.

In some aspects, such conditions/diseases, etc, are effected via the employ of compounds, which interact with the telomerase enzyme and stimulate and/or increase telomerase expression and/or activity in the tissues and cells of a subject, which in some aspects is via a canonical and in some embodiments, via a non-canonical pathway.

In some embodiment, such activity is decreased or absent, or in some embodiments, is damaged due to, for example, a disease, disorder or condition in the subject, and/or arising as a result of a treatment of a disease or disorder or condition in the subject.

In some aspects, the subjects helped by the compounds, compositions and methods of this invention may be afflicted or predisposed to a caner or precancerous condition. In some aspects, the subjects helped by the compounds, compositions and methods of this invention may be exposed to radiation or other toxic therapy.

In some embodiments, the subjects helped by the compounds, compositions and methods of this invention may be suffering from or predisposed to or have suffered or been subjected to a) luteal phase defect; b) premature ovarian failure (primary ovarian insufficiency or hypergonadotropic hypogonadism); c) impaired sperm production; d) impaired sperm delivery; while sustaining said subject in good health and/or other clinical therapeutic and/or diagnostic areas, including any embodiment of what is encompassed by the term "treating" as described herein.

In some embodiments, the subjects helped by the compounds, compositions and methods of this invention may require or be positively affected by improved fertility or improved fertility potential in situ or via an in vitro protocol, or a process for preparation for a fertility promoting procedure in situ or in vitro.

For example, and in some embodiments, the subject is male and the compounds, compositions and methods of this invention expand the sperm in or sperm sample taken from a subject for treating impaired or reduced fertility in the subject. In some aspects, the subject is undergoing a GIF, AIF or IVF protocol. In other embodiments, the compounds, compositions and methods of this invention result in enhanced quantity/quality of sperm in the subject without need for any additional fertility treatment or manipulation. In some embodiments, the subject may have been exposed to radiation.

For example, and in some embodiments, the subject is female and the compounds, compositions and methods of this invention expand the mature follicles, or ovum in or taken/retrieved from a subject for treating impaired or reduced fertility in the subject. In some aspects, the subject is participating in a GIF, AIF or IVF protocol. In other embodiments, the compounds, compositions and methods of this invention result in enhanced quantity/quality of mature follicles/ovum in the subject without need for any additional fertility treatment or manipulation. In some embodiments, the subject may have been exposed to radiation.

In some embodiments, the subjects helped by the compounds, compositions and methods of this invention may require or be positively affected by exposure of a gonadal or fertility-associated cell or tissue being isolated from or within a subject having a cancerous or precancerous condition, suffering from an endocrine disorder that negatively impacts steroidogenesis, suffering from infertility or predisposed to infertility, or suffering from a genetic disorder or other disorder causing premature failure of a gonadal cell or tissue.

In one embodiment, the compounds and compositions of this invention activate telomerase, and methods as described herein are useful thereby.

Example 3 as further described herein demonstrated that the compounds of this invention increased telomerase expression and activity in the ovary at all estrous stages evaluated, even when using a single dose of the embodied compounds.

Figure 12A:
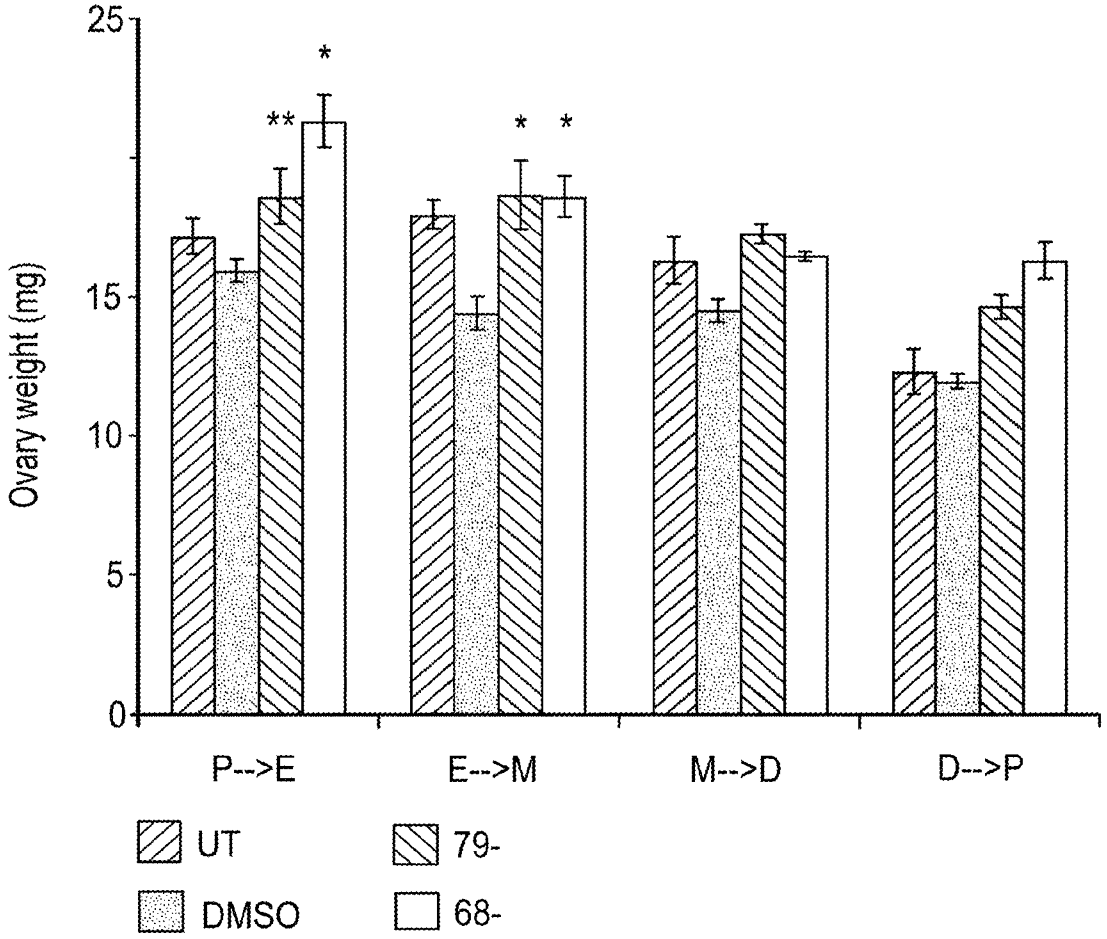
FIGS. 12A, B.
Figure 12B:
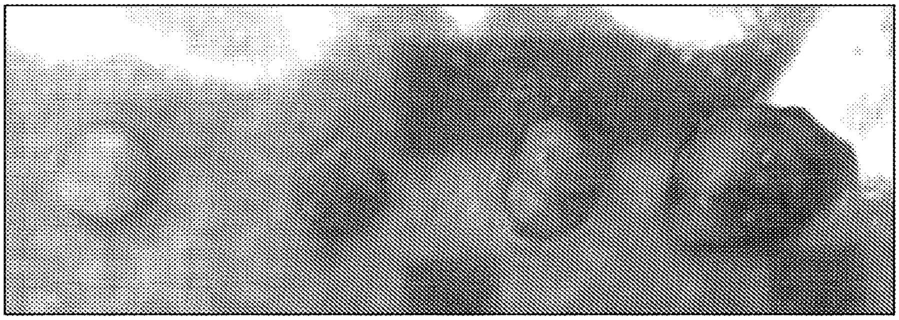
(FIG. 12B) A Representative picture of ovaries from 3 months old mice 12 hrs after treatments.

Similarly, the embodied compounds of this invention facilitated/promoted increased ovarian size and weight at each stage of estrous cycle and accelerated the estrous cycle (FIGS. 12A, B).

The embodied compounds promoted and enhanced ovulation, (FIGS. 13A-D).

The embodied compounds induced secretion of progesterone, as well. The compounds of this invention increased the number of embryos.

The embodied compounds thus clearly improve and promote female fertility and contribute greatly to increasing fertility therapeutic strategies, and in some aspects are particularly suitable in supporting IVF treatments, in consideration of the data provided in the next example, as well.

Figure 22:
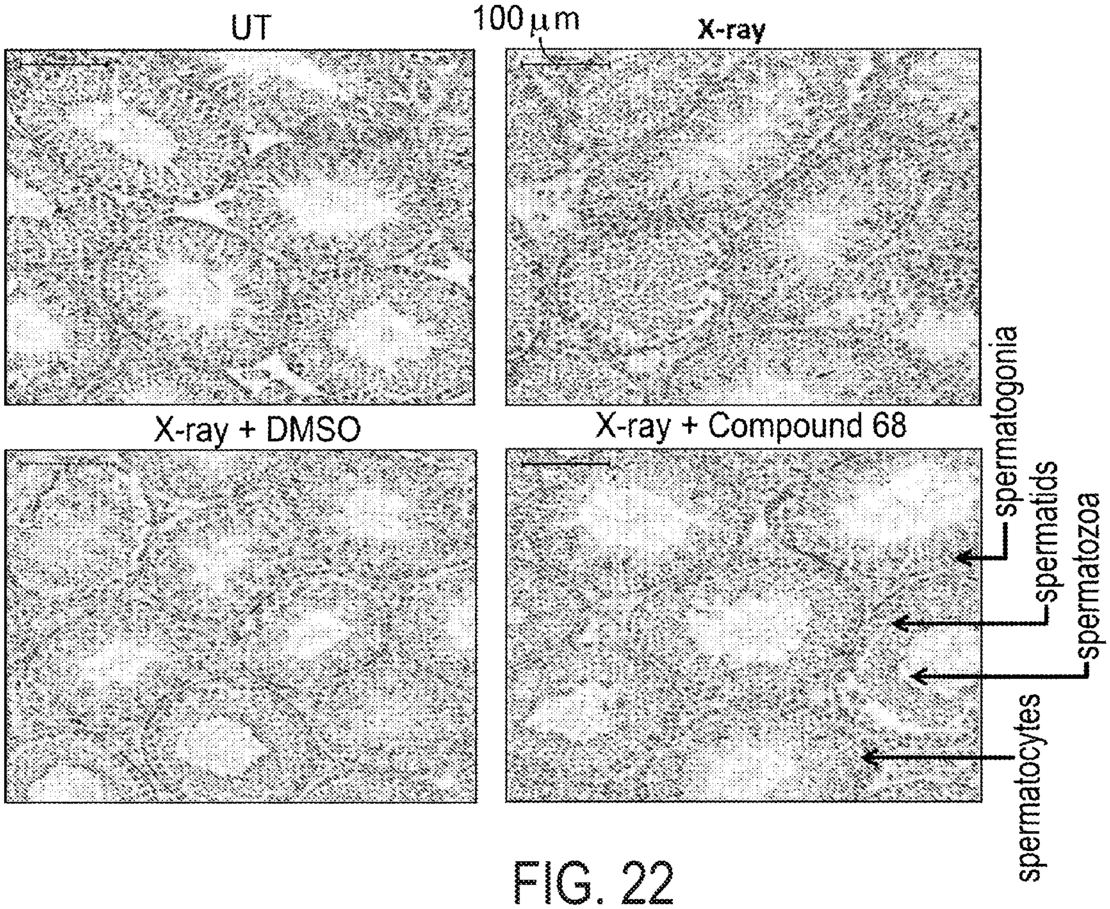
FIG. 22: H&E staining shows a significant destruction in the morphology of the testicular tissue particularly in the spermatogonia cells layer. Compound 68 treatment protects the spermatogonia cells layer from the damaging effects of X-ray and the morphology of the testicular tissue remains intact. ICR mice (3 months old) were subjected to X-ray radiation (2.5 Gy) followed by immediately injection of DMSO or treatment with Compound 68. The testes were removed 12 hrs after treatments and subjected to histological examination, a representative picture (stained with H&E).

Example 4 demonstrated that the embodied compounds are also useful in, inter alia, protecting male gonadal cells/tissue from X-ray induced morphological damage (FIG. 22).

A beneficial effect of the embodied compounds on sperm count at different times after X-ray radiation was also demonstrated (FIGS. 25A-D). While the sperm counts from X-ray treated subjects were significantly reduced, subjects exposed to X-ray irradiation but administered the embodied compounds showed significantly increased numbers of sperms in the epididymis (FIGS. 25A-D).

The embodied compounds of this invention are therefore, inter alia, useful in promoting fertility in subjects exposed to radiation, and thereby in some aspects, significantly restoring tissue morphology, increased CREM expression and decreased DSB formation. Furthermore, treatment with select compounds, such as Compound 68 increased the sperm count in the epididymis, at different time points post radiation, indicating its promise as a therapy to restore male fertility in irradiated subjects.

Figure 26A:
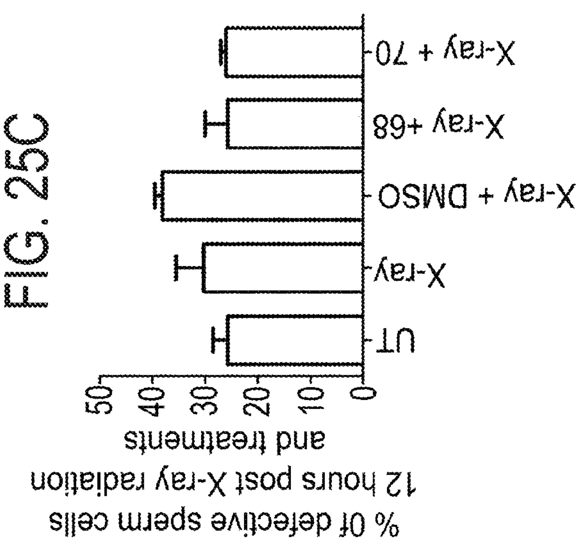
FIGS. 26A and 26B: Treatment with embodied compounds protected sperm against defective head morphology post-radiation exposure. Three-month old mice were irradiated with X-ray (2.5 Gy) and treated with a single S.C. injection of 6 mg/kg of compound 68 or 70. Mice were sacrificed 12 hours later and sperm were removed from the epididymis and stained with eosin. The number of morphologically defective sperm (head morphology) were quantified and presented as a percentage value of the total sperm count (N=6 mice per group) (FIG. 26A).

Such protective effects in gonadal tissue following irradiation were also demonstrated effective in female subjects (FIGS. 26A, B).

The ability of a compound to increase telomerase expression and/or activity in a cell can be determined using the TRAP (Telomeric Repeat Amplification Protocol) assay, which is known in the art (e.g., Kim et al, U.S. Pat. No. 5,629,154; Harley et al, U.S. Pat. No. 5,891,639). The activity is typically compared to the activity similarly measured in a control assay of such cells (e g., a telomerase activity 50% greater than observed in a solvent control). Cell lines suitable for use in the assay, may comprise normal human fibroblasts (Now) or normal human keratinocytes (NHK).

In some embodiments, the telomere length may serve as useful indicator for the telomerase expression and/or activity. In one embodiment, telomerase expression and/or activation is important in treating cancer, premature aging syndrome or segmental progeria, genetic anomalies and age-related diseases. The telomere length has distinct patterns of expression in specific disease progression, and is a function of its activation, thus measuring such length as a function of treatment has value, in some embodiments, in terms of the prognosis of different diseases.

In one embodiment, telomere length can be measured by Southern blot, hybridization protection assay, fluorescence in situ hybridization, flow cytometry, primed in situ, quantitative-polymerase chain reaction and single telomere length analysis, which are all techniques known in the art (Kah-Wai Lin and Ju Yan, *J. Cell. Mol. Med.,* 2005, Vol 9, No. 4, 977-989).

The following examples are presented in order to more fully illustrate the preferred embodiments of the invention. They should in no way be construed, however, as limiting the broad scope of the invention.

EXAMPLES

Example 1

Synthesis of Compounds

Compounds of the invention were synthesized as described in International Application Numbers WO 2008/149,345; WO 2008/149353; WO 2008/149,346, all of which are fully incorporated herein by reference in their entirety.

In particular, the following compounds were utilized: Compound 79:

Compound 79

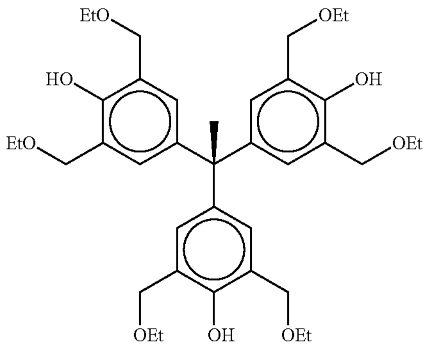

1,1,1-tris (4-hydroxy-3,5-methylene ethoxy-phenyl)-ethane

Compound 68

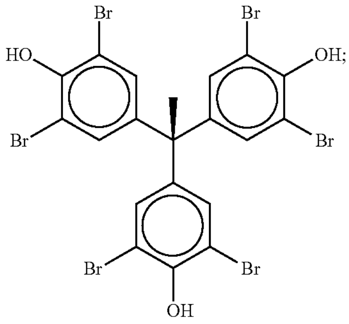

and 1,1,1-tris (4-hydroxy-3,5-dibromo-phenyl)-ethane

-continued

Compound 70

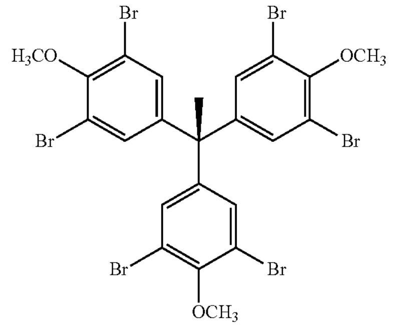

$C_{23}H_{18}Br_6O_3$
Mol. Wt.: 821.81

Synthetic methods for preparing compound 70, may include the following:

1,1,1-tris(4-methoxyphenyl)-ethane-To a solution of 1.53 g,5 mM, 1,1,1-tris(4-hydroxyphenyl)-ethane in 20 ml ethanol and 10 ml water were added, during 1 hour and simultaneously in portions, 1 g,25 mM, NaOH in 10 ml water and 5.1 gr,40 mM of dimethyl sulphate (1:8 molar ratio). The solution was then refluxed for 1 hour, and stirred 70 hours at RT. The white precipitate was filtered, washed with water and dried to give 1.74 g. Recrystalization twice from 50 ml ethanol gave 1.15 gr white crystals, 66% yield, m.p.–160°. TLC Rf=0.85 in $CH_2Cl_2$.

NMR $CDCl_3$ δ 6.99, 6.79 (12H, $AB_q$, $J_{AB}$=8.8 Hz), 3.78 (9H,s,$OCH_3$), 2.11 (3H, s,$CH_3$).

To a solution of 0.49 gr, 1.4 mM,1,1,1-tris(4-methoxyphenyl)-ethane, from A, in 22 ml 1,2-dichloroethane were added in portions 1.65 gr, 10.2 mM, (7.3: 1 ratio) of bromine in 5 ml 1,2-dichloroethane. The solution was stirred at RT overnight and heated for 3 hours to 70°, and worked up (sodium thiosulphate) to give 1.0 gr crude product,. TLC shows no SM, but NMR is mixture (m at 6.90 ppm, and 4 methoxy). The solid was brominated again with 1 gr bromine, reflux 18 hours. Workup and Trituration with hot ethanol gave 0.27 gr white solid, 23% yield, mp–160°. TLC Rf=0.95 in $CH_2C_{12}$.

NMR $CDCl_3$ δ 7.16 (6H,s,ArH), 3.92,3.91 (6:4 ratio) (9H,2s,$OCH_3$),2.04,2.03 (4:6 ratio) (3H,s,$CH_3$).

Example 2

The effect of embodied compounds of this invention on steroidogenesis in rat granulosa cells

Materials and Methods

Immortalized rat granulosa cells expressing FSH receptor were treated with either pregnant mare serum gonadotropin (PMSG), or the indicated compounds, or both for 6 hours. Protein extracts prepared from these cells served for telomerase activity measurement using a telomere repeat amplification protocol (TRAP) assay.

Briefly, protein extract incubated with oligonucleotide, which serves as a template for telomerase (TS), for 45 minutes at 30° C. followed by PCR with reverse primer (ACX) and internal control. PCR products were separated on 4.5% agarose gel. RNA extracts were used for cDNA synthesis and quantitative real time PCR with specific primers to Telomerase reverse transcriptase (TERT), Steroidogenic acute regulatory protein (StAr) and β-actin as a reference gene. To measure progesterone levels secreted by the cells, granulosa cells were cultured with or without 1 IU/mL PMSG and DMSO, Compound 79 50 nM or compound 70 50 nM in the presence of 100 nM dexamethasone. After 24 hours progesterone levels cell-culture medium were determined by radioimmunoassay (RIA). For cell proliferation measurement, $1\times10^5$ cells were seeded in a 96 wells plate with 1 IU/mL PMSG and DMSO, Compound 79 50 nM or Compound 70 50 nM. After 24 hours cells viability was measured by XTT proliferation assay.

Preparation of Proteins Extract

The ovaries were homogenized and centrifuged at 1200 RPM at 4° C. for 10 min, then suspended in CHAPS buffer (10 mM Tris-HCl pH-7.0, 1 mM $MgCl_2$, 1 mM EDTA pH-0.5, 0.1 mM PMSF, 0.5% 3 [(3 Cholamidopropyl) dimethylammonio]-propanesulfonic acid [CHAPS] and 10% glycerol) on ice for 30 min and centrifuged again at 13500 RPM at 4° C. for 30 min, the supernatant was collected. Total proteins concentration was determined using the Bio-Rad protein assay kit (Bio-Rad Laboratories, Germany).

Telomerase Repeat Amplification Protocol (TRAP) Assay

Telomerase activity in mice ovary was evaluated by a slight modification of the TRAP assay [Grin, Y., T. Admoni, and E. Priel, Telomerase activity in the various regions of mouse brain: non-radioactive telomerase repeat amplification protocol (TRAP) assay. J Vis Exp, 2014 (91): p. e51865]. The assay contains three main stages: Telomerase reaction, PCR reaction and b high resolution agarose minigel electrophoresis analysis. Proteins extract (0.5 μg/μl) was incubated with 1 μl of 10×TRAP assay reaction mix: (20 mM Tris-HCl pH 8.2, 63 mM KCl, 1.5 mM $MgCl_2$, 1 mM EDTA, 0.1 mg/mL BSA and 0.05% Tween 20) and 0.1 μg telomerase substrate (TS) primer (5'-AATCCGTCGAGC AGAGTT-3', 0.1 μg/μl), 2.5 mM dNTP's and UPW to a final volume of 10 μl for 45 minutes at 30° C. water bath. Then, the telomerase reaction products were amplified by PCR using reaction mix containing 0.1 μg ACX primer (5'-GCGCGGCTTACCCTTACCCTTACCCTAACC-3', 0.2 μg/μl), 1.25 μl Titanium Taq polymerase buffer x10 and 0.25 μl Titanium Taq-polymerase x50. Internal standard primer used as a control: 0.5×10-15 μg IS primer (S'AATCCGTCGAGCAGAGTTAAAAG-GCCGAGAAGCGAT-3', 1×10-15 μg/μl) and 0.025 μg ISR primer (5'-ATCGCTTCTCGGCCTTTT-3', 0.05 μg/μl). 34 PCR cycles as previously described [Grin, Y., T. Admoni, and E. Priel, Telomerase activity in the various regions of mouse brain: non-radioactive telomerase repeat amplification protocol (TRAP) assay. J Vis Exp, 2014 (91): p. e51865] were used for the detection of the products. These products were separated on a 4.5% high-resolution agarose mini-gel and detected with Gel-Red solution (X10000 stock solution diluted to X3 working solution with 0.01M NaCl) for 20 minutes. The gels were filmed using a UV trans-illuminator digital camera system at 302 nm wavelength. All assays included CHAPS buffer as negative control and positive control-proteins extract from Glioblastoma cells.

Quantification of Telomerase Activity

TRAP assay products were quantified by densitometric analysis using the EZQuant software (EZQuant Ltd. Rehovot, Israel) and normalized to IS (Internal standard). We also used positive control (proteins extract from cancer cells) in each of the experiments as a constant reference for the comparison between the different experiments. The data which were normalized to the IS were calculated as % from the positive control values in each experiment.

Isolation of Total RNA and cDNA Preparation

Mouse ovary was removed and homogenized in Tri-reagent RNA extraction buffer (Sigma-Aldrich, Rehovot, Israel) and RNA was isolated according to the manufacture's protocol. RNA concentration was determined using NanoDrop 2000c spectrophotometer (Thermo Fisher Scientific Inc., Pittsburgh PA, USA). The RNA (1000 ng) was transcribed to cDNA with the "Revert Aid First Strand cDNA Synthesis Kit" (Thermo Fisher Scientific Inc, USA) according to the manufacturer's instructions.

Real-Time PCR

Progesterone Levels in Mouse Serum

RT-PCR was used to measure gene expression of mTERT which was normalized to the expression of the housekeeping gene: β-actin. cDNA (25 ng) was added to the reaction mixture which includes: mixture of primers (FW and RV), SYBR-Green and UPW. The primers used for PCR amplification of mTERT were: FW 5'-GAAAGTAGAGGAT-TGCCACTGGC-3' (SEQ ID NO.: 5) and RV 5'-CGTATGTGTCCATCAGCCAGAAC-3' (SEQ ID NO.: 6). The primers for β-actin were: FW 5'-GATGTATGAAGGCTTTGGTC-3' SEQ ID NO.: 7) and RV 5'-TGTGCACTTTTATTGGTGTG-3' (SEQ ID NO.: 8). Products were measured by ΔΔCt method in which mTERT gene is calculate relatively to β-actin.

Blood samples were taken from the sacrificed mouse and following centrifugation (3800 rpm, 10 min) the serum was sent to the clinical endocrinology laboratory (Soroka University Medical Center, Beer-Sheva, Israel) for determination of progesterone levels.

Results

Figure 2:
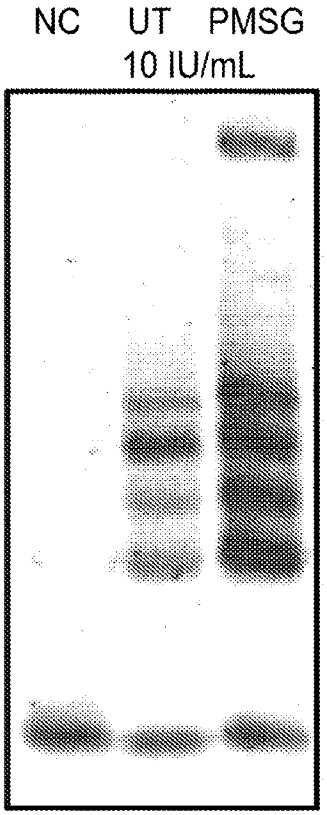
FIG. 2: Activation of telomerase expression by PMSG in rat granulosa cells.

Gonadotropin stimulation induces TERT expression and telomerase activity. FIG. 1 graphically plots the relative TERT Expression (%) as a function of increasing PMSG concentration. FIG. 2 shows the protein levels from a TRAP assay of granulosa cells treated with 10 IU/mL PMSG for 6 hours.

Figure 3:
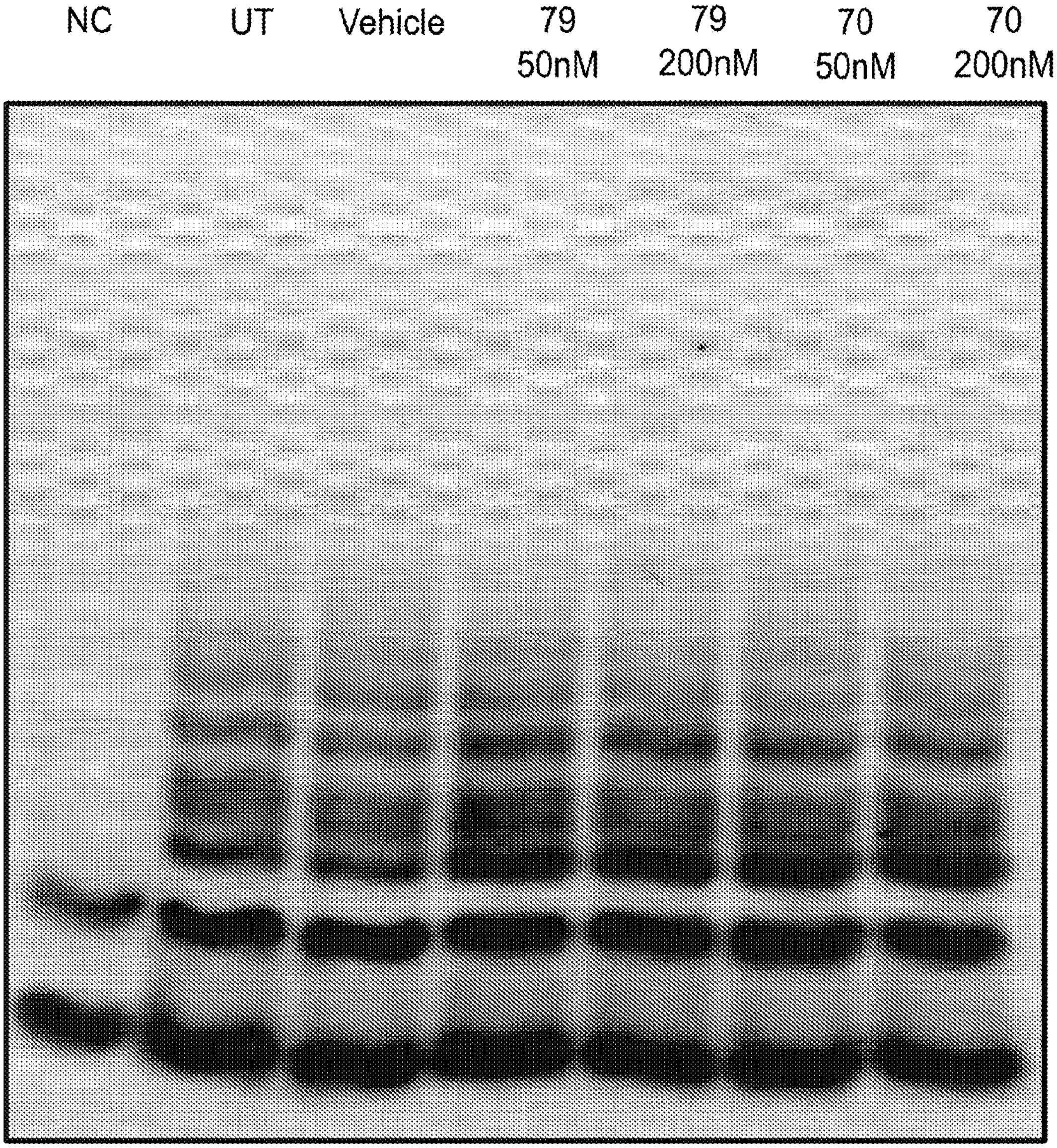
FIG. 3: Granulosa cells treated with two embodied compounds, compound 79 and compound 70, at 50 nM and 200 nM for 6 hours. Protein extracts served as the source for telomerase activity measurement using a TRAP assay.
Figure 4:
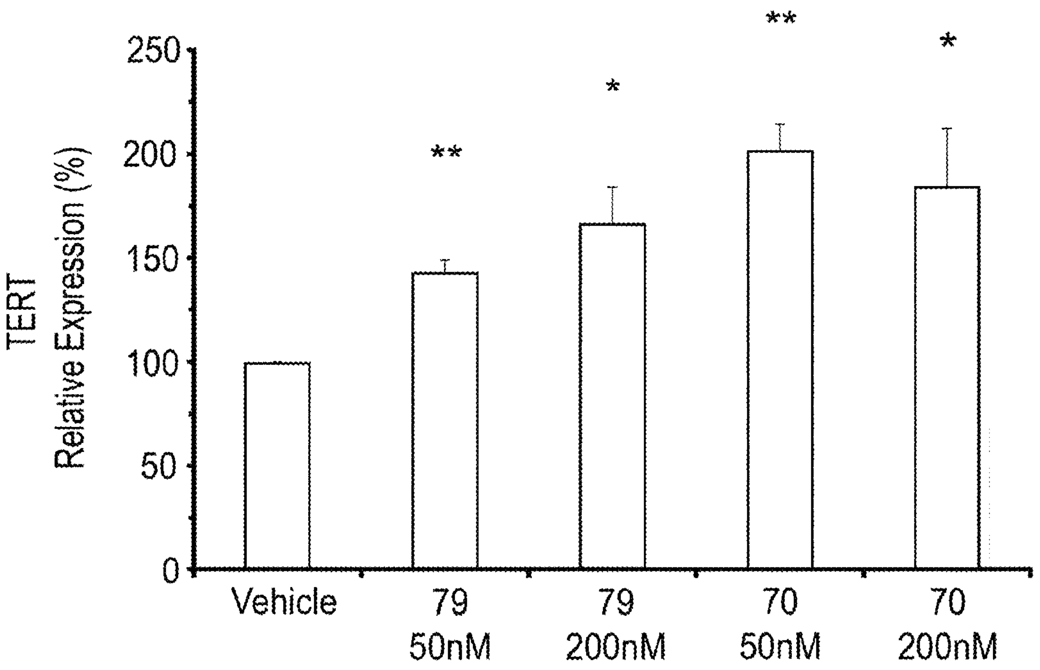
FIG. 4: Granulosa cells treated with two embodied compounds, compound 79 and compound 70, at 50 nM and 200 nM for 6 hours. RNA extracts assessed for TERT relative mRNA levels measurement by qRT-PCR with specific primers for TERT with β-actin serving as the reference gene. Results represents average+SE(n=3). Statistical significance determined by T-TEST *P-value<0.05**P-value<0.01.

The compounds increases TERT expression and telomerase activity (See FIGS. 3 and 4). Granulosa cells treated with two compounds for use in accordance with this invention (compounds 79 and 70), at 50 nM and 200 nM for 6 hours, respectively, when assayed for protein expression via TRAP and TERT relative mRNA levels via qRT-PCR support increased expression in a dose-dependent fashion. Surprisingly, Compound 70 further increased telomerase activity and expression in granulosa cells as compared to compound 79 (FIG. 3).

Figure 5:
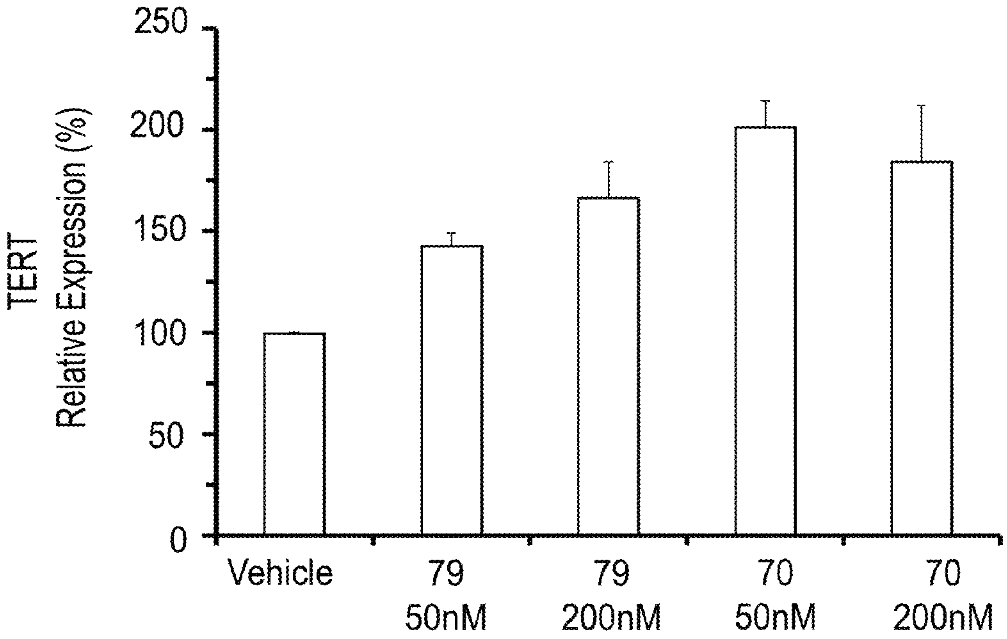
FIG. 5: Granulosa cells treated with two embodied compounds, compound 79 and compound 70, at 50 nM for 6 hours. RNA extract evaluated for StAr relative mRNA levels measurement by qRT-PCR using specific primers for StAr and β-actin serving as a reference gene. Results represents average+SE(n=3). Statistical significance determined by T-TEST *F ‘-value<<0.05.

Increasing TERT expression by the embodied compounds induced the expression of Steroidogenic acute regulatory protein (StAr). FIG. 5 shows granulosa cells treated with compounds 79 and 70, at 50 nM for 6 hours demonstrate increased expression of StAr.

Figure 6:
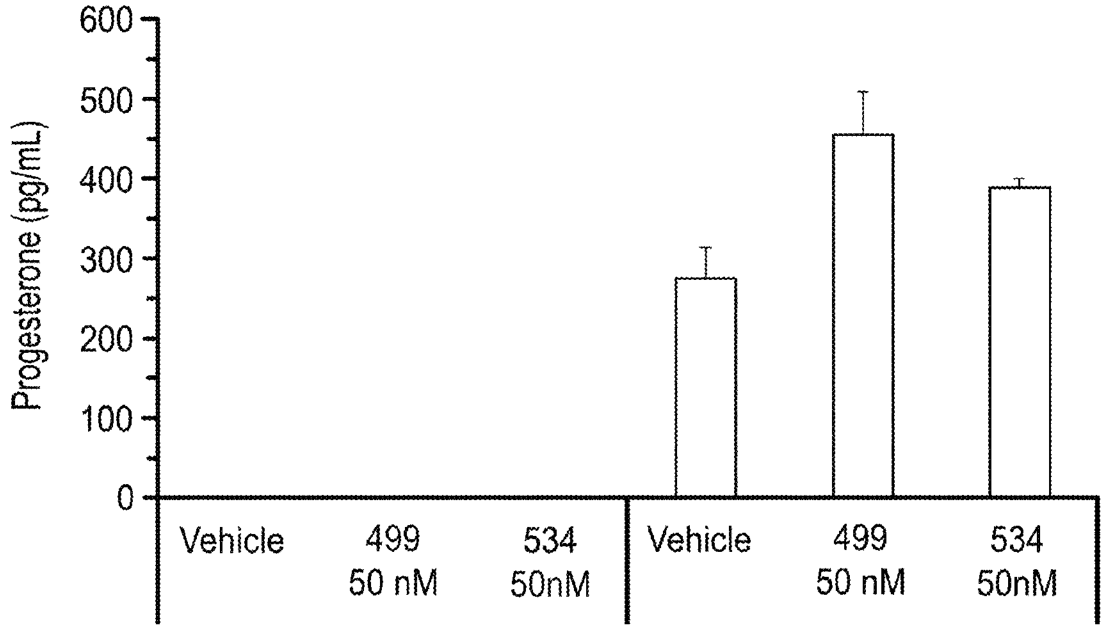
FIG. 6: Progesterone levels of granulosa cells treated with two embodied compounds, compound 79 and compound 70, at 50 nM with or without PMSG 1 IU/mL for 24 hours, by evaluation of cell-culture medium by radioimmunoassay (RIA). Value of zero represents undetectable amount of progesterone. Results represents average+SE(n=3). Statistical significance determined by T-TEST *P-value. 0.05.
Figure 7:
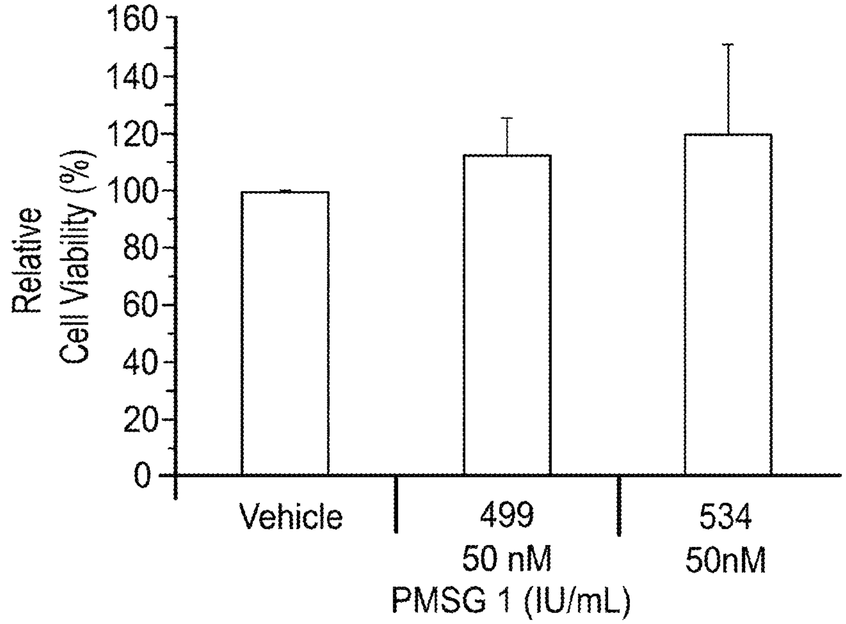
FIG. 7: Granulosa cell viability for samples treated with two embodied compounds, compound 79 and compound 70, in 50 nM with 1 IU/mL PMSG for 24 hours. Relative cell viability was measured by XTT proliferation assay. Results represents average+SE(n=3).

Increasing TERT expression by the embodied compounds increases progesterone levels specifically produced by granulosa cells after gonadotropin stimulation, while no significant effect on cell growth was detected. FIGS. 6 and 7 demonstrate FIG. 6 demonstrates Progesterone levels in Granulosa cells treated with compound 79 or compound 70, at 50 nM with or without PMSG 1 IU/mL for 24 hours as determined by radioimmunoassay (RIA). FIG. 7 demonstrates granulosa cell viability following treatment with the compounds 79 and 70, 50 nM with 1 IU/mL PMSG for 24 hours, as measured by XTT proliferation assay.

Taken together, it is demonstrated herein for the first time, that gonadotropin (FSH) stimulation in granulosa cells increased telomerase expression, which in turn contributes to the pathway by which FSH-controlled granulosa cells proliferate.

Increasing telomerase (by the administered compounds) in granulosa cells, affected the expression of genes involved in the stimulation pathway of FSH and the progesterone levels secreted by the cells, supporting the involvement of telomerase in steroidogenesis in granulosa cells and the ability to positively affect female fertility thereby.

Example 3

The Effect of Embodied Compounds of this Invention on Ovulation In Vivo

Materials and Methods

Female ICR mice at least 3 months old were administered embodied compounds of this invention (Compound 79 and Compound 68) (6 mg/Kg) or DMSO alone (0.5%) by subcutaneous administration. Vaginal smears were taken at baseline and at 12 hours following the administration to determine estrous cycle stage and mice were then sacrificed.

The ovaries were weighted; one was taken for protein extraction for measuring telomerase activity by TRAP assay, and the other one for the histological examination using hematoxylin-eosin staining of the ovary and its follicles.

Histological Analysis

The mice ovaries were removed and fixed with 4% paraformaldehyde overnight, dehydrated in increasing ethanol concentrations to xylene, and embedded in paraffin. A rotary microtome was used to produce 5 μm sections, which were mounted on Superfrost plus slides. The sections were dried and heated at 37° C. overnight and stored in dry place. Paraffin-embedded sections were deparaffinized in xylene and rehydrated in decreasing concentrations of ethanol. Then the sections stained with hematoxylin-eosin or subjected to immunochemical and Immunofluorescent assays [Liani-Leibson, K., I. Har-Vardi, and E. Priel, Inhibition of topoisomerase I by anti-cancer drug altered the endometrial cyclicity and receptivity. Curr Mol Med, 2014. 14(1): p. 141-50].

Immunofluorescence

All sections were initially treated with Antigen retrieval solution; the sections were heated for 5 min in 10 mM sodium citrate solution pH=6. Nonspecific binding was blocked by incubating the sections with 3% BSA. Monoclonal mouse anti-PCNA, clone PC 10 sc-56 (Santa cruz Dallas, Texas USA) diluted 1:200 in PBS+3 BSA was used as the primary antibody. Sections were incubated with primary antibody overnight at 4° C. The next day, sections were washed with PBS and PBS contains 0.1% TWEEN 20 (Sigma) The secondary anti mouse antibody (cy3) (Jackson PA, USA) was applied for 2 hours at room temperature. The sections were washed with PBS and PBS contains 0.1% TWEEN 20 and DAPI (Sigma) was applied for 10 min. Finally, sections were washed, and covered by water-based mounting medium. PCNA labeling was examined using Panoramic midi (3D Histech) device.

Pairings Between Male and Female Mice

Female ICR mice were treated with a single s.c. injection of Compound 79, Compound 68 and Compound 70 6 mg/kg or with DMSO 0.5%. Immediately after the injection the female mouse was put into a cage of the male mouse, after 14 days female mouse was sacrificed and the number of embryos in the uterus were counted.

Other methods were as described hereinabove in Example 2.

Results

Figure 8:
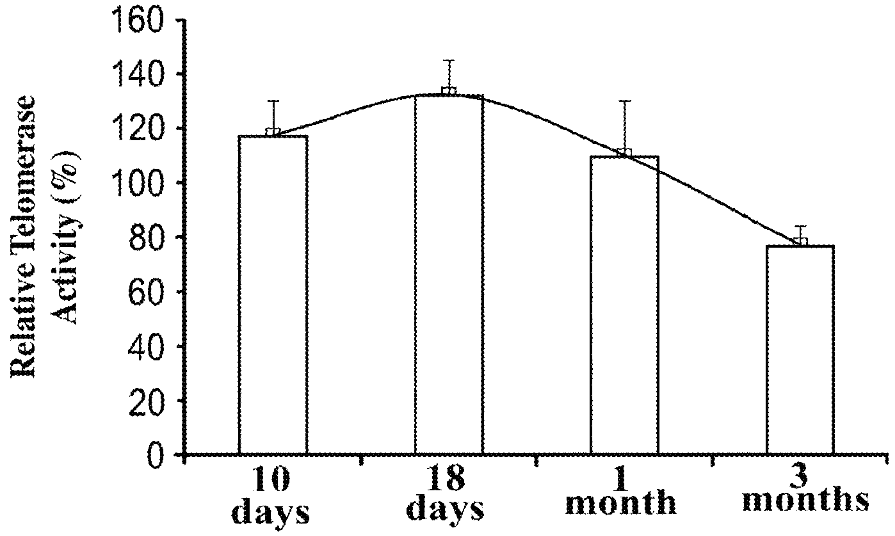
FIG. 8: Telomerase activity in mouse ovary at different mouse ages, as quantified by TRAP assay of mouse ovary at various ages (10 days, 18 days, 1 month and 3 months old) by densitometry analysis using the EZquant software and calculated as % of a constant positive control, (mean±s.e.m.; n=12 mice).
Figure 9:
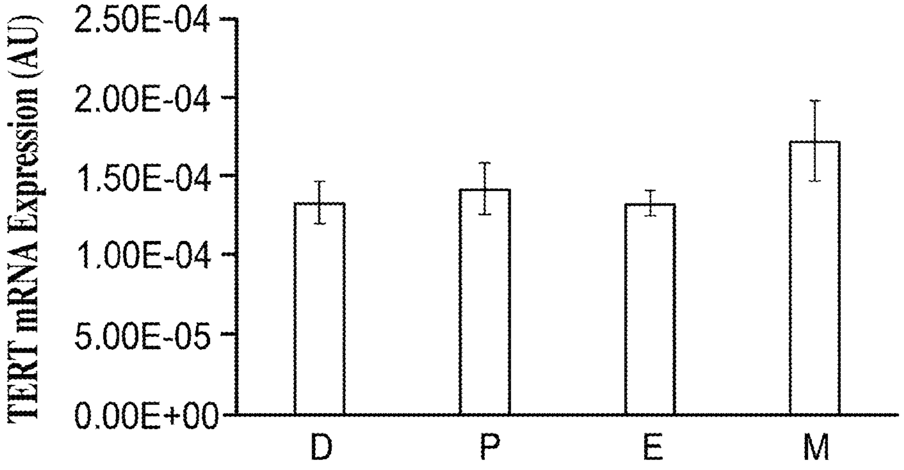
FIG. 9: TERT expression in ovaries derived from 3 months old mice at various estrous stages. Total RNA was prepared from the ovaries of 3months old mice at the various estrous stages and qRT-PCR was performed with the appropriate primers. Data are mean±s.e.m.; n=12.
Figure 10A:
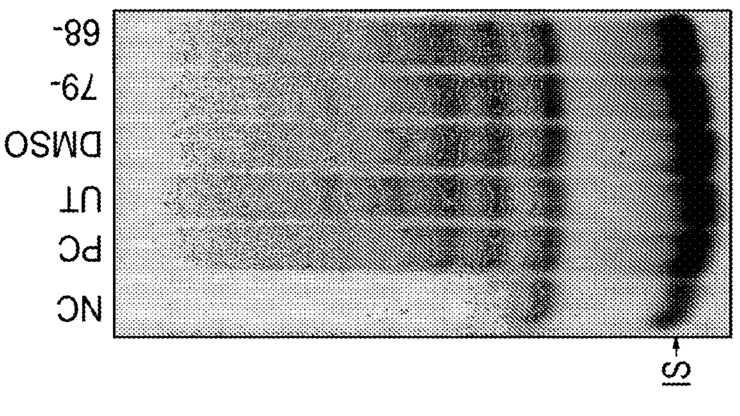
FIGS. 10A-E: Telomerase activity in mouse ovary following treatment with the indicated compounds. Mice were injected s.c. with Compound 79 or 68 or DMSO. Twelve hours after treatment, proteins extract were prepared from mice ovary and 1 microg was added to the TRAP specific reaction mixture (FIG. 10A a representative picture). Quantification of telomerase activity (by densitometric analysis of the TRAP assay DNA products using the EZquant software) in ovary proteins extract derived from mouse at different ages FIG. 10B. 10 days, FIG. 10C. 18 days, FIG. 10D. 1 month FIG. 10E. 3 months. Symbols: PC-positive control (proteins extract of cancer cells). Negative control (NC) contained CHAPS buffer instead of proteins extract. IS=internal standard. The results are mean #s.e.m.; n=48 mice) T test: * $p<0.05$ relative to DMSO.
Figure 10B:
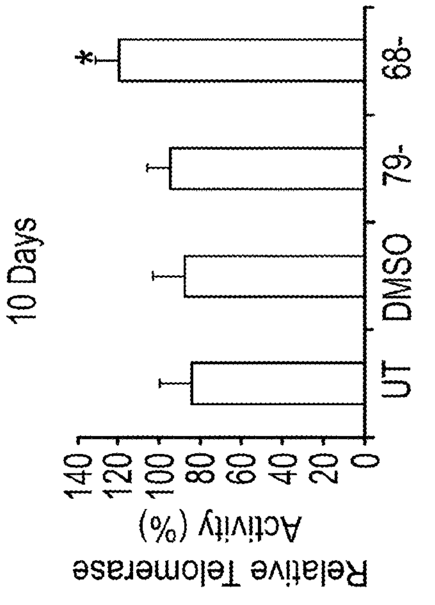
Figure 10C:
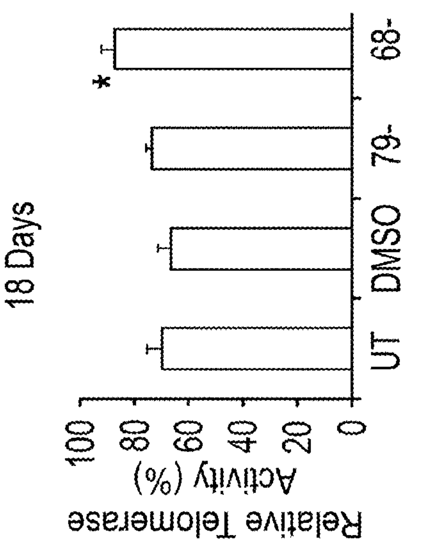
Figure 10D:
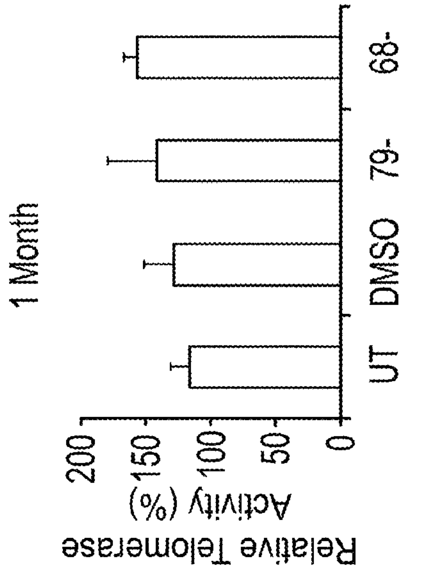
Figure 10E:
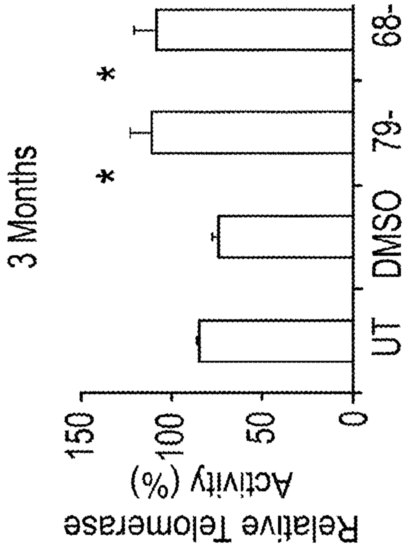

Telomerase activity peaks at the age of 18 days in ovary of female mouse. Telomerase activity in protein extracts derived from ovary obtained from mice at various ages: 10 days, 18 days, 1 month and 3 months (n=12, 3 per group) was determined by modification of the TRAP assay [Grin, Y., T. Admoni, and E. Priel, Telomerase activity in the various regions of mouse brain: non-radioactive telomerase repeat amplification protocol (TRAP) assay. J Vis Exp, 2014 (91): p. e51865] and quantified by densitometric analysis using the EZquant software as previously described [Eitan, E., et al., Novel telomerase-increasing compound in mouse brain delays the onset of amyotrophic lateral sclerosis. EMBO Mol Med, 2012. 4 (4): p. 313-29; Tichon, A., et al., Oxidative stress protection by novel telomerase activators in mesenchymal stem cells derived from healthy and diseased individuals. Curr Mol Med, 2013. 13 (6): p. 1010-22; Tichon, A., et al., Telomerase activity and expression in adult human mesenchymal stem cells derived from amyotrophic lateral sclerosis individuals. Cytotherapy, 2009. 11 (7): p. 837-48]. The results depicted in FIG. 8 show that telomerase activity in the ovary declines with age, and the peak of the activity was observed at 18 days old. To examine whether the level of telomerase expression is influenced by the stage of estrous cycle in the mouse ovary, we determined the stage of the estrous cycle of the female mouse (3 months old), prior to sacrificing, using the common vaginal smears method. Total RNA was extracted from the ovaries, cDNA was prepared and Real-Time PCR was performed with the appropriate mTERT primers. The results in FIG. 9 show that the expression of TERT in mouse ovary did not significantly changed through the estrous cycle Administration of embodied compounds increased telomerase activity in the mouse ovary at various ages. Mice of different ages were assigned to groups (10 days, 18 days, 1 month and 3 months) and treated with Compound 79, Compound 68, DMSO as a vehicle control and untreated (n=48, 3 mice per group). Compound 79, and Compound 68 (6 mg/Kg) or DMSO (0.5%) were injected subcutaneously in mice and after 12 hours the mice were sacrificed, the ovaries were removed, and proteins extract used for measuring telomerase activity by TRAP assay. A single dose of Compound 68 significantly increased telomerase activity (up to 1.5 fold) at all the examined ages (FIGS. 10A-E) while Compound 79 significantly increased telomerase activity only in the ovary of 3 months old mouse (10E).

Figure 11B:
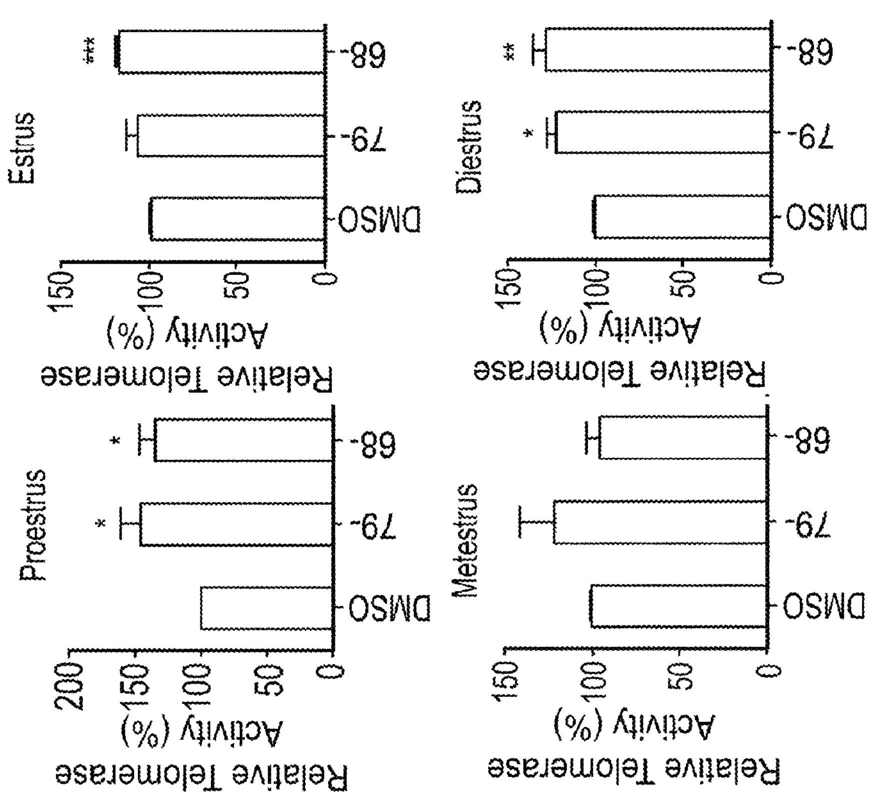
FIGS. 11A-B. The compounds of this invention increase telomerase expression (FIG. 11A) and activity (FIG. 11B) in mouse ovary at all estrous stages. Female mice at the various estrous stages were untreated or treated with a single injected (s.c.) of: 0.5% DMSO, Compound 79 or 68 at 6 mg/kg. The mice were sacrificed 12 hrs post treatment and the ovaries were removed, A-total RNA was prepared followed by cDNA preparation and analysis by qRT-PCR with the appropriate primers. B-protein extracts were prepared and 1 μg of proteins was analyzed for telomerase activity using the TRAP assay. The telomerase DNA products were quantified by densitometric analysis with the EZquant software and calculated as % of a constant positive control. The results are mean±SE, n>3 mouse per group Ttest, *$p<0.05$,  $p<0.01$, * $p<0.001$ relative to DMSO.
Figure 11A:
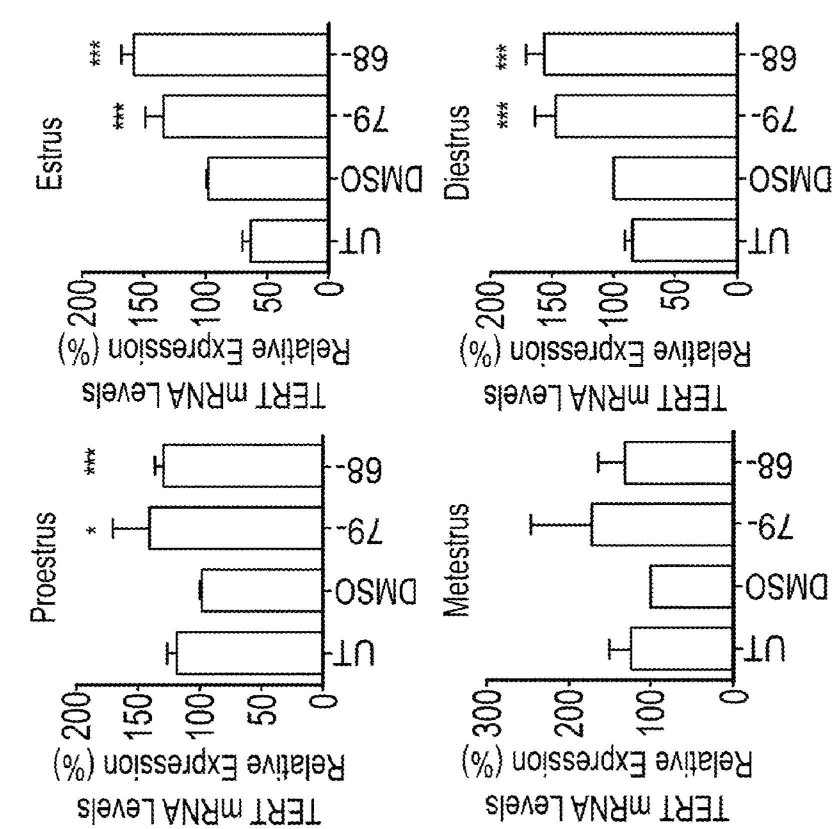

The compounds of this invention increase telomerase expression and activity in mouse ovary at all estrous stages. To determine if the increase of telomerase expression and activity by the compounds depends on the estrous stages we treated mice with a single dose of the indicated compounds at the various Estrous stages as described above. Twelve hours post treatments the mice were sacrificed, the ovaries were removed: one was taken for protein extraction for measuring telomerase activity by TRAP assay, and the other one for RNA extraction for measuring the level of TERT mRNA expression using qRT-PCR. In mouse ovary at proestrus, estrus and diestrus stages, the compounds significantly increased telomerase expression (up to 1.5 fold) (FIG. 11A) and telomerase activity (FIG. 11B). When the compounds were administered at the metestrus stage they increase telomerase expression and activity but not significantly.

Activation of telomerase increased ovarian size and weight at each stage of estrous cycle and accelerate the estrous cycle. The ovaries of the mice from the above described experiments were weighted prior to the various analysis. We observed an increase (of up to 40%) in mouse ovary's size and weight following treatment with the indicated compounds compared to untreated and DMSO, at all the estrous cycle stages (FIGS. 12A, B). To examine the biological effects of increasing telomerase in the ovary by the compounds on the estrous cycle, mice (3-5 months old) were untreated or treated with the compounds (a single dose of Compound 79, Compound 68) or the vehicle (0.5% DMSO) at the various stages of the estrous cycle, and 12 hrs after treatment the stage of the Estrous cycle was determined by the component of cells in the Vaginal smears. The results presented in FIGS. 13A-D show that mice injected with a single dose of the compounds in the proestrus (P) or estrus (E) stages were found to b, 12 hrs post treatment, in the metestrus stage. While the control untreated or vehicle treated mice were after 12 hrs at the estrus stage, as expected. No changes in the estrous cycle stage, 12 hrs post treatment, were observed when the compounds were injected at the diestrus or metestrus stages.

Figures 13A, 13B, 13C, 13D:
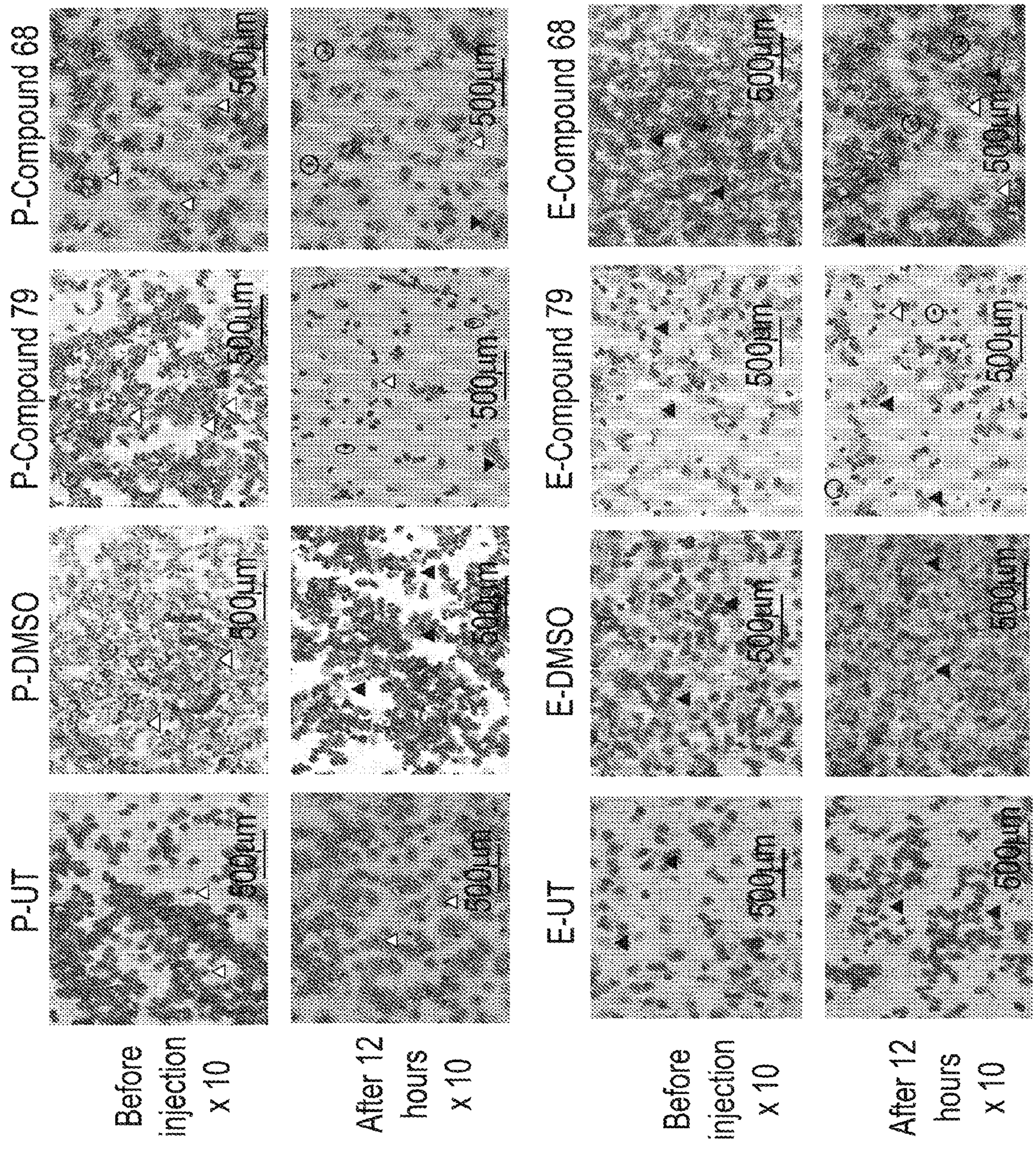
FIGS. 13A-D: Vaginal smears at proestrus and estrus stages before and after 12h of treatment with the indicated compounds. Vaginal smears were taken from female mice following by s.c. injection with DMSO, Compound 79 or 68.

The embodied compounds promote and enhance ovulation, as evidenced by changes in vaginal smears at proestrus and estrus stages before and after 12h of treatment (FIGS. 13A=D). Vaginal smears were taken from female mice following by s.c. injection with DMSO, Compound 79 and Compound 68, as indicated. (A). Before treatment proestrus stages (A), estrus stages (C). After 12 hours of treatment the vaginal smears were taken again, proestrus stages (B), estrus stages (D). The vaginal smears were stained by crystal violet.

Figures 14A, 14B, 14C, 14D:
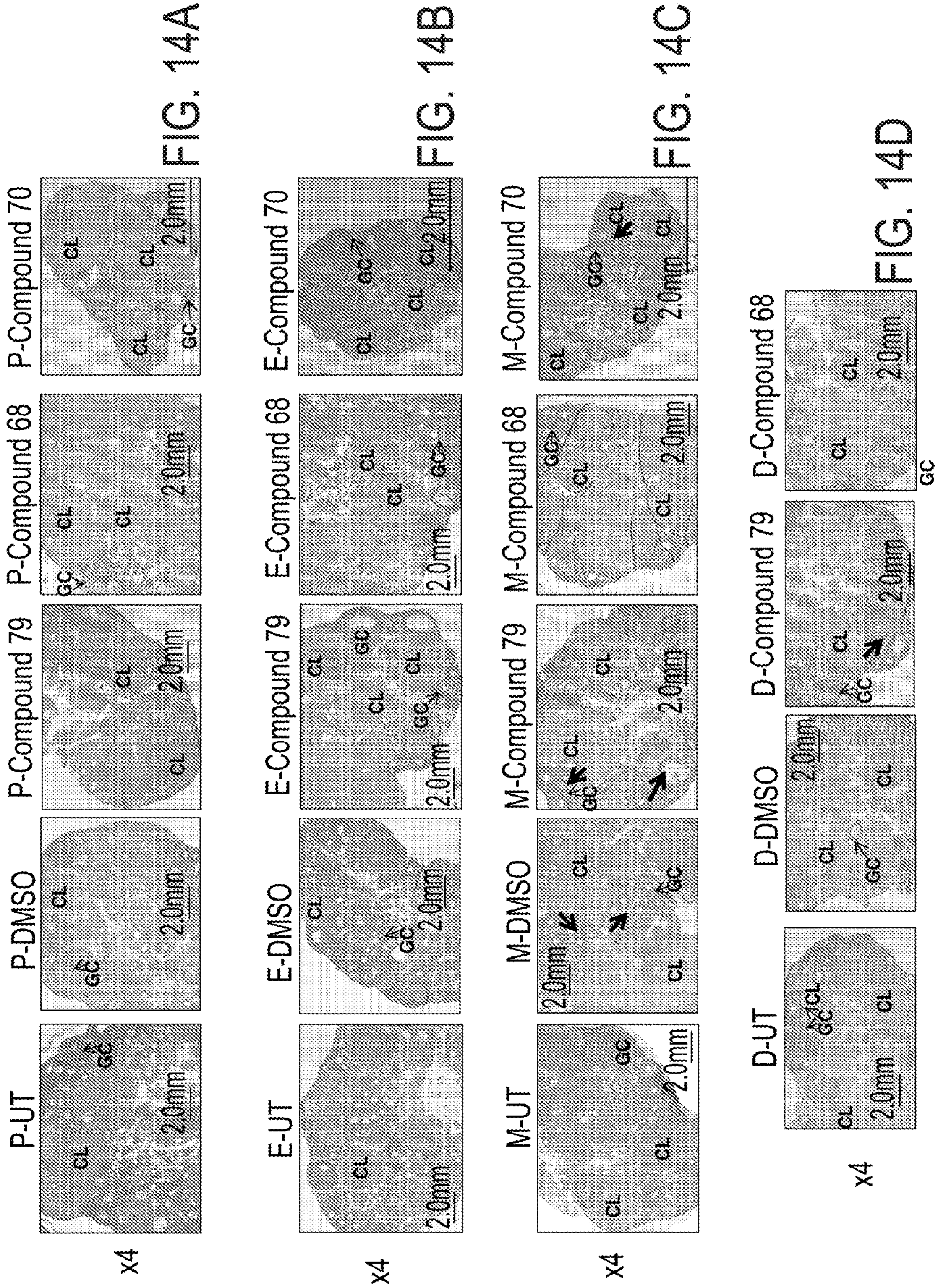
FIGS. 14A-D: Hematoxylin-eosin staining of mice ovary at the various estrous stages. Mice at the various estrous stages (FIGS. 14A-D respectively) were injected s.c. with DMSO, or with one of compounds 68, 70 and 79, as indicated. After 12 hours the mice were sacrificed and ovaries were removed and fixed with formaldehyde. The tissues were stained with Hematoxylin-eosin and visualized by light microscopy x4. CL-corpus luteum, GC-granulosa cells, n>3 per group.

Histological analysis of the ovaries derived from 3 month old mice treated with the compounds as described extended these findings. The mice were divided to groups according to their estrous cycle stages (P, E, M. D). At each stage of the estrous cycle mice were untreated or treated with a single dose (6 mg/Kg) of Compound 70, 79, Compound 68, or DMSO 0.5%). Twelve hours post treatment the mice were sacrificed, the ovaries were removed for the histological examination using hematoxylin-eosin staining. As can be seen in FIGS. 14A-D, treatment of mice at the pro-estrus (P) and estrus (E) stages with Compound 70, 79 or Compound 68 caused, 12 hrs after treatment, more corpus luteum (CL) than in the control group (UT, DMSO) suggesting an increase of ovulation (FIGS. 14A, 14B).

Treatments at met-estrus (M) stage demonstrate, 12 hours post treatment, many corpus *luteum* (CL) in all of the treatment groups, but in Compound 70, 79 or Compound 68 treated mice more developed follicles (white arrow) and plurality of layers of granulosa cells (GC) around the oocytes were seen; while in the control groups mostly primordial follicles (blue arrow) were detected (FIG. 14C). Treatments at the Di-estrus (D) stage with Compound 68 shows 12 hours post treatment, a plurality of corpus luteum (CL) and Compound 79 shows multiple layers of granulosa cells (GC) around the oocytes (FIG. 14D).

Figure 15A:
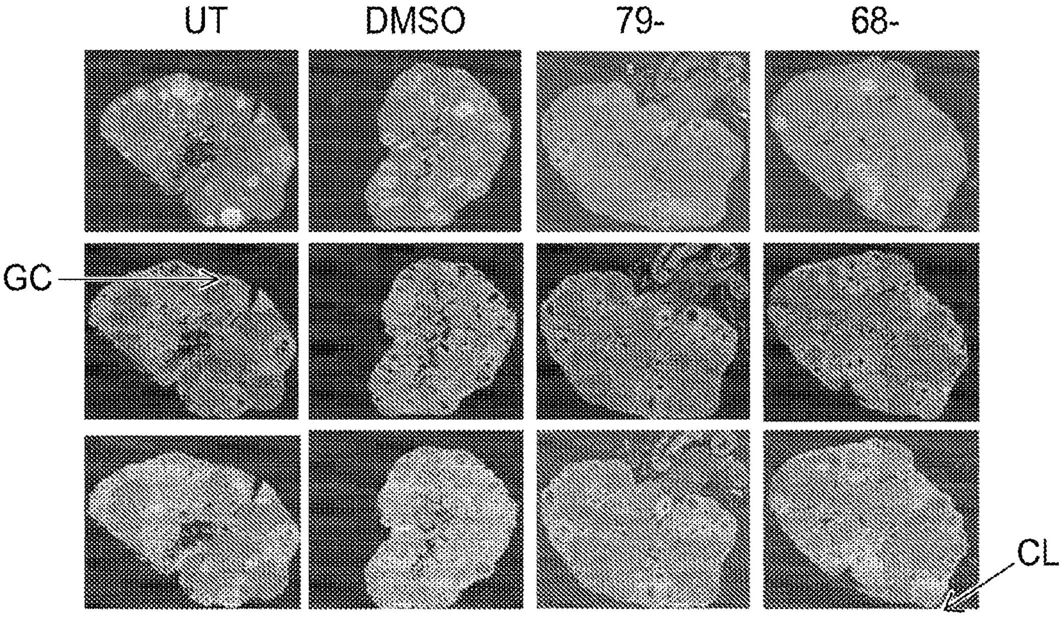
FIGS. 15A, B: PCNA staining of mouse ovary following treatments with embodied compounds: representative pictures. Mice at the estrus stage (FIG. 15A) or at the metestrus stage (FIG. 15B) were injected s.c. with DMSO, or with one of Compound 79 or 68. After 12 hours the mice were sacrificed and the ovaries were removed and fixed with formaldehyde. The tissues were subjected to immunofluorescence analysis using anti-PCNA antibody. Symbols: CL-corpus luteum, GC-granulosa cells.
Figure 15B:
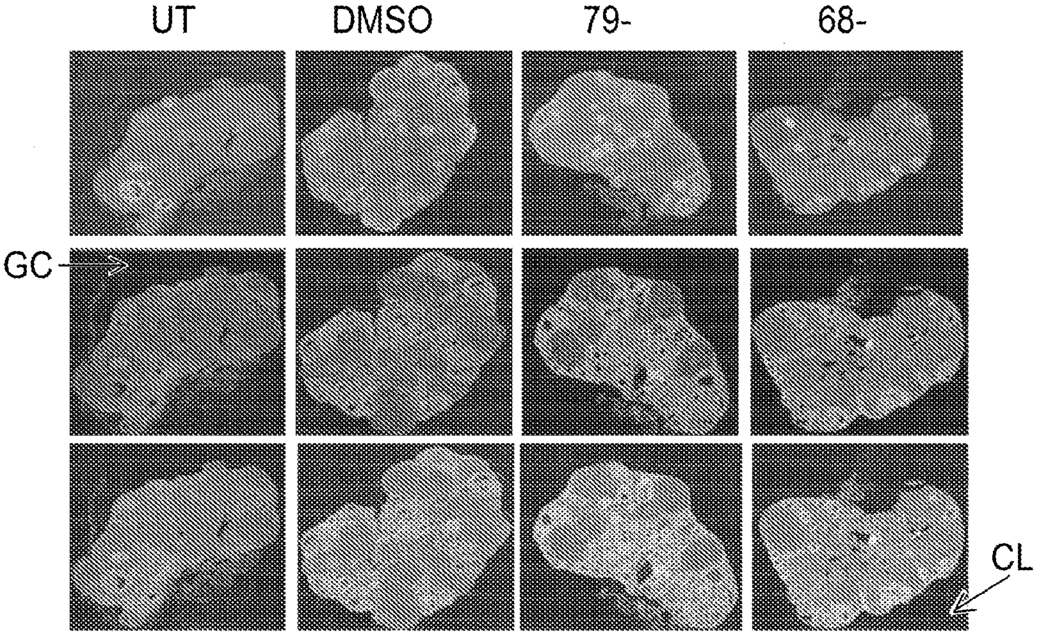
Figure 16A:
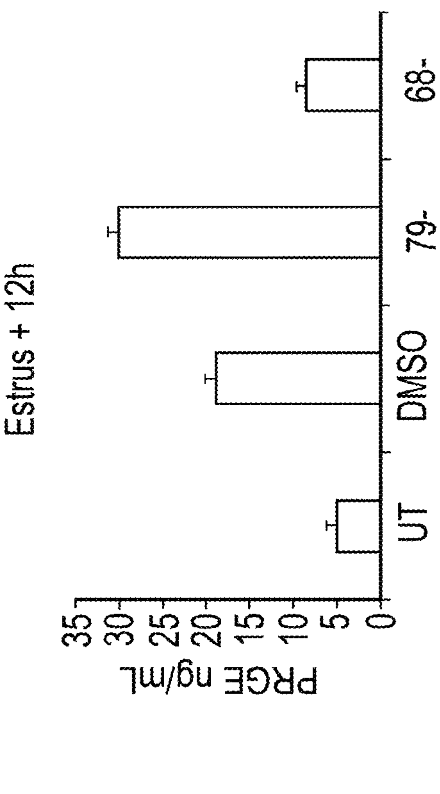
FIGS. 16A-D: Progesterone concentrations in the plasma of female mouse 12 hours post treatment with the embodied compounds. Mice at the various estrous stages were treated with the indicated compounds or vehicle. Mice were sacrificed 12 hrs post treatment and Blood samples were taken and the concentration of progesterone was measured as described (mean±s.e.m.; n=34 mice).
Figure 16B:
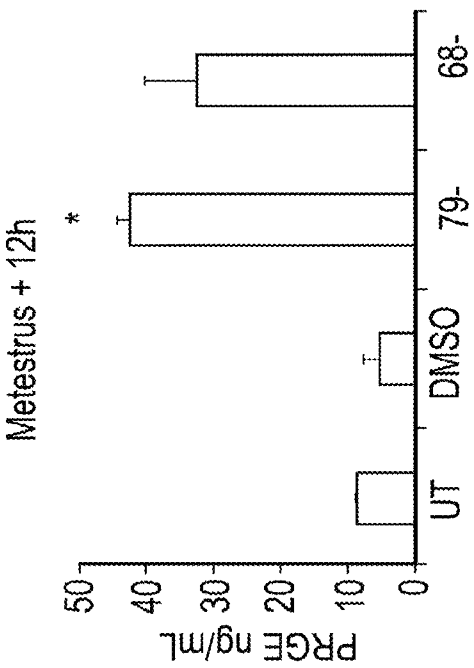
Figure 16C:
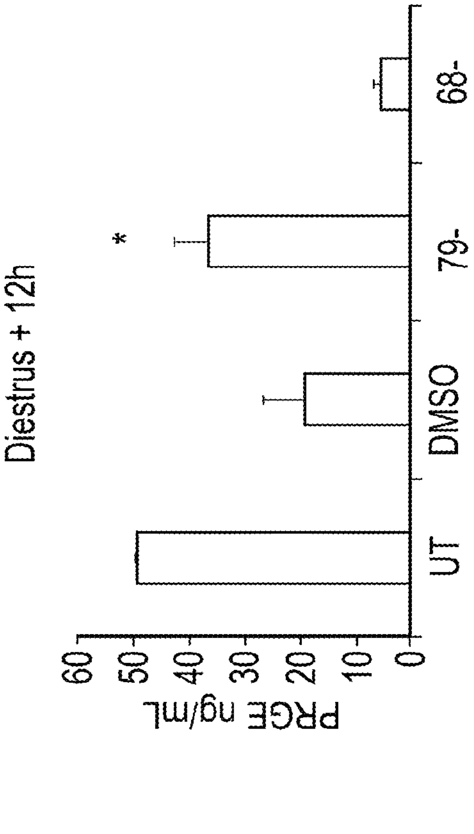
Figure 16D:
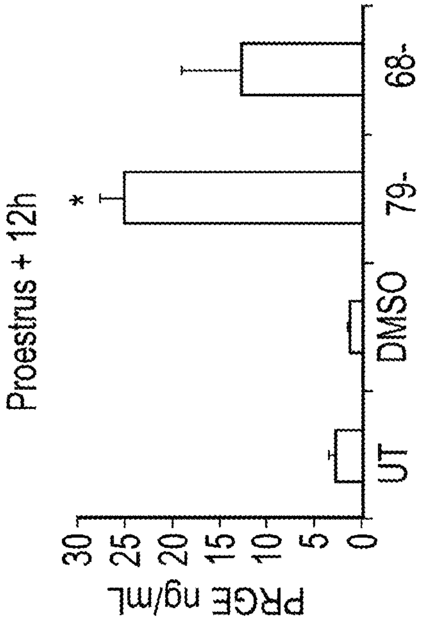

Examination of cells proliferation in the ovary following the various treatments was performed using anti-PCNA antibody, a known proliferation marker. The results revealed that untreated or vehicle treated mice at the estrus stage demonstrated significant PCNA staining in the GC of the various follicles (FIG. 15A), while following treatment the appearance of CL with less PCNA staining of GC was detected, which is compatible with the met-estrus stage of the ovary (FIG. 15A). When the mice at the met-estrus stage were treated with the embodied compounds (FIG. 15B) the amount of GC in the follicles that demonstrate PCNA staining increased compared to untreated or vehicle treated mice suggesting the activation of follicles by the compounds.

The compounds of this invention induced secretion of progesterone. To determine if the increase in the number of CL observed after treatment with the compounds produced functional corpus luteum that secretes progesterone, blood samples were taken 12 hours post treatments from the sacrificed mouse and the serum was analyzed for progesterone levels. The results showed that 12 hrs post treatment a significant increase (up to 5 folds compared to DMSO or UT) in the secretion of progesterone in mice that were treated with Compound 79 at P, E, and M stages of the estrous cycle was observed (FIG. 16). Treatment with Compound 80 demonstrated an increase in progesterone only when it was administered at the met-estrus and pro-estrus stages. These data are compatible with the above described results which demonstrate that differential treatment and general treatment with the indicated compounds at pro-estrus and estrus stages accelerates the appearance of the met-estrus stage that according to the literature shows a high secretion of progesterone.

Figure 17:
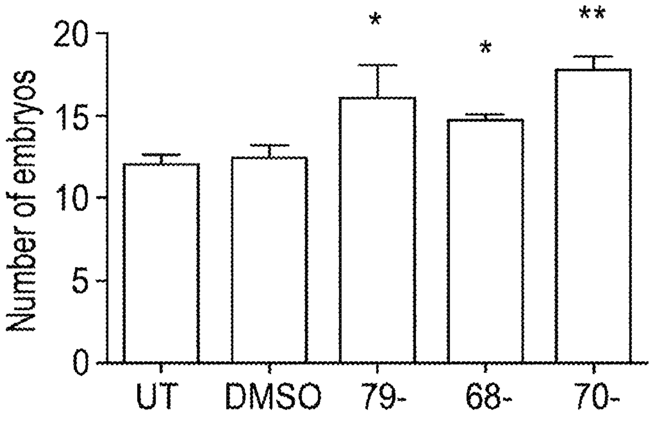
FIG. 17: The compounds in accordance with this invention increase the number of embryos. ICR mice were treated with a single s.c. injection of the indicated compounds, 6 mg/kg or with DMSO 0.5%. Immediately after the injection female mouse was put into a cage of the male mouse, after 14 days female mouse was sacrificed and number of embryos counted. The results are mean±SE, n>3 mouse per group. t-test, *$p<0.05$, ** $p<0.01$, relative to DMSO.

The compounds of this invention increase the number of embryos. The histological examination of ovarian tissue showed a high numbers of corpus *luteum* following treatment with the embodied compounds, relatively to untreated mouse at the same estrous cycle stage, which indicates increase in the number of ovulated oocytes. To examine if the oocytes ovulated following treatments are viable, we tested the number of embryos generated following the various treatments: Compound 79 or Compound 68, DMSO and untreated, and Compound 70. Following a single s.c. injection of the respective compound (6 mg/kg) or DMSO (0.5%) single female mice were put into a cage containing a male mouse. Fourteen days after, the female mice were sacrificed and the number of embryos in the uterus of each treated mouse was determined. The data presented in FIG. 17 show that the number of embryos in the treated mice significantly increased (up to 50%) compared to the controls (DMSO or UT) mice.

Taken together, this example shows that telomerase activity is present in mouse ovary, which decreases with age, peaking at the age of 18 days, while the level expression of TERT doesn't seem to be appreciably modified at each stage of estrous cycle.

In contrast to naive mice, mice treated with the embodied compounds of this invention demonstrated increased telomerase activity at all ages, in particular at the age of 3 months that is considered peak fertility age in female mice. Increasing telomerase activity shows more proliferation of granulosa cells and more development of antral and pre-ovulatory follicles, in addition to high ovarian weight and size. We observed that the embodied compounds increase telomerase expression and activity significantly in mouse ovary at all estrus stages but not at met-estrus, that incretion by the embodied compounds in estrus and pro-estrus stages accelerate the appearance of the met-estrus stage according to typical vaginal cells and increase the numbers of corpus *luteum* follicles at all stages after 12 hours of single treatments. The embodied compounds also have an effect on secretion of progesterone as in luteal phase, regardless of estrus cycle stages. After the pairings we observed that the compounds increase the number of embryos, supporting that the compounds accelerate the ovulation process and developed more pre-ovulatory follicles with mature oocytes.

The embodied compounds thus clearly improve and promote female fertility and contribute greatly to increasing fertility therapeutic strategies, and in some aspects are particularly suitable in supporting IVF treatments, in consideration of the data provided in the next example, as well.

Example 4

Variations in Telomerase Activities in Granulosa Cells Derived from Women Undergoing IVF Procedures

Background, Materials and Methods

Although the telomerase (Telo) enzyme has a catalytic subunit with reverse transcriptase (RT) activity-TERT, which performs de novo synthesis of one strand of the telomeric DNA in its canonic role, there are known non-canonical roles, as well, which include cellular proliferation, gene expression and regulation, mitochondrial function like protection against oxidative stress and apoptosis, signaling pathways, genesis of double-stranded RNAs in order to silence mitochondrial RNAs. Telomerase is repressed in somatic cells of long lived organisms, but detected in human germ cells. The enzyme is an essential nuclear enzymes that exists in all living organisms, in which it plays a crucial role in genomic stability. Little is known, however, about the enzymes in developing granulosa cells (GCs). Even less is understood in terms of the modulation of same in conditions impacting infertility, such as, for example, in IVF therapy.

To evaluate the role/modulation of the enzyme during IVF treatment, GCs were collected from follicular liquid of women undergoing IVF after the oocyte was taken for IVF procedures. GCs were separated under a microscope and washed with saline. Examination of telomerase activity was determined in extracts derived from patient's GCs (WC-whole cells and DB-DNA-bound fraction) using the TRAP assay. Determination of the expression of telomerase in the various extracts was obtained by examination of the level of TERT protein using a specific ELBA kit.

Results

Figure 18A:
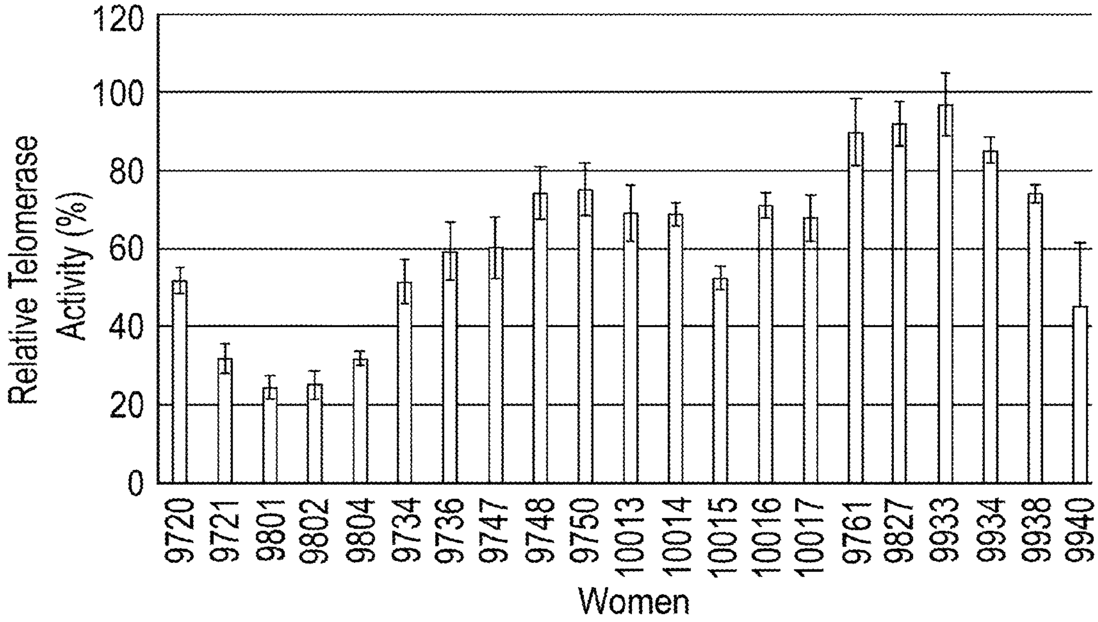
FIGS. 18A-C: Telomerase activity in Granulosa cells obtained from Woman undergo IVF procedure. The telomerase DNA products obtained by the TRAP assay FIG. 18A-for 0.5 μg protein of Whole cell (WC) extract and FIG. 18B-0.1μg protein of DNA bound (DB) extract, were analyzed by densitometry using the EZquant software. Telomerase activity was calculated as % of the data obtained for a permanent positive control (protein extracts from glioblastoma cells). The results are means±SD of at least 3 independent TRAP assays.
Figure 18B:
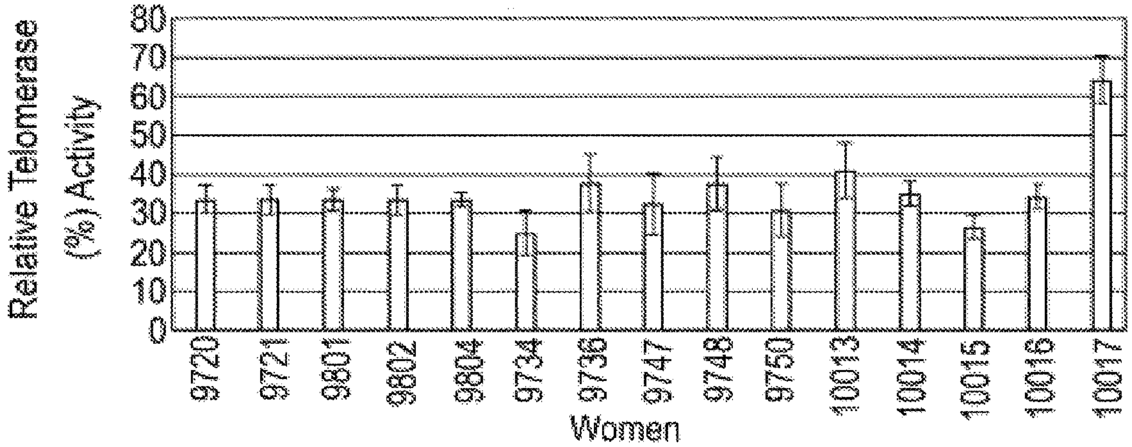
Figure 18C:
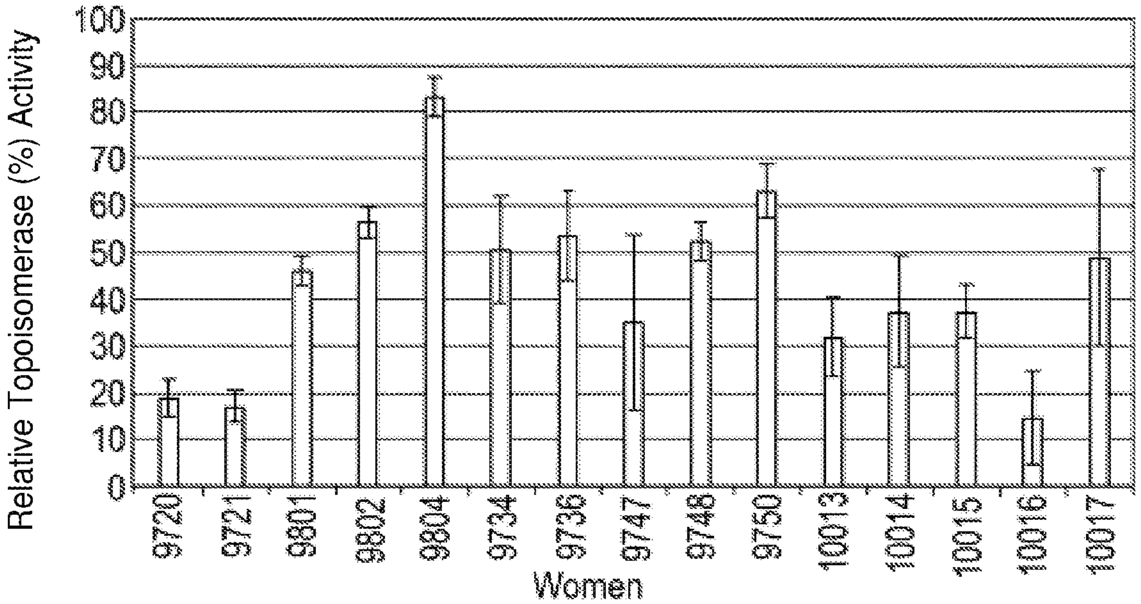

FIGS. 18A and B relate to the relative Telomerase activity and FIG. 18C topoisomerase activity in women undergoing IVF. The telomerase DNA products obtained by the TRAP assay (FIG. 18A-for 0.5 μg protein of WC extract and FIG. 18B-0.2 μg protein of DB extract), were analyzed by densitometry. Telomerase activity was calculated as % of the data obtained for a permanent positive control (protein extracts from glioblastoma cells). The results are means±SD of at least 3 independent TRAP assays.

Figure 19A:
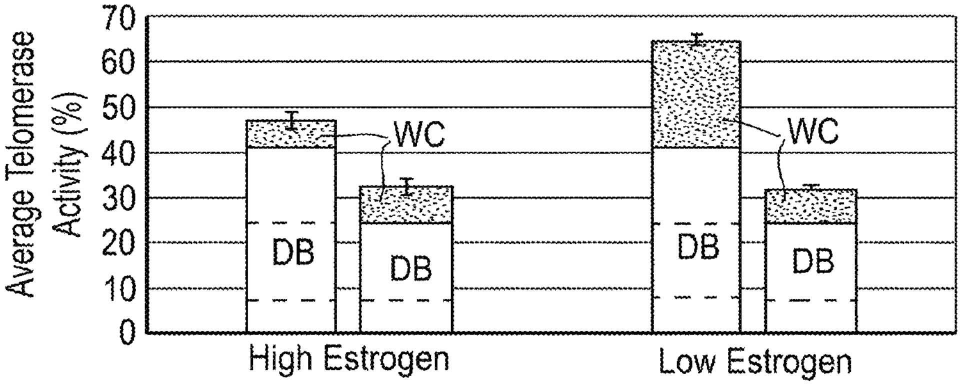
FIGS. 19A, B Telomerase (A) and topoisomerase (B) activity as correlated with Estrogen levels.
Figure 19B:
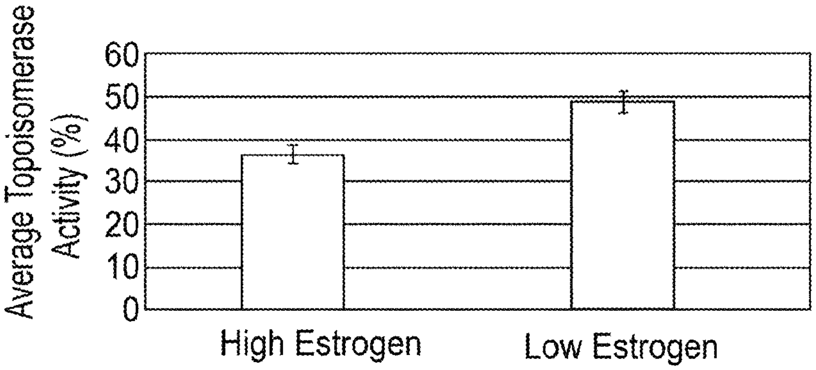

There is a correlation between high and low blood estrogen levels, and average enzymes activities. Telomerase (telo) activity was evaluated in FIGS. 19A, B: (A) (WC: $p=0.01$, DB: $p=0.42$) $n=9$ for high, $n=12$ for low,. The average enzyme activity of telo (in WC and DB extracts) was calculated for high and low estrogen levels. High estrogen level was determined as <1500 ng/ml.

Figure 20A:
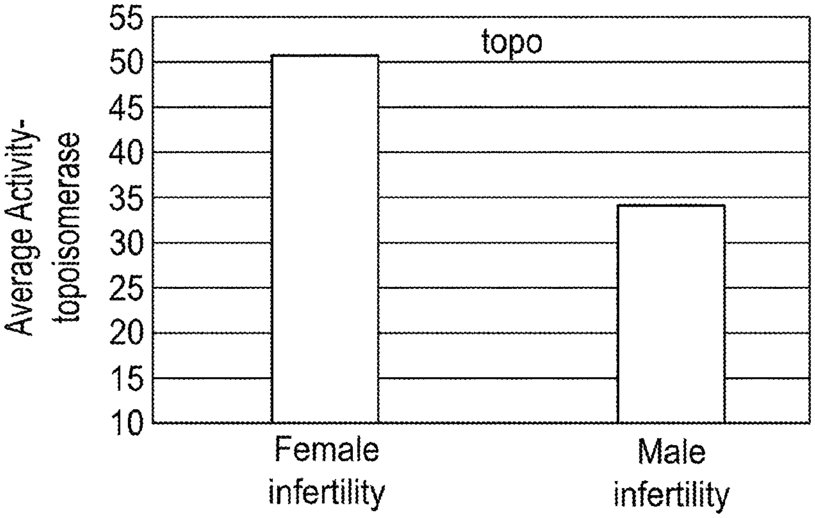
FIGS. 20A, B: Correlation between diagnosis of infertility and Telo/activities, n=9 for female infertility, n=12 for male infertility.
Figure 20B:
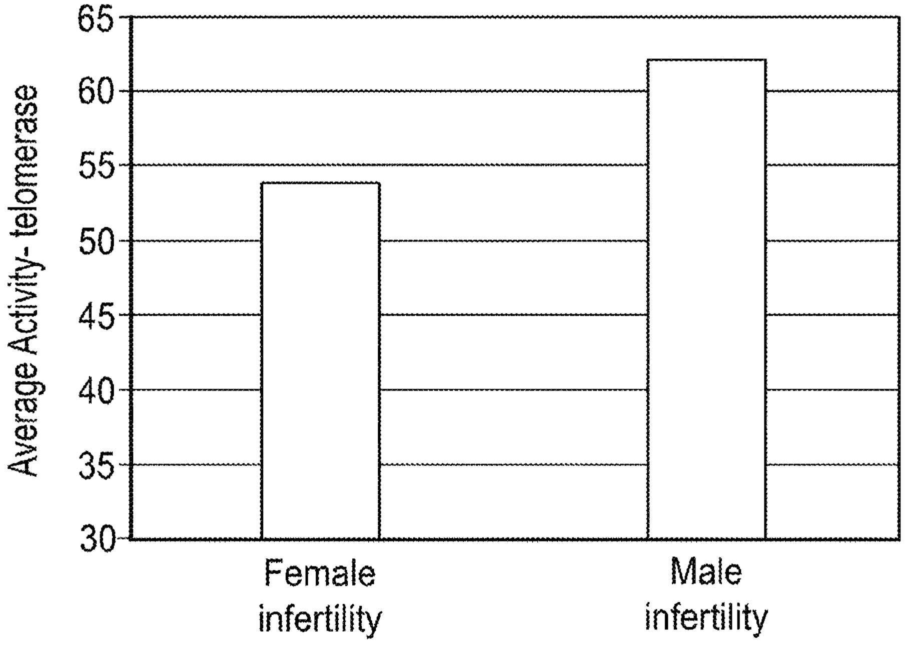
FIG. 20B telomerase average activity.
Figure 21A:
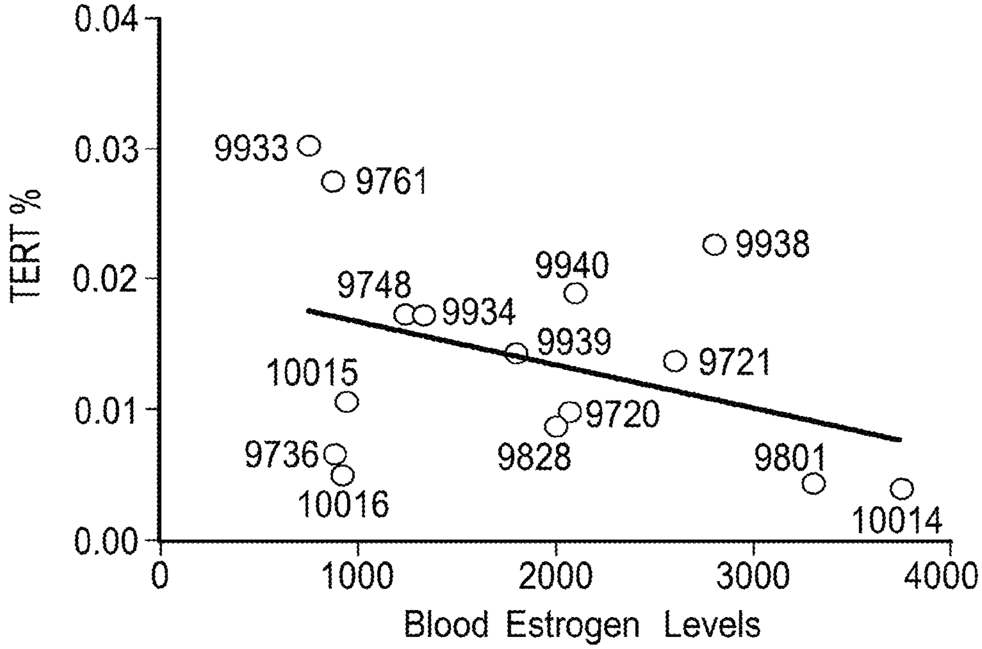
FIGS. 21A, B: WC protein extracts were analyzed by ELISA kit (EIAab).
Figure 21B:
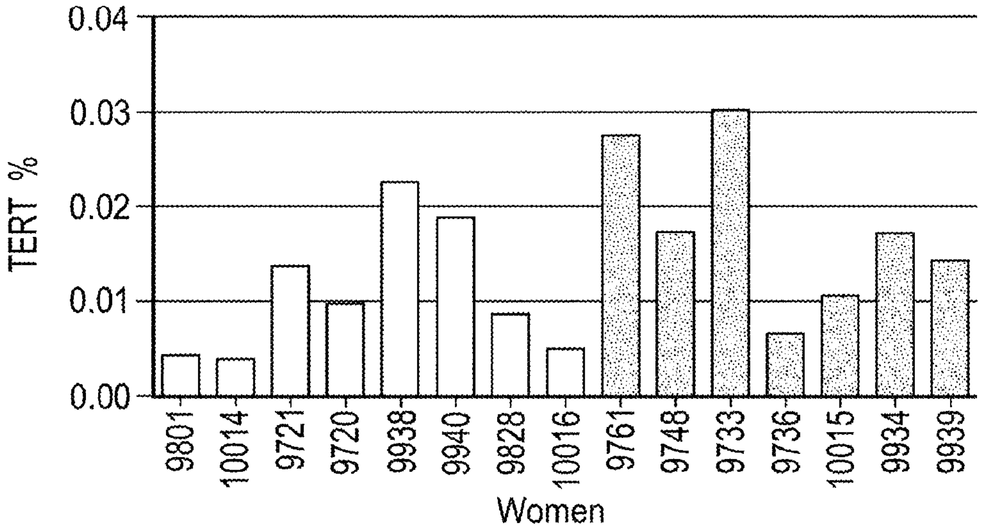
FIG. 21B-Telomerase expression of individual women.

Evaluation of IVF patients provided for the finding that there exists a correlation between an infertility diagnosis and telomerase activity (FIGS. 20A, B), with $n=9$ for female infertility, $n=12$ for male infertility ($p=0.159$. Similarly, the relative Telomerase expression in women undergoing IVF was evaluated (FIGS. 21A, B). WC protein extracts were analyzed by ELISA kit (EIAab). FIG. 21A-Telomerase expression was calculated as % of the total protein expression with correlation to blood estrogen levels. FIG. 21B-Telomerase expression of individual women.

Taken together, these studies supported that variations exist in telomerase activity in women undergoing IVF (in WC and BD fractions). A negative correlation exists in terms of enzyme activity as compared to blood estrogen levels. Preliminary analysis assessing the women based on their cause of infertility, showed alterations in telomerase activity, where low telo activity was observed within the group of "female infertility factors" and not in the group of "male infertility factors". These results further support that the embodied compounds would be useful specifically when treating patients undergoing IVF, as part of infertility management.

Example 5

Increasing Telomerase by the Embodied Compounds Protected Mouse Testes from Damages Induced by X-Ray Radiation

Background and Materials and Methods

Telomerase Enzyme is responsible for the re-elongation of telomeres at the ends of chromosomes and for providing genome stability. Most somatic cells contain low or undetected expression of telomerase but during the spermatogenesis process telomerase is active and its catalytic subunit TERT is expressed. Factors that altered the spermatogenesis process like X-ray radiation significantly affect male fertility. It became of interest therefore as to whether the embodied compounds of this invention, would be able to compensate or otherwise protect the testis from the damaging effects of radiation exposure.

Toward this end, ICR mice (3 months old) were injected with 6 mg/kg of Compound 79, Compound 68 or Compound 70, or mice were subjected to X-ray radiation (2.5 Gy) followed by immediately injection of the respective compounds. Control mice were untreated or vehicle treated with or without exposure to X-ray radiation. The testes were removed 12 hrs after treatments and subjected to protein extracts or total RNA preparations for the examination of telomerase activity by TRAP assay, telomerase expression by Western blot and real time PCR. Testes were also taken for immunohistochemical and immunofluorescence analysis with various spermatogenesis markers. Epididymis was also taken for sperm count.

Results

The compounds protected mouse testes from X-ray induced morphological damage. H&E staining shows a significant destruction in the morphology of the testicular tissue particularly in the spermatogonia cells layer, following irradiation (FIG. 22). Compound 68 treatment, however, protected the spermatogonia cells layer from the damaging effects of X-ray and the morphology of the testicular tissue remained intact.

Figure 23A:
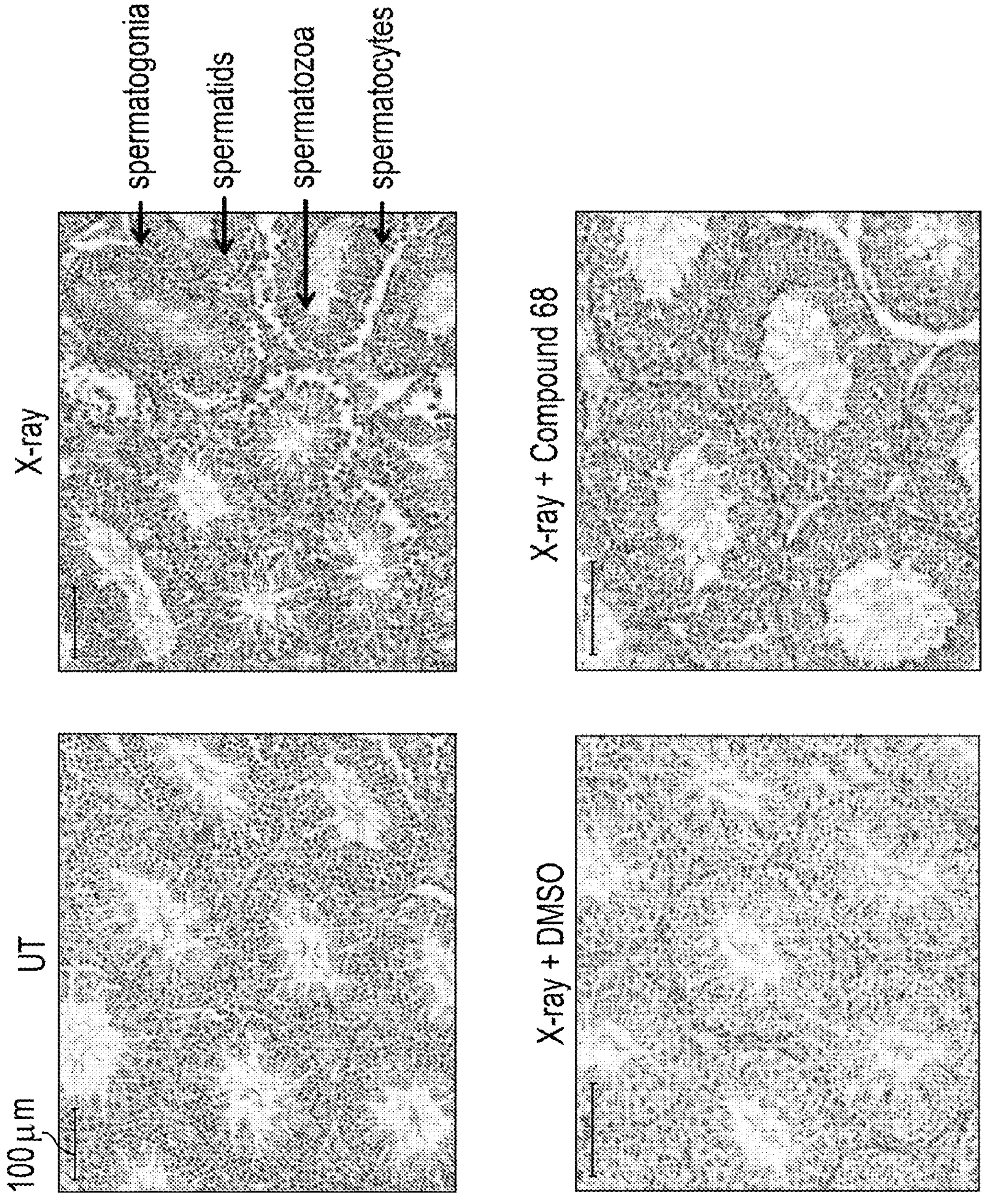
FIGS. 23A, B: Examination of CREM expression in the testis before and after X-ray irradiation, revealed a significant alteration in the expression pattern in X-ray treated testis compared to the untreated mice. Compound 68 and Compound 70 treatments restored the expression of the spermatogenesis markers. ICR mice (3 months old) were subjected to X ray radiation (2.5 Gy) followed by immediately injection of DMSO or Compound 68 (FIG. 23A) and Compound 70 (FIG. 23B). The testes were removed 12 hrs after treatments and stained with CREM marker.
Figure 23B:
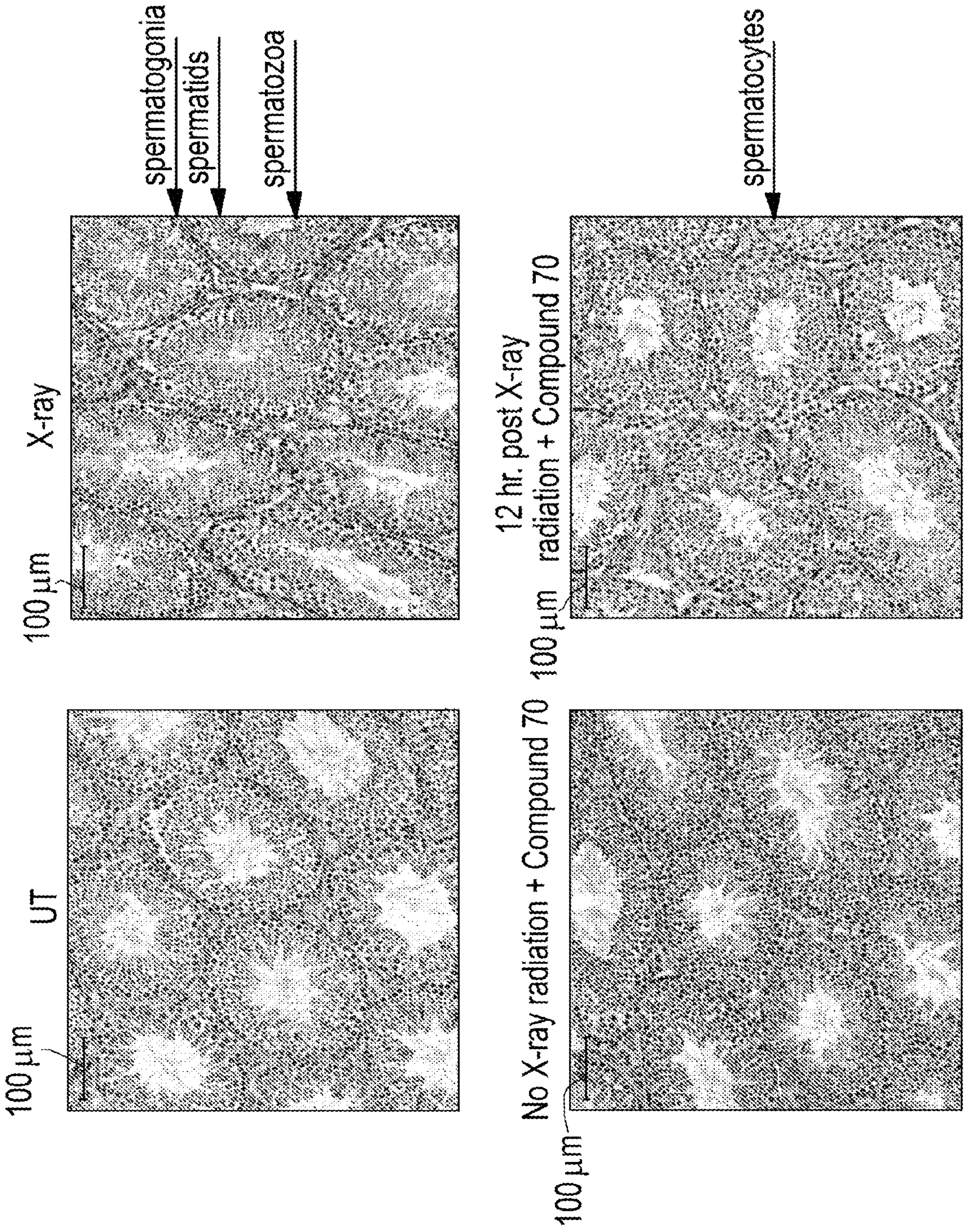

There is a beneficial effect of Compound 68 and Compound 70 on CREM expression in X-ray irradiated testicular tissue. Examination of CREM expression in the testis before and after X-ray radiation, revealed a significant alteration in the expression pattern in X-ray treated testis compared to the untreated mice (FIGS. 23A, B). Compound 68 and Compound 70 treatments restored the expression of the spermatogenesis markers (FIG. 23A and FIG. 23B, respectively).

Figure 24:
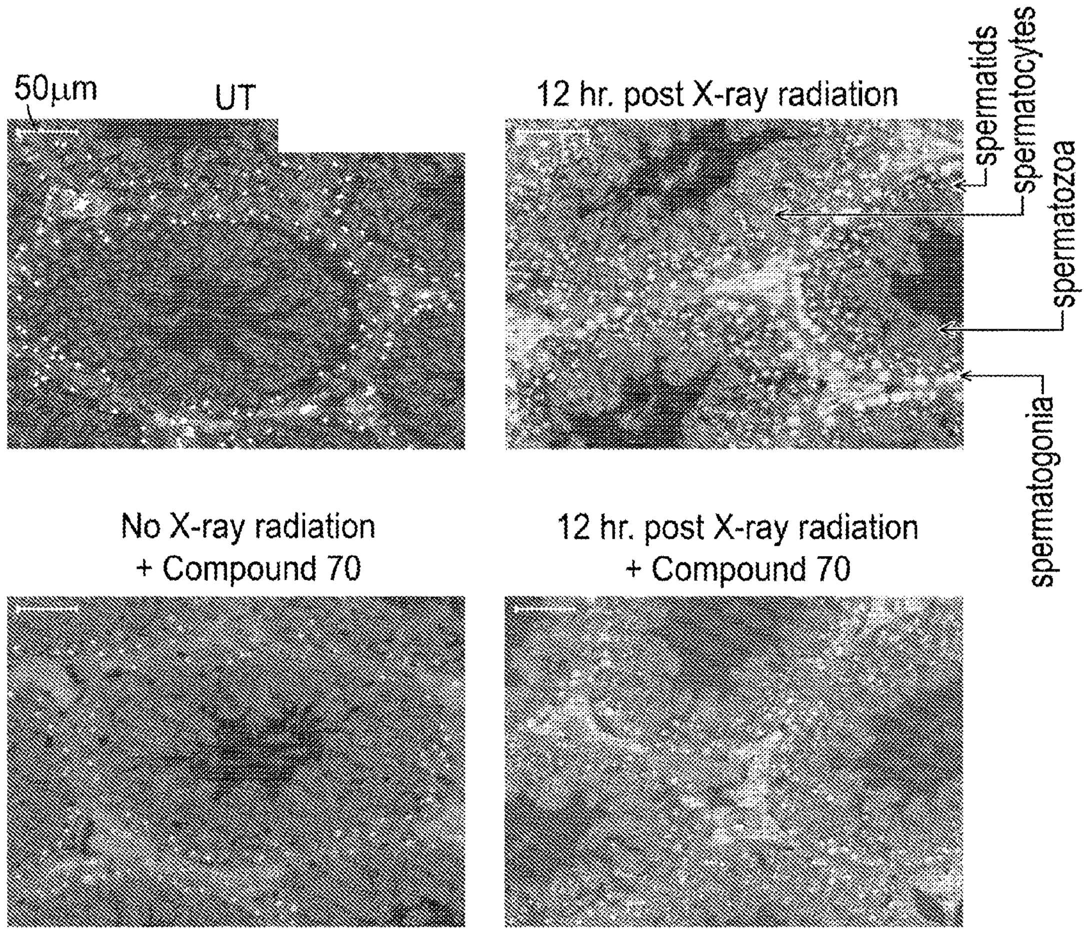
FIG. 24: IF analysis of γ-H2AX (green) marker showed a significant increase of DSB formation 12 hrs post-irradiation,compared to UT samples. In addition, treatment with Compound 70 only did not cause DNA damages. In irradiated mice, Compound 70 treatment demonstrated a decreased in the expression levels of γ-H2AX in the various cell types, mainly in spermatogonia, indicating that Compound 70 treatment protects the testis tissue from DNA damages induced by X-ray radiation. ICR mice (3 months old) were subjected to X-ray radiation (2.5 Gy) followed by immediate injection of Compound 70. For control, mice were treated with the compound without irradiation. The testes were removed 12 hrs after treatments and stained with γ-H2AX antibody.

Compound 70 treatment protected mouse testes from the X-ray radiation damage, as well (FIG. 24). IF analysis of γ-H2AX (green) marker showed a significant increase of DSB formation 12 hrs post-irradiation, compared to UT samples. In addition, treatment with Compound 70 only did not cause DNA damage. In irradiated mice, Compound 70 treatment demonstrated a decrease in the expression levels of γ-H2AX in the various cell types, mainly in spermatogonia, indicating that Compound 70 treatment protects the testis tissue from DNA damage induced by X-ray radiation.

Figure 25A:
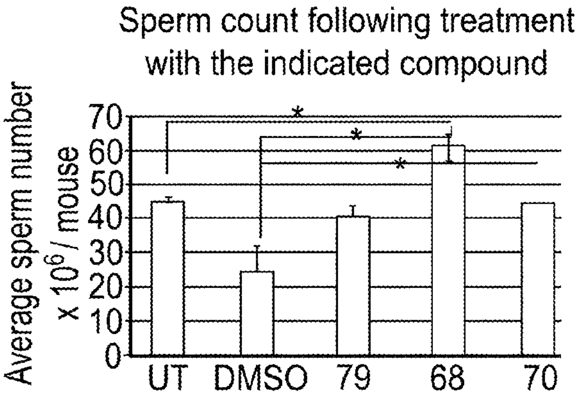
FIGS. 25A, 25B, 25C and 25D: Measurement of sperm cells number from the epididymis in non-radiated mice followed by the indicated treatments shows a significant increase 12 hrs. post-Compound 68 and Compound 70 treatments compared to DMSO, respectively. Sperm count from X-ray treated and untreated mice revealed a significant reduction in sperm count, while treatment of X-ray irradiated mice with the indicated compounds significantly increased the numbers of sperms in the epididymis by 1.5-2.7 folds 12 hrs post-radiation (FIGS. 25A and 25B) Treatment of irradiated mice with Compound 68 increased sperm count at 9 and 30 days post irradiation (FIGS. 25C and 25D).
Figure 25B:
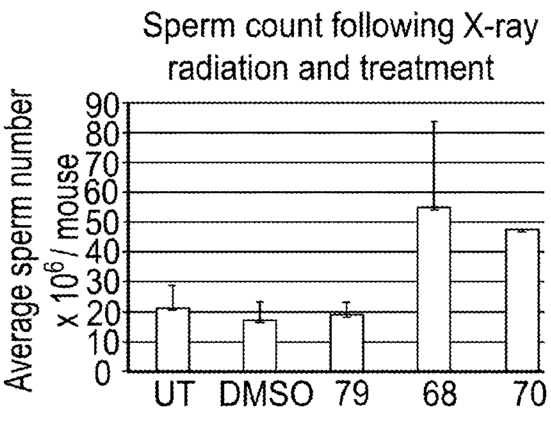
Figure 25C:
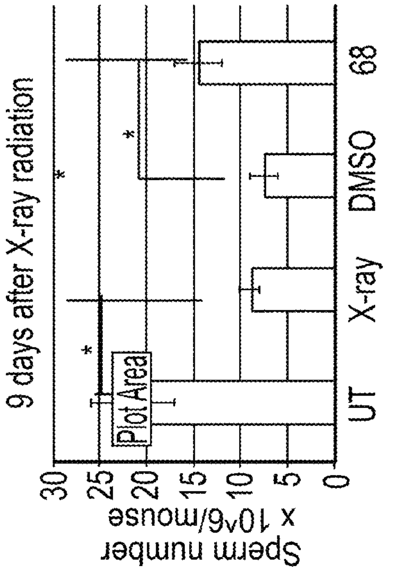
Figure 25D:
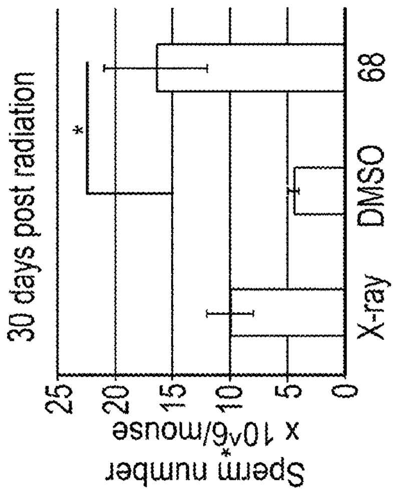

Beneficial effect of the embodied compounds on sperm count at different times after X-ray radiation (FIGS. 25A-D). Measurement of sperm cells number from the epididymis in non-irradiated mice followed by treatment with the indicated showed a significant increase 12 hrs. post treatments with Compound 68 and Compound 70, as compared to DMSO. Sperm count from X-ray treated and untreated mice revealed a significant reduction in sperm count, while treatment with Compound 68 and Compound 70 of X-ray irradiated mice significantly increased the numbers of sperms in the epididymis by 1.5-2.7 folds 12 hrs post-radiation (FIGS. 25A and B). Treatment of irradiated mice with Compound 70 increased sperm count at 9 and 30 days post irradiation (FIGS. 25C and D).

Figure 26B:
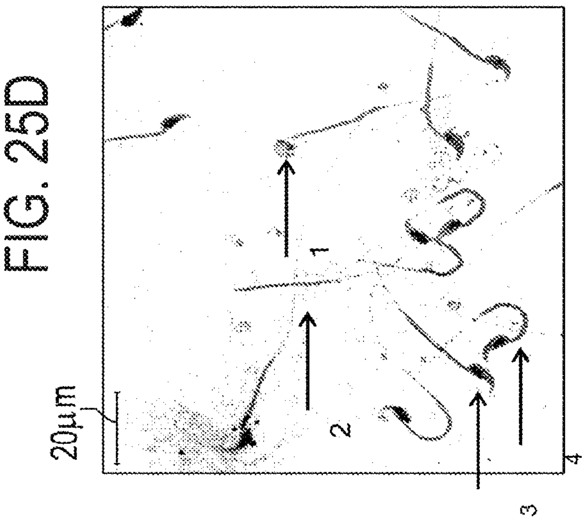

The beneficial effect of the embodied compounds on sperm morphology is also demonstrated at different times after X-ray radiation (FIGS. 26A, B). FIG. 26A quantitatively demonstrates the reduction in the number of defective sperm cells, based on morphologic evaluation, following X-ray exposure, when cells are treated with Compound 68 or Compound 70. FIG. 26B provides a micrograph of sperm morphology as a frame of reference. The embodied compounds therefore not only increase sperm count, but also increase sperm quality.

Figure 27A:
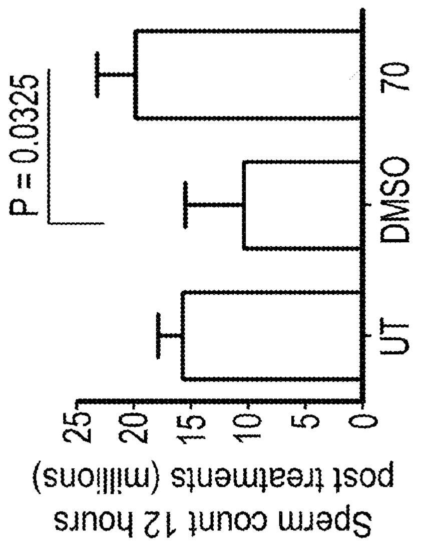
FIGS. 27A and 27B: Embodied compound 70 treatment increased sperm counts (FIG. 27A) and motility (FIG. 27B) in old mice (16 months old) even after a single injection (6 mg/Kg). n=6 mice per group, t test.
Figure 27B:
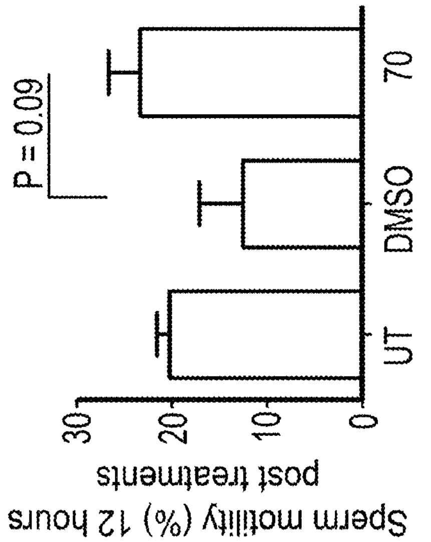

FIGS. 27A, B demonstrate the positive effect of the embodied compound 70 on sperm count (FIG. 27A) and motility (FIG. 27B) in old mice (16 months). The production of sperm in old mice is relatively low and unlike in younger mice, it is sensitive to DMSO treatment. However treatment with the embodied compounds not only overcome the reduction of sperm count induced by DMSO but also increased sperm production over the basal level in old mice which indicates the potential of these compounds to increase male fertility in older subjects.

Taken together, these results support the ability of the embodied compounds of this invention in X-ray irradiated testes to significantly restore tissue morphology, increase CREM expression and decrease DSB formation. Furthermore, treatment with select compounds, such as Compound 68 increased the sperm count in the epididymis, at different time points post radiation, indicating its promise as a therapy to restore male fertility in irradiated subjects. Finally, protective effects in elder mice hold promise for improving fertility in an aging or prematurely aging population.

Figure 28A:
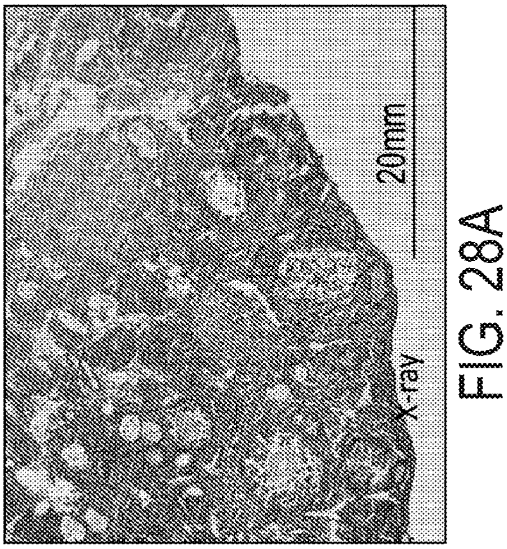
FIGS. 28A, 28B and 28C: Ovarian tissue histopathology following irradiation (FIG. 28A), followed by treatment with Compound 70 (FIG. 28C) or DMSO carrier (FIG. 28B).
Figure 28B:
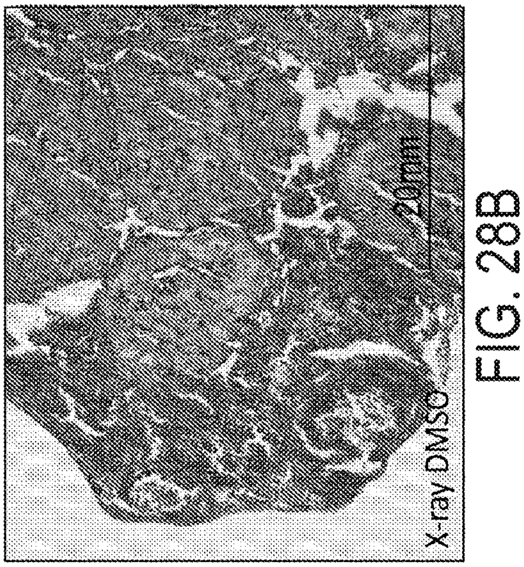
Figure 28C:
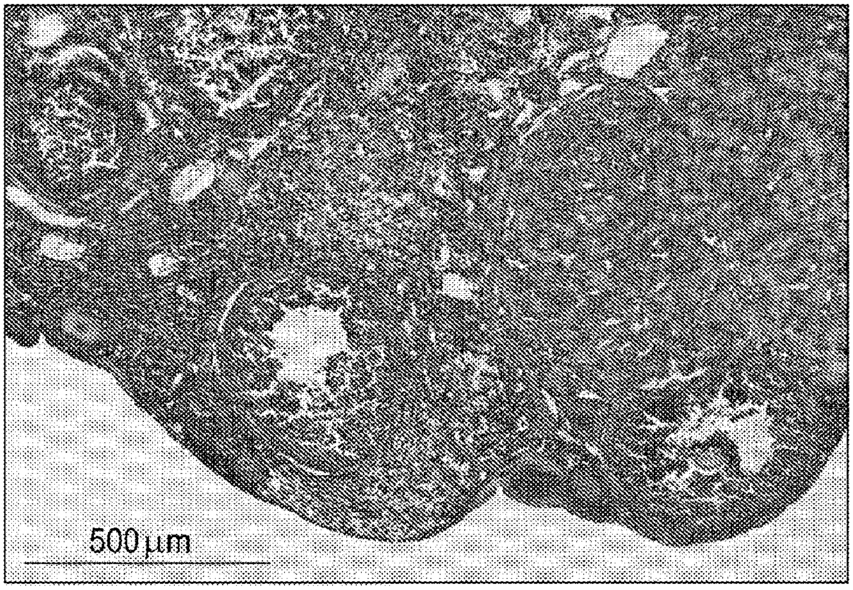

The protective effect in gonadal tissue following irradiation is also seen in female subjects. FIGS. 28A-C depicts an H&E stained ovarian section of X-ray irradiated tissue, where Compound 70 treatment following irradiation clearly rescues ovarian tissue exposed to radiation.

The embodied compounds also modulate sex hormone production (FIGS. 29A-D). Expression of the gonadotropins LH and FSH was assessed in cells derived from murine pituitary gland. Compound 79 increased expression of LH above untreated levels at 6 hours post treatment, and decreased FSH levels at 12 hours, while compounds 68 and 70 increased LH production above untreated levels at 12 hours and decreased FSH expression relative to untreated samples at 6 hours, as assessed by RT-PCR.

Figure 29A:
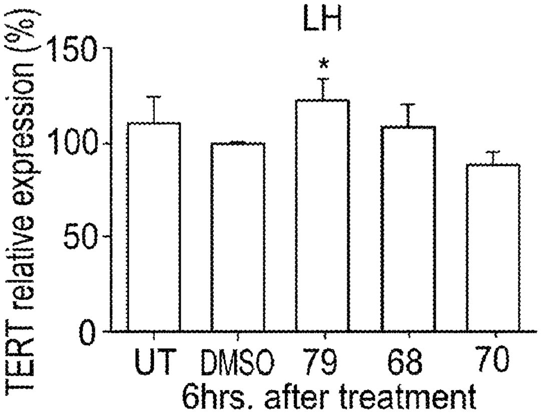
FIGS. 29A, 29B, 29C and 29D: The embodied compounds affect the expression of gonadotropin hormones in pituitary gland cells. Cells (L T2) derived from the mouse pituitary gland were assessed for their secretion of LH and FSH at 6 (FIGS. 29A and 29B) and 12 hours (FIGS. 29C and 29D) following treatment with the indicated embodied compounds (50 nM). FSH and LH expression was determined by RT-PCR, and quantified from 5 different experiments, as assessed for significance, using the t test, one way ANOVA.
Figure 29B:
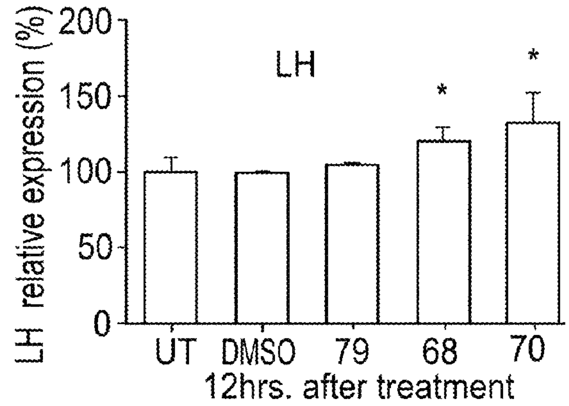
Figure 29C:
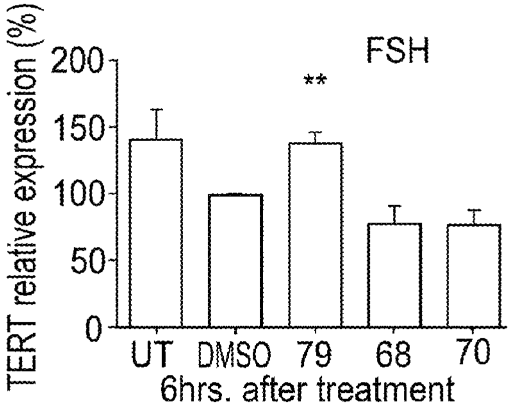
Figure 29D:
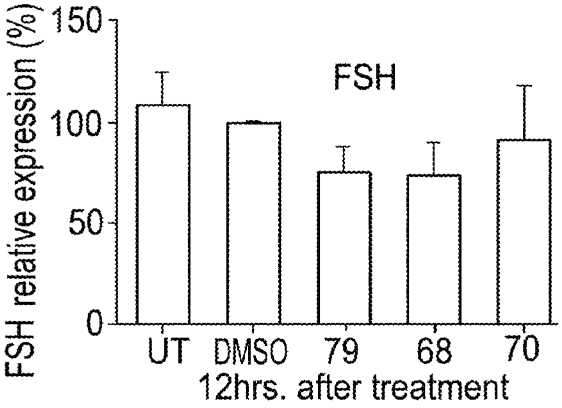
Figure 30A:
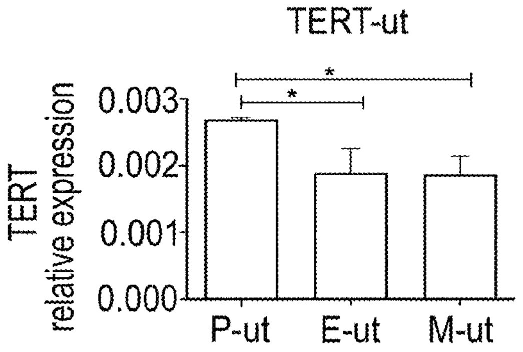
FIGS. 30A, 30B, 30C, 30D, 30E and 30F. The embodied compounds affect the expression of gonadotropin hormones in vivo in female reproductive tissue. Uterine tissue expression of telomerase correlates with gonadotropin expression and the embodied compounds accelerate responsiveness/progression through the cycle. Assessment of telomerase versus LH and FSH expression in different states Pro-estrus (P), estrus (E) and met-estrus (M) in compound 534 treated and control female mice is shown.
Figure 30B:
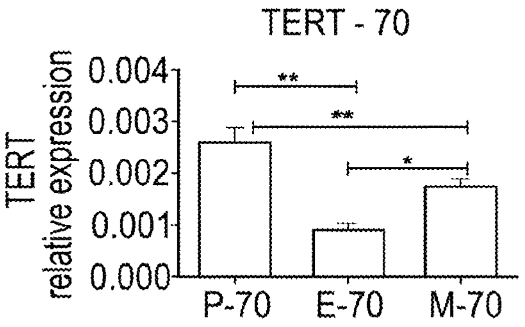
Figure 30C:
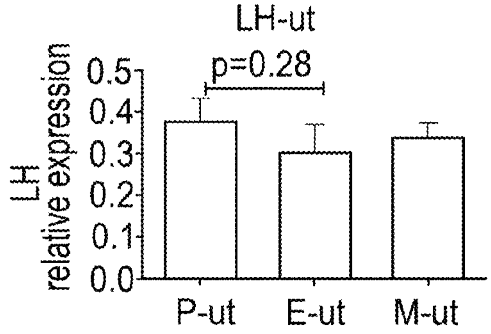
Figure 30D:
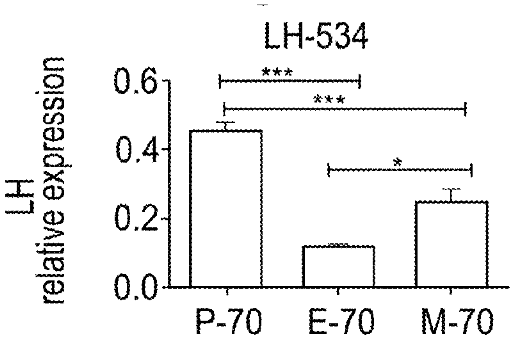
Figure 30E:
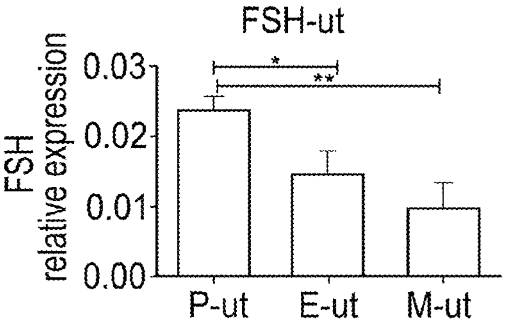
Figure 30F:
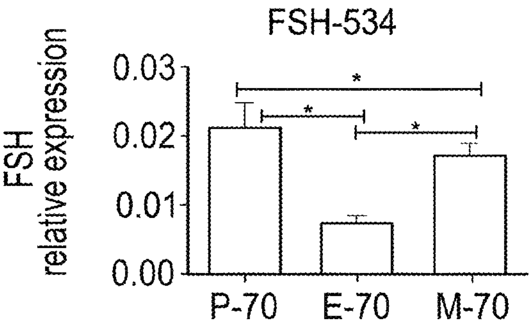

FIGS. 29A=D demonstrates the effect of compound 534 on the expression of gonadotropins: LH and FSH in a pituitary gland cell line. FIGS. 30A-F demonstrates the results of expression of LH and FSH 12 hours after treatment with compound 534 and control animals, where there is a correlation between the telomerase expression and the gonadotropin expression, in control and treated mice. Animals in pro-estrus (P) show the highest expression of telomerase (FIG. 30A), and concomitantly high levels of LH (FIG. 30C) and FSH (FIG. 30E), and progression through estrus and met-estrus, similarly LH expression follows that of telomerase expression and the trend appears with respect to FSH, as well. In animals treated with compound-534, 12 hours after treatment, it would seem that more animals went through estrus (E) and met-estrus (M), i.e. the compound seems to accelerate the cycle, as noted above (Compare FIG. 30B versus 30A, 30D versus 30C and 30F versus 30E).

The relative modulation of expression of these gonadotropins plays an important role in both male and female fertility, supporting an effect of the compounds activity, as well, in modulation of gonadotropin expression.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:
1. A method of promoting, improving, recovering or restoring fertility in a subject in which fertility has been impaired by ionizing radiation to treat a cancerous or precancerous condition, comprising administering to the subject a compound represented by the structure of any of:
VII
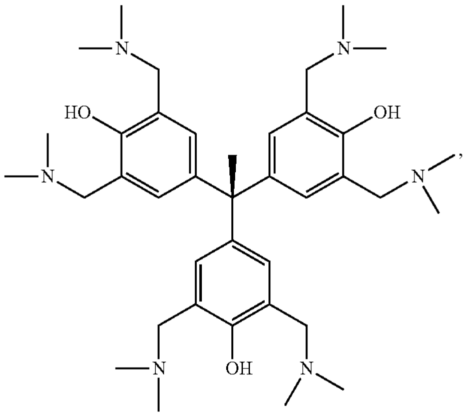
,
VIII
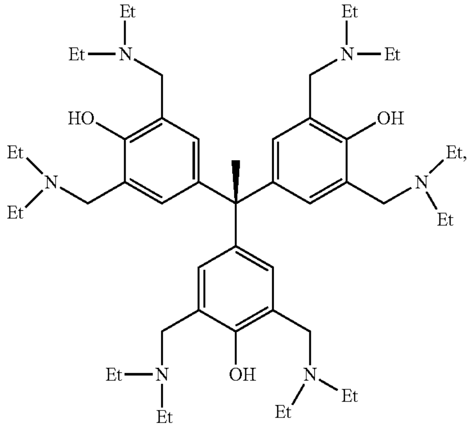
,
IX
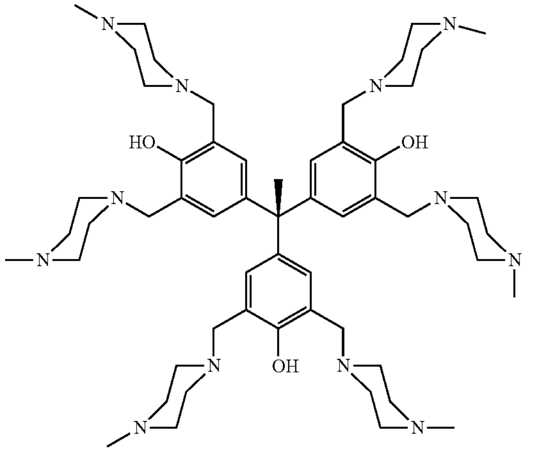
.
X
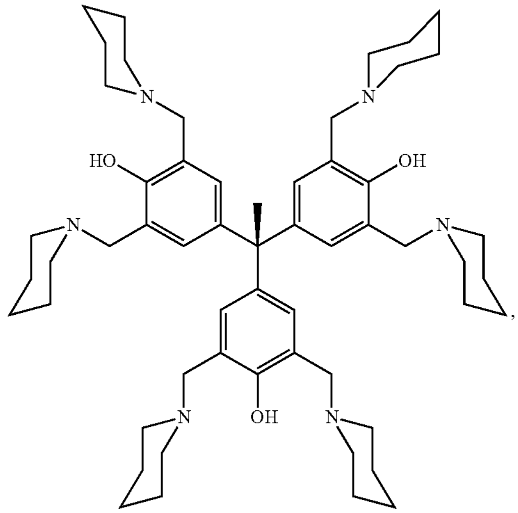
,
XI
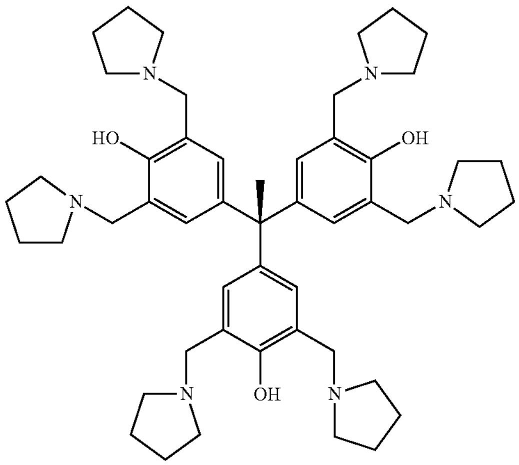
,
XII
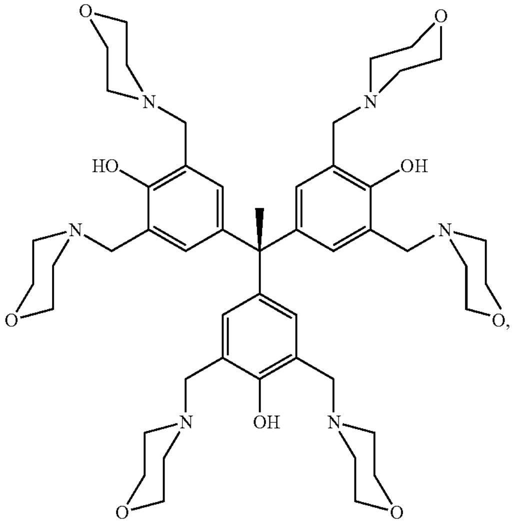
,

XV

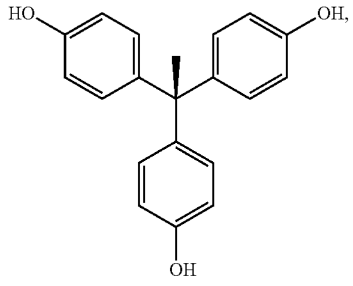

or

XVI

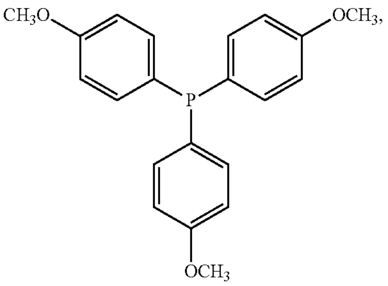

or its isomer, pharmaceutically acceptable salt, pharmaceutical product, hydrate, N-oxide, crystal or any combination thereof.

2. The method of claim 1, wherein promoting, improving, recovering or restoring fertility in a subject beneficially modulates gonadotropin expression or steroid hormone expression in terms of timing or quantity or a combination thereof.

3. The method of claim 1, wherein promoting, improving, recovering or restoring fertility in a subject improves follicle maturation in terms of timing or quantity or a combination thereof.

4. The method of claim 1, wherein promoting, improving, recovering or restoring fertility in a subject improves sperm quantity, quality, motility or a combination thereof.

5. The method of claim 1, wherein said compound is represented by the structure of formula VII:

VII

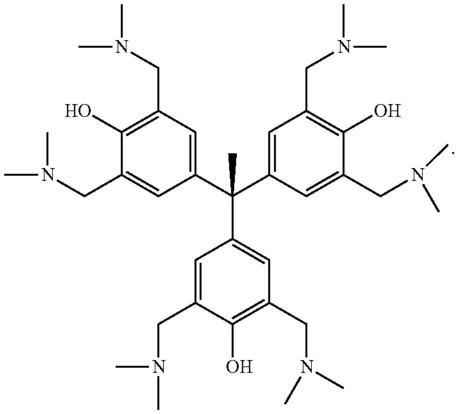

6. The method of claim 1, wherein said compound is represented by the structure of formula VIII:

VIII

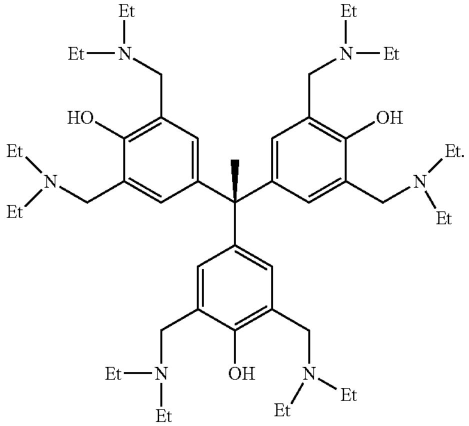

7. The method of claim 1, wherein said compound is represented by the structure of formula IX:

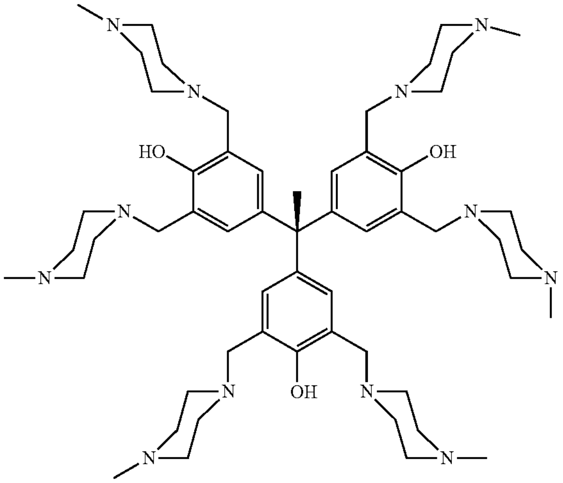

8. The method of claim 1, wherein said compound is represented by the structure of formula X:

X

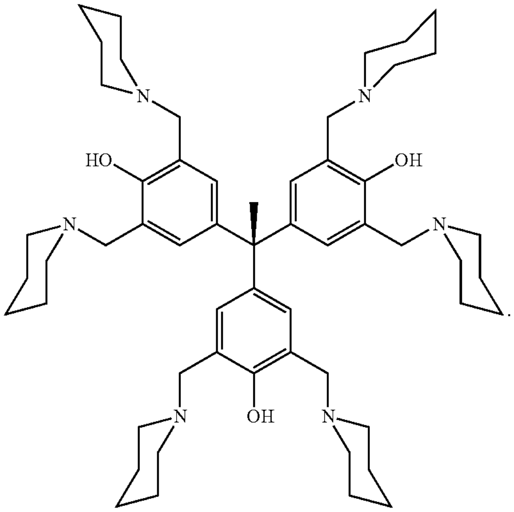

9. The method of claim 1, wherein said compound is represented by the structure of formula XI:

XI

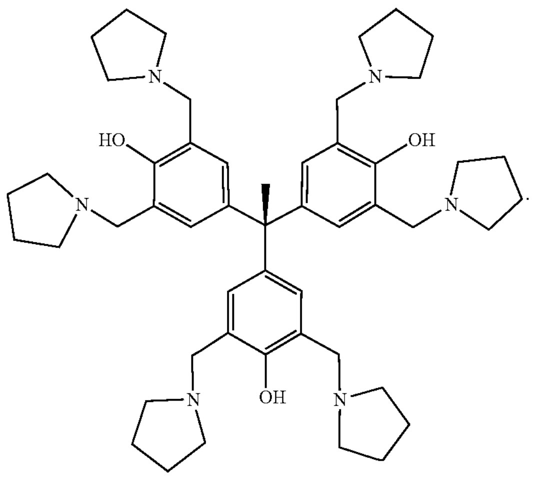

10. The method of claim 1, wherein said compound is represented by the structure of formula XII:

XII

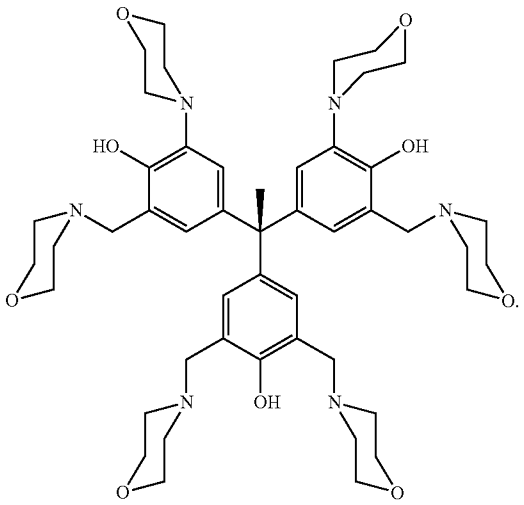

11. The method of claim 1, wherein said compound is represented by the structure of formula XV:

XV

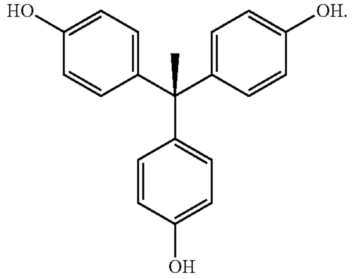

12. The method of claim 1, wherein said compound is represented by the structure of formula XVI:

XVI

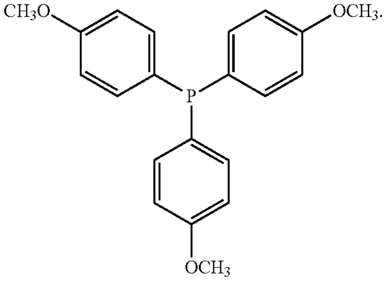

13. The method of claim 1, wherein a pharmaceutical composition comprising said compound is administered.

* * * * *